United States Patent
Oida et al.

[11] Patent Number: 5,856,556
[45] Date of Patent: Jan. 5, 1999

[54] AZETIDINONE DERIVATIVES, A PROCESS FOR THEIR PREPARATION AND THEIR USE AS INTERMEDIATES IN THE PREPARATION OF CARBAPENEM ANTIBIOTICS

[75] Inventors: Sadao Oida; Akira Yoshida; Yawara Tajima; Noriko Takeda, all of Hiromachi, Japan

[73] Assignee: Sankyo Company, Limited, Tokyo, Japan

[21] Appl. No.: 35,915

[22] Filed: Mar. 23, 1993

Related U.S. Application Data

[63] Continuation of Ser. No. 935,642, Aug. 25, 1992, abandoned, which is a continuation of Ser. No. 810,304, Dec. 19, 1991, abandoned, which is a continuation of Ser. No. 697,532, Apr. 30, 1991, abandoned, which is a continuation of Ser. No. 481,717, Feb. 15, 1990, abandoned, which is a continuation of Ser. No. 18,794, Feb. 19, 1987, abandoned, which is a continuation of Ser. No. 873,856, Jun. 11, 1986, abandoned, which is a continuation of Ser. No. 742,132, Jun. 6, 1985, abandoned, which is a continuation of Ser. No. 525,616, Aug. 22, 1983, abandoned.

[30] Foreign Application Priority Data

Aug. 24, 1982 [JP] Japan .................................. 57-145574
Sep. 10, 1982 [JP] Japan .................................. 57-158604

[51] Int. Cl.$^6$ ..................... C07D 477/00; C07D 205/08; C07F 9/568; C07F 7/18; C07C 333/00
[52] U.S. Cl. .......................................... 540/350; 540/200
[58] Field of Search ............................................. 540/350

[56] References Cited

U.S. PATENT DOCUMENTS 4,347,183  8/1982  Alfonso, I ............................ 260/245.3
4,348,320  9/1982  Bouffard et al. .

FOREIGN PATENT DOCUMENTS 0 037 592  10/1981  European Pat. Off. .
0 045 198   2/1982  European Pat. Off. .
0 057 565   8/1982  European Pat. Off. .
0 060 077   9/1982  European Pat. Off. .
2 383 960  10/1978  France .
57-9784     1/1982  Japan .

OTHER PUBLICATIONS

Oida II, Chem Pharm Bull 29, 3158 (1981).
Woodward et al, J.A.C.S. 101, 6300 (1981) ("Lang").
Adams et al, Organic Reactions 14, 274–5 (1965).
Perrone et al. Tet. Letters 25, 2400 (1984.
Alfonso II, J.A.C.S. 104, 6138.
Ponsford et al. J.C.S. Chem Comm 1979, p. 847.
Oida I, Chem Pharm Bull 28, 3494.
Oida et al, Chem. Pharm. Bull 28, 3494 (1980).
Kametoni et al J.C.S. Perkins I 1981, p. 964.
CRC Handbook, 46th Edition, p. F–121 (1965).
Pfaendler, J.A.C.S. 103, 4526 (1981).
Frankel, J. Org. Chem 16, (1951) p. 1513 only.
Stork, J.A.C.S. 73, 4742 (1951.
Kuchenov et al. Chemistry of Carboxylic Acids and Esters, (1969), pp. 199–200.
Pine, Ed, "Organic Chemistry, 4th Edition", pp. 79–82 (1981.
Int. Tables for X–Ray Crystallography (1959), vol. II pp. 60–64.
Allen et al, J. Chem. Inf. Comput. Sci 1991, 31, p. 187.

*Primary Examiner*—Mark L. Berch
*Attorney, Agent, or Firm*—Frishauf, Holtz, Goodman, Langer & Chick, P.C.

[57] ABSTRACT

Compounds of formula (I):

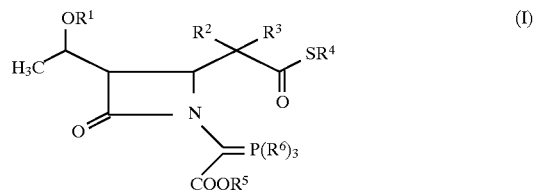

(wherein $R^1$ represents hydrogen or a hydroxy-protecting group, $R^2$ and $R^3$ represent hydrogen, alkyl or aryl; $R^4$ represents optionally substituted alkyl, alicyclic heterocyclic, aryl, aromatic heterocyclic, optionally substituted alkenyl or optionally substituted alkynyl; $R^5$ represents hydrogen or a carboxy-protecting group; and $R^6$ represents alkoxy, aryloxy, dialkylamino or diarylamino or two or $R^6$ together represent o-phenylenedioxy or three together represent $CH^3C(-CH_2O-)_3$) may be prepared by reacting the corresponding carbonyl compound with a compound of formula $P(R^6)_3$. Compounds (I) may be cyclised to prepare carbopenem derivatives, many of which have valuable antibiotic activity.

17 Claims, No Drawings

AZETIDINONE DERIVATIVES, A PROCESS FOR THEIR PREPARATION AND THEIR USE AS INTERMEDIATES IN THE PREPARATION OF CARBAPENEM ANTIBIOTICS

This application is a continuation of application Ser. No. 07/935,642 filed on Aug. 25, 1992, (abandoned); which is a continuation of Ser. No. 07/810,304 filed on Dec. 19, 1991, (abandoned); which is a continuation of Ser. No. 07/697,532 filed on Apr. 30, 1991, (abandoned); which is a continuation of Ser. No. 07/481,717 filed on Feb. 15, 1990, (abandoned); which is a continuation of Ser. No. 07/018,794 filed on Feb. 19, 1987, (abandoned); which is a continuation of Ser. No. 06/873,856 filed on Jun. 11, 1986, (abandoned); which is a continuation of Ser. No. 06/742,132 filed on Jun. 6, 1985, (abandoned); which is a continuation of Ser. No. 06/525,616 filed on Aug. 22, 1983, (abandoned).

BACKGROUND TO THE INVENTION

The present invention relates to a series of new azetidinone derivatives, which are of value as intermediates in the preparation of certain carbapenem derivatives, many of which have valuable antibiotic properties. The invention also provides processes for the preparation of such azetidinone and carbapenem derivatives.

The carbapenems are a group of β-lactam compounds characterised by the basic structure (A):

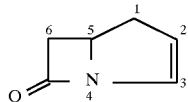

This structure is known as "carbapenem" and forms the basis for the generally accepted semi-systematic nomenclature of carbapenem derivatives, which system is used herein.

Although many carbapenem derivatives have, in recent years, been proposed for use as antibiotics, many of them suffer from a problem which is common in the pharmaceutical industry: namely, preparation of these compounds is difficult or can be carried out only with low yields. There can be many reasons why these problems arise, for example starting materials may be difficult or even impossible to prepare on a commercial basis or may be obtainable only on a restricted basis or at high cost; alternatively, by the time the many process steps normally needed to produce carbapenem compounds have been carried out, the overall yield may be so small as to render the process uneconomic, In copending U.S. patent application Ser. No. 407,914 filed 13th Aug. 1982, a series of carbapenem derivatives having excellent antibiotic activity has been disclosed and a process for producing such compounds is also disclosed.

Another process which can be used for preparing compounds of the type disclosed in the aforementioned U.S. patent application is disclosed in European Patent Specification No. 58317. The Process disclosed in this European Patent Specification includes reacting a compound of formula (B):

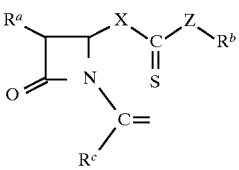

(in which: $R^a$ represents a hydrogen atom, an alkyl group, an acylamino group or a substituted alkyl group; $R^b$ can represent a variety of organic groups, including alkyl and aryl groups, which may be substituted or unsubstituted; $R^c$ represents, inter alia, a carboxyl group or an esterified carboxyl group; Z represents, inter alia, a sulphur or oxygen atom; and X represents a sulphur or oxygen atom or a methylene group) with a trialkyl phosphite at a temperature within the range from 20° to 80° C. It has been reported by Afonso et al. [J. Am. Chem. Soc., 104, 6138 (1982)] that the conditions under which this reaction is carried out are highly critical as the reaction of these two compounds can give rise to a phosphoranylidene derivative of formula (C):

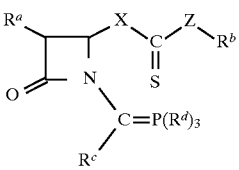

(in which $R^a$, $R^b$, $R^c$, X and Z are as defined above and $R^d$ represents an alkoxy group). This phosphoranylidene derivative will not undergo cyclisation to give a penem or carbapenem compound and thus represents a wasted by-product.

It has also been reported by Ponsford et al. (J.C.S. Chem. Comm., 1979, 847), Oida et al. [Chem. Pharm. Bull., 28, 3494 (1980)] and Kametani et al. (J.C.S. Perkin I, 1981, 964) that it is extremely difficult to undertake an intramolecular Wittig reaction with compounds of formula (C), but in which the sulphur atom has been replaced by an oxygen atom, and X is a methylene group, Z is a sulphur atom and $R^d$ is a phenyl group. Indeed, in the process disclosed in the aforementioned European Patent Application, one method of preparing the starting material of formula (B) includes a step in which a carbonyl oxygen atom is replaced by a sulphur atom (see, for example, Preparations R. S, T and U).

We have now discovered that compounds similar to those of formula (B) in which X represents a methylene group and $R^b$ represents a certain limited range of substituents, but in which the sulphur atom has been replaced by an oxygen atom, can be reacted with a limited class of phosphites and phosphorus amides, to give novel compounds similar to those of formula (C) and that surprisingly these novel compounds can readily be cyclised to give various carbapenem derivatives, many of which are of considerable interest as antibiotics. Certain of the carbapenem derivatives thus prepared are disclosed in copending U.S. patent application Ser. No. 407,914. filed 13th Aug. 1982.

BRIEF SUMMARY OF INVENTION

The azetidinone compounds of the present invention, which are of value as intermediates for the preparation of a variety of carbapenem antibiotics, may be represented by the formula (I):

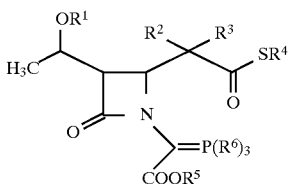

in which:
- $R^1$ represents a hydrogen atom or a hydroxy-protecting group;
- $R^2$ and $R^3$ are the same or different and each represents a hydrogen atom, a $C_1$–$C_6$ alkyl group or an aryl group;
- $R^4$ represents an alkyl group, a substituted alkyl group, an alicyclic heterocyclic group, an aryl group, an aromatic heterocyclic group, an alkenyl group, a substituted alkenyl group, an alkynyl group or a substituted alkynyl group;
- $R^5$ represents a hydrogen atom or a carboxy-protecting group; and
- $R^6$ represents an alkoxy group, an aryloxy group, a dialkylamino group or a diarylamino group, or two of the symbols $R^6$ may together represent an o-phenylenedioxy group, or the three symbols $R^6$ may together represent a group of formula $CH_3$—$C(CH_2$—$O$—$)_3$, and, where there are three groups represented by the symbols $R^6$ these may be the same or different.

Compounds of formula (I) can be prepared by reacting a compound of formula (II):

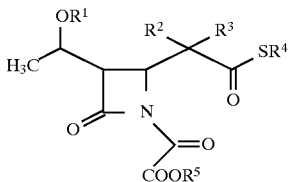

(in which $R^1$, $R^2$, $R^3$, $R^4$ and $R^5$ are as defined above) with a compound of formula (III):

(in which $R^6$ is as defined above).

Compounds of formula (I) may be cyclised by conventional means, e.g. by heating, to give compounds of formula (IV):

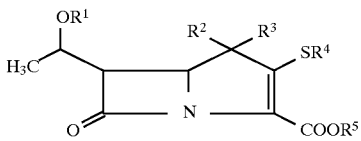

(in which $R^1$, $R^2$, $R^3$, $R^4$ and $R^5$ are as defined above), many of which are of considerable potential interest as carbapenem antibiotics. If desired, the hydroxy-protecting group and/or carboxy-protecting group, which may be represented by $R^1$ or $R^5$, as well as any protecting group which may be included within the groups represented by $R^4$, may subsequently be removed. The compounds of formula (IV) may be converted into the salts of those compounds in which $R^5$ represents a hydrogen atom by conventional salification techniques,

DETAILED DESCRIPTION OF INVENTION

In the compounds of formulae (I), (II) and (IV), $R^1$ represents a hydrogen atom or a hydroxy-protecting group. Since the purpose of the hydroxy-protecting group is merely to protect the hydroxy group from attack during the reactions leading to the preparation of compounds of formulae (I) and (IV), and since this hydroxy-protecting group is normally and preferably removed following preparation of the compound of formula (IV) to leave a free hydroxy group, the nature of the hydroxy-protecting group employed is not critical to the present invention and any hydroxy-protecting group known in the art may be employed. Examples of protecting groups which may be used to protect such alcoholic hydroxy groups include: silyl groups, such as the trimethylsilyl, t-butyldimethylsilyl or triphenylsilyl groups; aralkyl groups, such as the benzyl p-nitrobenzyl, o-nitrobenzyl or m-methoxybenzyl groups; substituted oxycarbonyl groups, such as the benzyloxy-carbonyl, p-nitrobenzyloxycarbonyl, o-nitrobenzyloxy-carbonyl, allyloxycarbonyl, 2-chloroallyloxycarbonyl, 2-methylallyloxycarbonyl, 2,2,2-trichloroethoxycarbonyl, 2,2,2-tribromoethoxycarbonyl, t-butoxycarbonyl, diphenylmethoxycarbonyl or 2-(trimethylsilyl) ethoxycarbonyl groups; ether groups, such as the tetrahydropyranyl, methoxymethyl, 1-ethoxyethyl or 2-(trimethylsilyl) ethoxymethyl groups; and the chloroacetyl group. However, it should be emphasised that these groups are given merely by way of example and a wide range of conventional hydroxy-protecting groups may be employed without limitation.

R2 and R3 may be the same or different and each represents a hydrogen atom, a $C_1$–$C_6$ alkyl group or an aryl group. Examples of alkyl groups which may be represented by $R^2$ and $R^3$ include the methyl, ethyl, propyl and isopropyl groups. An example of an aryl group which may be represented by $R^2$ or $R^3$ is the phenyl group.

$R^4$ represents an alkyl group, a substituted alkyl group, an alicyclic heterocyclic group, an aryl group or an aromatic heterocyclic group.

When $R^4$ represents an alkyl group, this is preferably a $C_1$–$C_6$ group, more preferably a $C_{1-C4}$ group and it may be a straight or branched chain group. Examples include the methyl, ethyl, propyl, isopropyl and t-butyl groups.

Where $R^4$ represents an alicyclic heterocyclic group, it is preferably a group having from 4 to 8 ring carbon atoms and is preferably an alicyclic heterocyclic amino group. In addition, the heterocyclic group may contain a nitrogen atom, an oxygen atom, a sulphur atom, a sulphinyl group, a sulphinyl group or a carbonyl group, and may have one or more substituents attached to the carbon atoms or to any nitrogen atom.

Examples of substituents which may be attached to ring carbon atoms include alkyl, alkoxyalkyl, cyanoalkyl, haloalkyl, alkoxy, hydroxy, amino, acyloxy, acylamino, cyano, azido, carboxy, alkoxycarbonyl, carbamoyl, alkylthio, alkylsulphinyl, alkylsulphonyl and nitro groups and halogen atoms. Examples of substituents which may be attached to ring nitrogen atoms include alkyl, alkenyl, alkynyl, cycloalkyl, cycloalkylalkyl, aryl, aralkyl, acyl, phenacyl, sulpho, alkoxysulphonyl, alkylsulphonyl, alkenylsulphonyl, alkynylsulphonyl, cycloalkylsulphonyl, cycloalkylalkylsulphonyl, arylsulphonyl, aralkylsulphonyl, heteroarylsulphonyl, heteroaralkylsulphonyl, alkoxycarbonyl and aralkyloxycarbonyl groups, as well as groups of formula

(in which $R^{10}$ represents a hydrogen atom or a $C_1$–$C_6$ alkyl group and $R^{11}$ represents a hydrogen atom or an imino-protecting group), groups of formula

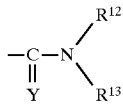

(in which $R^{12}$ and $R^{13}$ are the same or different and each represents a hydrogen atom or a $C_1$–$C_6$ alkyl group and Y represents an oxygen atom, a sulphur atom or an imino group optionally having a $C_1$–$C_6$ alkyl substituent).

The substituents attached to the ring nitrogen atoms and mentioned above may themselves be substituted by one or more of the following substituent groups or atoms: $C_1$–$C_6$ alkyl groups, $C_1$–$C_6$ alkoxy groups, hydroxy groups, amino groups, halogen atoms, $C_1$–$C_6$ aliphatic acylamino groups, cyano groups, azido groups, carboxy groups, $C_2$–$C_7$ alkoxycarbonyl groups, carbamoyl groups, $C_1$–$C_6$ alkylthio groups, $C_1$–$C_6$ alkylsulphinyl groups, $C_1$–$C_6$ alkylsulphonyl groups, nitro groups and groups of formula

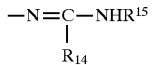

(in which $R^{14}$ and $R^{15}$ are the same or different and each represents a hydrogen atom or a $C_1$–$C_6$ alkyl group).

Examples of preferred alicyclic heterocyclic groups include the azetidinyl, pyrrolidinyl, piperidinyl, morpholinyl, tetrahydropyrimidinyl, thiazolidinyl, oxazolidinyl, hexahydropyrimidinyl, imidazolidinyl and octahydroazocinyl groups, which may optionally be substituted, as noted above.

Particularly preferred substituents for attachment to the ring carbon atoms of these heterocyclic groups are as follows: straight or branched chain $C_1$–$C_6$ alkyl groups, such as the methyl, ethyl, propyl, isopropyl, butyl, isobutyl, sec-butyl, t-butyl, pentyl or isopentyl groups; cycloalkyl groups, such as the cyclopropyl, cyclobutyl, cyclopentyl or cyclohexyl groups; $C_2$–$C_8$ alkoxyalkyl groups, such as the methoxymethyl, ethoxymethyl, propoxymethyl, isopropoxymethyl, butoxymethyl, 1-methoxyethyl, 2-methoxyethyl, 3-methoxypropyl, 2-methoxypropyl or 4-ethoxybutyl groups; (ar)alkoxycarbonylalkyl groups, such as the methoxycarbonylmethyl, ethoxycarbonylmethyl, t-butoxy-carbonylmethyl, benzyloxycarbonylethyl or methoxy-carbonylpropyl groups; $C_2$–$C_7$ cyanoalkyl groups, such as the cyanoethyl, 1-cyanoethyl, 2-cyanoethyl, 3-cyanopropyl, 2-cyanopropyl, or 4-cyanobutyl groups; $C_1$–$C_6$ haloalkyl groups, such as the trifluoromethyl, 2-fluoroethyl, 2,2,2-trifluoroethyl, 2-chloroethyl, 2-bromoethyl, 3-fluoropropyl, 2-fluoropropyl, 4-chlorobutyl or 3-fluorobutyl groups; straight or branched chain $C_1$–$C_6$ alkoxy groups, such as the methoxy, ethoxy, propoxy, isopropoxy, butoxy, isobutoxy, sec-butoxy or t-butoxy groups; halogen atoms, such as the fluorine, chlorine, bromine or iodine atoms; $C_1$–$C_6$ aliphatic acyloxy groups, such as the acetoxy, propionyloxy, butyryloxy or isobutyryloxy groups; $C_1$–$C^6$ aliphatic acylamino groups, such as the acetylamino, propionylamino, butyrylamino or isobutyrylamino groups; the cyano group; the azido group; the carboxy group; $C_2$–$C_7$ alkoxycarbonyl groups, such as the methoxycarbonyl, ethoxycarbonyl, propoxycarbonyl, isopropoxycarbonyl, butoxycarbonyl, isobutoxycarbonyl, sec-butoxycarbonyl or t-butoxycarbonyl groups; the carbamoyl group; straight or branched chain $C_1$–$C_6$ alkylthio groups, such as the methylthio, ethylthio, propylthio, isopropylthio, butylthio or isobutylthio groups; straight or branched chain $C_1$–$C_6$ alkylsulphinyl groups, such as the methylsulphinyl, ethylsulphinyl, propylsulphinyl, isopropylsulphinyl, butylsulphinyl or isobutylsulphinyl groups; straight or branched chain $C_1$–$C_6$ alkylsulphonyl groups, such as the methylsulphonyl, ethylsulphinyl, propylsulphonyl, isopropylsulphonyl, butylsulphonyl or isobutylsulphonyl groups; and the nitro group.

Particularly preferred substituents for attachment to ring nitrogen atoms of the above-mentioned alicyclic heterocyclic groups include: straight or branched chain $C_1$–$C_6$ alkyl groups, such as the methyl, ethyl, propyl, isopropyl, butyl, isobutyl, sec-butyl, t-butyl, pentyl or isopentyl groups; $C_2$–$C_6$ alkenyl groups, such as the vinyl, allyl, 1-propenyl, isopropenyl, 2-butenyl or 2-pentenyl groups; $C_2$–$C_6$ alkynyl groups, such as the ethynyl, 2-propynyl, 2-butynyl or 4-pentynyl groups; $C_3$–$C_8$ cycloalkyl groups, such as the cyclopropyl, cyclobutyl, cyclopentyl, cyclohexyl or cycloheptyl groups; cycloalkylalkyl groups, such as the cyclopropylmethyl, cyclobutylmethyl, cyclopentylmethyl, cyclohexylmethyl, cycloheptylmethyl, 2-cyclopentylethyl, 2-cyclohexylethyl, 3-cyclopentylpropyl, 2-cyclopentylpropyl, 3-cyclohexylpropyl, 2-cyclohexylpropyl, 4-cyclopentylbutyl or 3-cyclohexylbutyl groups; aryl groups, such as the phenyl or naphthyl groups; aralkyl groups, such as the benzyl, phenethyl or 3-phenylpropyl groups; $C_1$–$C_6$ aliphatic acyl groups, such as the formyl, acetyl, propionyl, butyryl, isobutyryl, acryloyl, methacryloyl, crotonoyl, isocrotonoyl, propioloyl or methylpropioloyl groups; cycloalkanecarbonyl groups, such as the cyclopropanecarbonyl, cyclobutanecarbonyl, cyclopentanecarbonyl or cyclohexanecarbonyl groups; cycloalkylalkanoyl groups, such as the cyclopropyl-acetyl, cyclobutylacetyl, cyclopentylacetyl, cyclohexyl-acetyl, 3-cyclopentylpropionyl, 3-cyclohexylpropionyl, 4-cyclopentylbutyryl or 4-cyclohexylbutyryl groups; aromatic acyl groups, such as the benzoyl, 1-naphthoyl or 2-naphthoyl groups; araliphatic acyl groups, such as the phenylacetyl, 1-naphthylacetyl, 3-phenylpropionyl, hydratropoyl, cinnamoyl or phenylpropioloyl groups; heterocyclic acyl groups, such as the furoyl, thenoyl, nicotinoyl, isonicotinoyl, 4-thiazolecarbonyl, 5-pyrimidinecarbonyl or 2-pyrazinecarbonyl groups; heterocyclic-substituted aliphatic acyl groups, such as the 2-thienylacetyl, 3-(2-thienyl)propionyl, 4-thiazolylacetyl, 2-pyridylacetyl, 4-pyridylacetyl, 5-pyrimidinylacetyl, 1-aziridinylacetyl, 1-azetidinylacetyl, 3-azetidinylacetyl, 1-pyrrolidinylacetyl, 2-pyrrolidinylacetyl, 3-pyrrolidinylacetyl, 3-(2-pyrrolidinyl) propionyl, piperidinoacetyl, 2-piperidinylacetyl, 4-piperidinylacetyl or morpholinoacetyl groups; heterocyclyl carbonyl groups, such as the 1-aziridinecarbonyl, 1-azetidinecarbonyl, 3-azetidinecarbonyl, 1-pyrrolidinecarbonyl, 2-pyrrolidinecarbonyl, 3-pyrrolidinecarbonyl, 1-piperidinecarbonyl, 2-piperidinecarbonyl, 4-piperidinecarbonyl or 4-morpholinecarbonyl groups; phenacyl group: the sulpho group; $C_1$–$C_6$ alkoxysulphonyl groups, such as the methoxysulphonyl, ethoxysulphonyl, propoxysulphonyl or isopropoxysulphonyl groups; straight or branched chain $C_1$–$C_6$ alkylsulphonyl groups, such as the methylsulphonyl, ethylsulphinyl, propylsulphonyl, isopropylsulphonyl, butylsulphonyl or isobutylsulphonyl groups; $C_2$–$C_6$ alkenylsulphonyl groups, such as the allylsulphonyl, isopropenylsulphonyl or 2-butenylsulphonyl groups; $C_2$–$C_6$ alkynylsulphonyl groups, such as the ethynylsulphonyl, 2-propynylsulphonyl or 2-butynylsulphonyl groups; cycloalkylsulphonyl groups, such as the cyclopropylsulphonyl, cyclobutylsulphonyl, cyclopentylsulphonyl or cyclohexylsulphonyl groups; cycloalkylalkylsulphonyl groups, such as the cyclopropylmethylsulphionyl, cyclobutylmethylsulphonyl, cyclopentylmethylsulphonyl, cyclohexylmethylsulphonyl, 2-cyclopentylethylsulphonyl, 2-cyclohexylethylsulphonyl, 3-cyclopentylpropylsulphonyl or 2-cyclopentylpropylsulphonyl groups; arylsulphonyl groups, such as the phenylsulphonyl, 1-naphthylsulphonyl or 2-naphthylsulphonyl groups; aralkylsulphonyl groups such as the benzylsulphonyl, phenethylsulphonyl, 3-phenylpropylsulphonyl or 2-phenylpropylsulphonyl groups; heteroarylsulphonyl groups, such as the 2-thienylsulphonyl, 4-thiazolylsulphonyl, 2-pyridylsulphonyl or 4-pyridylsulphonyl groups; hetero aralkylsulphonyl groups. such as the 2-thienylmethylsulphonyl, 3-(2-thienyl)propylsulphonyl, 4-thiazolylmethylsulphonyl, 2-pyridylmethylsulphonyl or 4-pyridylmethylsulphonyl group; groups of formula

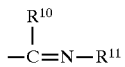

[wherein $R^{10}$ represents a hydrogen atom or a $C_1$–$C_4$ alkyl group (such as a methyl, ethyl, propyl or isopropyl group) and $R^{11}$ represents a hydrogen atom, an aliphatic oxycarbonyl group (such as an allyloxycarbonyl, 2-methylallyloxycarbonyl, 2-chloroallyloxycarbonyl, 2,2,2-trichloroethoxycarbonyl or 2,2,2-tribromoethoxycarbonyl group) or an aralkyloxycarbonyl group (such as a p-nitrobenzyloxycarbonyl or o-nitrobenzyloxycarbonyl group)]; groups of formula

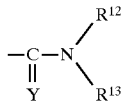

[wherein $R^{12}$ and $R^{13}$ are the same or different and each represents a hydrogen atom or a $C_1$–$C_4$ alkyl group (such as a methyl, ethyl, propyl or isopropyl group) and Y represents an oxygen atom, a sulphur atom or an imino group which may be optionally substituted with a $C_1$–$C_4$ alkyl group (such as a methyl, ethyl, propyl or isopropyl group)]; $C_2$–$C_7$ alkoxycarbonyl groups, such as the methoxycarbonyl, ethoxycarbonyl, butoxycarbonyl, 2,2,2-trichloroethoxycarbonyl or 2, 2,2-tribromoethoxycarbonyl groups; and aralkyloxycarbonyl groups, such as the benzyloxycarbonyl, phenethyloxycarbonyl, p-nitrobenzyloxycarbonyl or o-nitrobenzyloxycarbonyl group.

The substituents attached to the nitrogen atoms above mentioned may themselves optionally be substituted further with one or more groups selected from the following: $C_1$–$C_4$ alkyl groups, such as the methyl, ethyl, propyl or isopropyl group; $C_1$–$C_4$ alkoxy groups, such as the methoxy, ethoxy, propoxy or isopropoxy groups; the hydroxy group; the amino group; halogen atoms, such as the fluorine, chlorine or bromine atoms; $C_1$–$C5$ aliphatic acyloxy groups, such as the acetoxy, propionyloxy, butyryloxy or isobutyryloxy groups; $C_1$–$C_5$ aliphatic acylamino group such as the acetylamino, propionylamino, butyrylamino or isobutyrylamino groups; the cyano group; the azido group; the carboxy group; $C_2$–$C_5$ alkoxycarbonyl groups, such as the methoxycarbonyl, ethoxycarbonyl, propoxycarbonyl or isopropoxycarbonyl groups; the carbamoyl group; $C_1$–$C_4$ alkylthio group such as a methylthio, ethylthio, propylthio or isopropylthio group; $C_1$–$C_4$ alkylsulphinyl groups, such as the methylsulphinyl, ethylsulphinyl, propylsuiphinyl or isopropylsulphinyl groups; $C_1$–$C_4$ alkylsulphonyl groups, such as the methylsulphonyl, ethylsulphonyl, propylsulphonyl or isopropylsulphonyl groups; the nitro group; and groups of formula

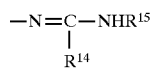

(wherein $R^{14}$ and $R^{15}$ are the same or different and each represents a hydrogen atom or a $C_1$–$C_4$ alkyl group, such as the methyl, ethyl, propyl or isopropyl groups).

Where $R^4$ represents a substituted alkyl group, a variety of substituents are possible and each such alkyl group may bear one or more substituents, which may be the same or different, although a single substituent only is generally preferred. Examples of such substituents include hydroxy groups, protected hydroxy groups, ether groups, amino groups, protected amino groups, optionally substituted amidino groups, aryl groups, alicyclic heterocyclic groups and aromatic heterocyclic groups. The alkyl group itself may be straight or branched chain and is preferably a $C_1$–$C_6$ group, such as those exemplified above where $R^4$ represents an alkyl group.

Where $R^4$ represents a hydroxyalkyl group, the hydroxy group is preferably protected and examples of such groups include the 2-(protected hydroxy)ethyl, 3-(protected hydroxy)propyl, 2-(protected hydroxy)-1-methylethyl and 3-(protected hydroxy)-1-methylpropyl groups. As already explained above, the nature of the protecting group is not critical, as it is normally and preferably removed at the end of the reaction sequence and, accordingly, any protecting group commonly used for the protection of alcoholic hydroxy groups may be employed. Examples of such protecting groups include: alkyl groups, such as the methyl, ethyl or propyl groups; aralkyl groups, such as the benzyl, p-nitrobenzyl or o-nitrobenzyl groups; acyl groups, such as the formyl, acetyl, propionyl, chloroacetyl or benzoyl groups; oxycarbonyl groups, such as the benzyloxycarbonyl, p-nitrobenzyloxycarbonyl, o-nitrobenzyloxycarbonyl, allyloxycarbonyl, 2-chloroallyloxycarbonyl, 2-methylallyloxycarbonyl, 2,2,2-tribromoethoxycarbonyl, t-butoxycarbonyl, diphenylmethoxycarbonyl or 2-(trimethylsilyl)ethoxycarbonyl groups; ether groups, such as the tetrahydropyranyl, methoxymethyl, 1-ethoxyethyl or 2-(trimethylsilyl)ethoxymethyl groups; and aminoalkyl groups, such as the 2-aminoethyl or 3-aminopropyl groups (the amino group may itself be protected by any of the amino-protecting groups suggested hereafter).

Where $R^4$ represents an aminoalkyl group, the amino group is preferably protected and examples of such groups include the 2-(protected amino)ethyl, 2-(protected amino)-1-methylethyl, 2-(protected amino)-1-ethylethyl, 3-(protected amino)propyl, 3-(protected amino)-1-methylpropyl, 2-(protected amino)-2-methylethyl, 2-(protected-N-methylamino) ethyl or 2-(protected-N-methylamino)-1-methylethyl groups. As with the hydroxy-protecting groups, the nature of the amino-protecting group employed is not critical to the invention as it will normally and preferably be removed at the end of the reaction sequence and prior to use of the carbapenem derivative of formula (IV) for therapy. Accordingly, a wide range of amino-protecting groups may be employed without any particular limitation. Examples of suitable amino-protecting groups include: the acyl groups, such as the formyl, acetyl, chloroacetyl, propionyl or benzoyl groups; the oxycarbonyl groups, such as t-butoxycarbonyl, 2,2,2-tribromoethoxycarbonyl, 2-(trimethylsilyl)ethoxycarbonyl, benzyloxycarbonyl, p-nitrobenzyloxycarbonyl or o-nitrobenzyloxycarbonyl groups.

Where $R^4$ represents an amidinoalkyl group, the amidino group is preferably a group of formula

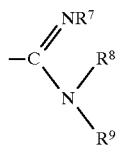

in which $R^7$, $R^8$ and $R^9$ are the same or different and each represents a hydrogen atom, an alkyl group (such as the methyl or ethyl group) or an amino-protecting group, such as any one of those described above. Alternatively, $R^7$ and $R^8$ or $R^8$ and $R^9$ may, together with the atom or atoms to which they are attached, form a ring. In the case of $R^8$ and $R^9$ forming a ring, they preferably together represent an alkylene group, such as an ethylene, trimethylene, tetramethylene, pentamethylene or hexamethylene group. In the case of $R^7$ and $R^8$ forming a ring, $R^7$ and $R^8$ preferably together represent an alkylene group such as an ethylene or trimethylene group.

Where $R^4$ represents an aryl-substituted alkyl group, i.e. an aralkyl group, it is preferably a benzyl, p-methoxybenzyl, m-nitrobenzyl, o-methylbenzyl, p-bromobenzyl or p-aminobenzyl group.

Where $R^4$ represents an alkyl group having an aromatic heterocyclic substituent, the aromatic heterocyclic system is preferably a 5- or 6-membered aromatic heterocyclic ring containing an oxygen, sulphur or nitrogen atom, for example a thienyl or furyl ring, and the alkyl group may be a straight or branched chain group, preferably having 1 or 2 carbon atoms and more preferably being a methyl group. Examples of such substituted alkyl groups include the 2-thenyl, 3-thenyl and furfuryl groups.

Where $R^4$ represents an alkyl group having an alicyclic heterocyclic substituent, the alkyl group is preferably a $C_1$–$C_4$ alkyl group, for example a methyl, 1-substituted ethyl, 2-substituted ethyl or 1-substituted propyl group, and the alicyclic heterocyclic moiety may be any one of those hereinbefore referred to where $R^4$ represents an alicyclic heterocyclic moiety; this moiety may be unsubstituted or may have one or more substitutents attached to the ring carbon and/or nitrogen atoms as defined above.

Alternatively, $R^4$ may represent an aromatic heterocyclic group, such as the pyridyl, pyrimidinyl, triazinyl, thienyl, furyl, thiazolyl or imidazolyl groups, which may optionally be substituted with one or more groups such as the following: alkyl groups, such as the methyl, ethyl or propyl groups; alkoxy groups, such as the methoxy, ethoxy or propoxy groups; the amino group; alkylamino groups, such as the methylamino, ethylamino or propylamino groups; dialkylamino groups, such as the dimethylamino or diethylamino groups; the hydroxy group; $C_1$–$C_4$ alkanoyloxy groups, such as the acetoxy or propionyloxy groups; the nitro group; halogen atoms, such as the fluorine, chlorine or bromine atoms; or alkoxycarbonyl groups; such as the methoxycarbonyl, p-nitrobenzyloxycarbonyl or t-butyloxycarbonyl group.

When $R^4$ represents an aryl group, it is preferably a phenyl or naphthyl (e.g. 1-naphthyl or 2-naphthyl) group, which may be unsubstituted or may have one or more substituents, e.g. selected from the following: halogen atoms, such as chlorine, fluorine, bromine or iodine atoms; $C_1$–$C_6$ alkyl groups, such as the methyl, ethyl, propyl, isopropyl, butyl, t-butyl, pentyl, isopentyl or hexyl groups; $C_1$–$C_6$ alkoxy groups, such as the methoxy, ethoxy, propoxy, isopropoxy, butoxy or t-butoxy groups: the nitro group: the cyano group; the amino group; or mono- or di-alkylamino groups, such as the methylamino, ethylamino, propylamino, isopropylamino, dimethylamino, diethylamino, dipropylamino, diisopropylamino, dibutylamino or methylethylamino groups. Where two or more substituents are present, these may be the same or different.

When $R^4$ represents an alkenyl group or a substituted alkenyl group, it is preferably a vinyl, allyl, 1-propenyl or 2-butenyl group, which may be substituted or unsubstituted.

When $R^4$ represents an alkynyl group or a substituted alkynyl group, it is preferably an ethynyl, 2-propynyl or 1-propynyl group, which may be substituted or unsubstituted.

Where $R^4$ represents a substituted alkenyl or alkynyl group, examples of possible substituents are: groups of formula -$NR^{16}R^{17}$, in which $R^{16}$ and $R^{17}$ are the same or different and each represents a hydrogen atom, an alkyl group (e.g. a methyl, ethyl, propyl or isopropyl group), an acyl group (e.g. a formyl, acetyl, propionyl, isobutyryl, chloroacetyl, trifluoroacetyl or benzoyl group) or another amino-protecting group (such as: an optionally substituted alkoxycarbonyl group, e.g. ethoxycarbonyl, t-butoxycarbonyl, 2,2,2-trichloroethoxycarbonyl, 2,2,2-tribromoethoxycarbonyl, 2-(trimethylsilyl) ethoxycarbonyl, benzyloxycarbonyl, p-nitrobenzyloxycarbonyl or o-nitrobenzyloxycarbonyl; an allyloxycarbonyl group; or an aralkyl group, e.g. benzyl, diphenylmethyl or triphenylmethyl); groups of formula —$CONHR^{18}$, in which $R^{18}$ represents a hydrogen atom, an alkyl group (e.g. a methyl, ethyl or propyl group) or an amino-protecting group (e.g. the acyl groups or amino-protecting groups exemplified above for $R^{16}$ and $R^{17}$); groups of formula —$NHCONHR^{18}$, in which $R^{18}$ is as defined above; groups of formula —$COOR^{19}$, in which $R^{19}$ represents a hydrogen atom, an alkyl group (e.g. a methyl, ethyl or propyl group) or a carboxy-protecting group (examples of which are given hereafter for $R^5$); groups of formula —$SR^{20}$, in which $R^{20}$ represents a hydrogen atom, an alkyl group (e.g. a methyl, ethyl or propyl group), an alkenyl group (e.g. an allyl, vinyl, 1-methylvinyl or 1-propenyl group), an alkynyl group (e.g. an ethynyl, 2-propynyl or 1-propynyl group), a cycloalkyl group (e.g. a cyclopropyl, cyclopentyl or cyclohexyl group), a cycloalkylalkyl group (e.g. a cyclopropylmethyl, cyclopentylmethyl, 2-cyclohexylethyl or 2-cyclopentylethyl group), an aralkyl group (e.g. a benzyl, phenethyl, p-methoxybenzyl or p-bromobenzyl group), an aryl group (e.g. a phenyl, p-tolyl or p-methoxyphenyl group), an aromatic heterocyclic group (e.g. a thienyl, furyl, imidazolyl or pyridyl group), or an alkyl group having an aromatic heterocyclic substituent (e.g. a thienylmethyl, 2-thienylethyl, pyridylmethyl, imidazolylmethyl or thiazolylmethyl group); groups of formula —$S(:O)R^{20}$ (in which $R^{20}$ is as defined above); groups of formula —$SO_2R^{21}$ (in which $R^{21}$ represents any of the groups defined for $R^{20}$ or an alkoxy group, e.g. a methoxy, ethoxy or propoxy group); groups of formula —$OSO_2R^{20}$ (in which $R^{20}$ is as defined above); cyano groups; nitro groups; or azido groups.

$R^5$ may represent a hydrogen atom or a carboxy-protecting group. There is no particular limitation on the nature of the carboxy-protecting group employed, as it will normally and preferably be removed after completion of the reaction sequence of the present invention. Accordingly, any protecting group commonly used in the field of β-lactam antibiotics may be employed. Examples of suitable protecting groups include: $C_1$–$C_6$ alkyl groups, such as the methyl, ethyl or t-butyl groups; aralkyl groups, such as the benzyl, diphenylmethyl, p-nitrobenzyl or o-nitrobenzyl groups; alkenyl or substituted alkenyl groups, such as the allyl, 2-chloroallyl or 2-methylallyl groups; haloalkyl groups, such as the 2,2,2-chloroethyl or 2,2,2-tribromoethyl groups; the 2-trimethylsilylethyl group; or the t-butylcarbonyloxymethyl group.

Where $R^6$ represents an alkoxy group, this is preferably a group having from 1 to 6 carbon atoms and may be a straight or branched chain group, for example the methoxy, ethoxy, propoxy, isopropoxy, butoxy or sec-butoxy groups. Where $R^6$ represents an aryloxy group, this is preferably a phenoxy group, which may be substituted or unsubstituted and examples include the phenoxy, p-methylphenoxy or p-methoxyphenoxy groups. Where $R^6$ represents a dialkylamino group, each alkyl group, which may be a straight or branched chain group, preferably has from 1 to 6 carbon atoms and examples include the dimethylamino, diethylamino, dipropylamino, diisopropylamino, dibutylamino, di-sec-butylamino, di-t-butylamino or dipentylamino groups.

Two of the symbols $R^6$ may together represent an o-phenylenedioxy group, whilst the other may be any of the groups suggested above. Alternatively, the three symbols $R^6$ together may represent a group of formula $CH_3$—$(CH_2$—$O$—$)_3$.

Particularly preferred compounds of formula (I) of the present invention are those compounds in which:

$R^1$ represents a hydrogen atom, a trimethylsilyl, t-butyldimethylsilyl, p-nitrobenzyl, p-nitrobenzyloxycarbonyl, allyloxycarbonyl, 2,2,2-tribromoethoxycarbonyl, 1-ethoxyethyl or chloroacetyl group;

$R^2$ and $R^3$ both represent hydrogen atoms;

$R^4$ represents: an alkyl group (such as the methyl, ethyl or t-butyl group); a protected hydroxyalkyl group (such as a protected 2-hydroxyethyl or protected 2-hydroxy-1-methylethyl group); a protected amrinoalkyl groups such as a protected 2-aminoethyl, protected 2-amino-1-methylethyl, protected 2-(2-aminoethoxy)ethyl or protected 2-(2-aminoethoxy)-1-methylethyl group; an $N^1$, $N^1$, $N^2$-trimethyl-amidinomethyl group; the benzyl group; an aryl group, such as the phenyl or 2-naphthyl group; an alicyclic heterocyclic group, such as the 1-(p-nitrobenzyloxycarbonyl)-pyrrolidin-3-yl, 1-acetylpyrrolidin-3-yl, 1-[N-(p-nitrobenzyloxycarbonyl) acetimidoyl ]pyrrolidin-3-yl, 1-(N-methylacetimidoyl) pyrrolidin-3-yl, 1-[N-(p-nitrobenzyloxycarbonyl) formimidoyl]pyrrolidin-3-yl, 1-(N-methylformimidoyl) pyrrolidin-3-yl, 2-oxo-5-hexa-hydropyrimidinyl, 3,4,5,6-tetrahydro-2-methyl-pyrimidin-5-yl or 1,4,5,6-tetrahydro-2-methyl-1-(p-nitrobenzyloxycarbonyl) pyrimidin-5-yl group; an alkyl group having an aliphatic heterocyclic substituent, such as the 1-[1-(p-nitrobenzyloxycarbonyl) pyrrolidin-3-yl] ethyl, 1-(1-acetylpyrrolidin-3-yl) ethyl. 1-(1-[N-(p-nitrobenzyloxycarbonyl) formimidoyl]pyrrolidin-3-yl) ethyl, 1-(1-[N-(p-nitrobenzyloxycarbonyl) acetimidoyl] pyrrolidin3-yl) ethyl, 1-(4-[N-(p-nitrobenzyloxycarbonyl)-formimidoyl]morpholin-2-yl)-ethyl, 1-(4-[N-(p-nitrobenzyloxycarbonyl) acetimidoyl]morpholin-2-yl)ethyl, 1-[4-(p-nitroberzyloxycarbonyl)-morpholin-2-yl]ethyl, 1-(4-acetylmorpholin-2-yl)ethyl or 2-[(N-p-nitrobenzyloxycarbonyl (formimidoyl) amino]ethyl groups; and aromatic heterocyclic groups, such as the 2-pyridyl, 3-pyridyl, 4-pyridyl, 2-thienyl, 3-thienyl, 2-furyl, 3-furyl, 1,2,4-triazol-3-yl or 2-thiazolyl groups;

$R^5$ represents a hydrogen atom or a carboxyprotecting group, such as the methyl, t-butyl, benzyl, diphenylmethyl, p-nitrobenzyl, o-nitrobenzyl, allyl, 2-chloroallyl, 2,2,2-trichloroethyl, 2,2,2-tribromoethyl or 2-trimethylsilylethyl groups; and $R^6$ represents: an alkoxy group, such as the methoxy, ethoxy, propoxy, isopropoxy, butoxy or sec-butoxy groups; an aryloxy group, such as the phenoxy, p-tolyloxy or p-methoxyphenoxy groups; or a dialkylamino group, in which each alkyl group is a straight or branched chain group having from 1 to 4 carbon atoms, such as the dimethylamino, diethylamino, dipropylamino, diisopropylamino, dibutylamino, di-sec-butylamino or di-t-butylamino groups.

Examples of compounds of formula (I) of the present invention are given in the following list:

1. 3-(1-t-butyldimethylsilyloxyethyl)-4-(methylthio) carbonylmethyl-1-[1-(p-nitrobenzyloxycarbonyl)-1-tripropoxyphosphoranylidenemethyl]-2-azetidinone
2. 4-[1-(t-butylthio)carbonylethyl]-3-(1-p-nitrobenzyloxycarbonyloxyethyl)-1-[1-(o-nitrobenzyloxycarbonyl)-1-triethoxyphosphoranylidenemethyl]-2-azetidinone
3. 3-(1-chloroacetoxyethyl)-1-[1-(p-nitrobenzyloxycarbonyl)-1-triisopropoxyphosphoranylidenemethyl]-4-(phenylthio)carbonylmethyl-2-azetidinone
4. 3-(1-p-nitrobenzyloxyethyl)-1-[1-(p-nitrobenzyloxycarbonyl)-1-triphenoxyphosphoranylidenemethyl]-4-(2-p-nitrobenzyloxycarbonyloxyethylthio)carbonylmethyl-2-azetidinone
5. 4-(2-t-butyldimethylsilyloxy-1-methylethyl)-3-(1-p-nitrobenzyloxycarbonyloxyethyl)-1-[1-(p-nitrobenzyloxycarbonyl)-1-tripropoxyphosphoranylidenemethyl]-2-azetidinone
6. 1-(1-methallyloxycarbonyl-1-triphenoxyphosphoranylidenemethyl)-3-(1-o-nitrobenzyloxycarbonyloxyethyl)-4-(2-p-nitrobenzyloxycarbonylaminoethylthio) carbonylmethyl-2-azetidinone
7. 3-[1-(2-chloroallyloxycarbonyloxy) ethyl]-4-[1-methyl-2-(2,2,2-tribromoethoxycarbonylamino) ethylthio] carbonyl-methyl-1-(1-p-nitrobenzyloxycarbonyl)-1-tributoxyphosphoranylidenemethyl)-2-azetidinone
8. 1-(1-benzhydryloxycarbonyl-1-triethoxyphosphoranylidenemethyl)-3-(1-p-nitrobenzyloxyethyl)-4-[2-(2-p-nitrobenzyloxycarbonylaminoethoxy) ethylthio] carbonylmethyl-2-azetidinone
9. 3-(1-p-nitrobenzyloxycarbonyloxyethyl)-1-(1-p-nitrobenzyloxycarbonyl-1-triethoxyphosphoranylidenemethyl)-4-[($N^1$, $N^1$, $N^2$-trimethylamidinomethylthio) carbonylmethyl]-2-azetidinone
10. 3-[1-(t-butyldimethylsilyloxy) ethyl]-4-($N^1$, $N^2$-dimethyl-$N^1$-p-nitrobenzyloxycarbonylamidinomrethylthio)-carbonylmethyl-1-(1-p-nitrobenzyloxycarbonyl-1-triethoxyphosphoranylidenemethyl)-2-azetidinone
11. 3-[1-(t-butyldimethylsilyloxy)ethyl]-4-($N^2$-ethyl-$N^1$,$N^1$-dimethylamidinomethylthio)carbonylmethyl-1-(1-p-nitrobenzyloxycarbonyl-1-triethoxyphosphoranylidenemethyl)-2-azetidinone
12. 3-[1-(t-butyldimethylsilyloxy) ethyl]-4-[2-methylimino-2-(1-pyrrolidinyl)ethylthio]carbonylmethyl-1-(1-p-nitrobenzyloxycarbonyl-1-triethoxyphosphoranylidenemethyl)-2-azetidinone
13. 3-[1-(t-butyldimethylsilyloxy)ethyl]-4-[(1-methyl-2-imidazolin-2-yl methylthio)carbonylmethyl]-1-(1-p-

14. 4-[N$^1$, N$^2$-bis(p-nitrobenzyloxycarbonyl) amidinothiocarbonylmethyl]-3-(1-p-nitrobenzyloxycarbonyloxyethyl)-1-(1-p-nitrobenzyloxycarbonyl-1-triethoxyphosphoranylidene-methyl)-2-azetidinorie
15. 3-(1-p-nitrobenzyloxycarbonyloxyethyl)-1-(1-p-nitrobenzyloxycarbonyl-1-triethoxyphosphoranylidenemethyl)-4-[2-(N$^1$, N$^1$, N$^2$-trimethylamidino) ethylthio]carbonylmethyl-2-azetidinone
16. 4-[3-(N$^1$, N$^1$-dimethyl-N$^2$-p-nitrobenzyloxycarbonyl-amidino) propylthio]carbonylmethyl-3-(1-p-nitrobenzyloxycarbonyloxyethyl)-1-(1-p-nitrobenzyloxycarbonyl-1-triethoxyphosphoranylidenemethyl)-2-azetidinone
17. 3-(1-p-nitrobenzyloxycarbonyloxyethyl)-4-[(1-p-nitrobenzyloxycarbonyl-3-pyrrolidinylthio)carbonylmethyl]-1-(p-nitrobenzyloxycarbonyl-1-triethoxyphosphoranylidenemethyl)-2-azetidinone
18. 4-[(1-acetyl-3-pyrrolidinylthio)carbonylmethyl]-3-(1-p-nitrobenzyloxycarbonyloxyethyl)-1-(l-p-nitrobenzyloxycarbonyl-1-triethoxyphosphoranylidenemethyl)-2-azetidinone
19. 4-[1-(N-p-nitrobenzyloxycarbonylacetimidoyl)-3-pyrrolidinyltlio]carbonylmethyl-1-(1-p-nitrobenzyloxycarbonyl-1-tripropoxyphosphoranylidenemethyl)-3-[1-(trimethylsilyloxy) ethyl]-2-azetidinone
20. 4-[1-(N-p-nitrobenzyloxycarbonylformimidoyl)-3-pyrrolidinylthio]carbonylmethyl-1-(1-p-nitrobenzyloxycarbonyl-1-triisopropoxyphosphoranylidenemethyl)-3-(1-p-nitrobenzyloxycarbonyloxyethyl)-2-azetidinone
21. 4-[1-(N-p-nitrobenzyloxycarbonylacetimidoyl)-3-pyrrolidinylthio]carbonylmethyl-3-(1-p-nitrobenzyloxycarbonyloxyethyl)-1-(1-p-nitrobenzyloxycarbonyl-1-triisopropoxyphosphoranylidenemethyl)-2-azetidinone
22. 4-[1-(N-methylformimidoyl)-3-pyrrolidinylthio]carbonylmethyl-3-(1-p-nitrobenzyloxycarbonyloxyethyl)-1-(1-p-nitrobenzyloxycarbonyl-1-triisopropoxyphosphoranylidenemethyl)-2-azetidinone
23. 1-(1-t-butoxycarbonyl-1-triisopropoxyphosphoranylidenemethyl)-4-(4-methoxy-1-p-nitrobenzyloxycarbonyl-3-pyrrolidinylthio)carbonylmethyl-3-(1-p-nitrobenzyloxycarbonyloxyethyl)-2-azetidinone
24. 1-(1-carboxy-1-trimethoxyphosphoranylidenemethyl)-4-(4-methylsulphonyl-1-p-nitrobenyloxycarbonyl-3-pyrrolidinylthio)carbonylmethyl-3-(1-p-nitrobenzyloxycarbonyloxyethyl)-2-azetidinone.
25. 1-(1-benzyloxycarbonyl-1-triethoxyphosphoranylidenemethyl)-4-(5-ethoxy-1-p-nitrobenzyloxycarbonyl-3-pyrrolidinylthio)carbonylmethyl-3-(1-p-nitrobenzyloxycarbonyloxyethyl)-2-azetidinone.
26. 3-(1-p-nitrobenzyloxycarbonyloxyethyl)-1-(1-p-nitrobenzyloxycarbonyl-1-triethoxyphosphoranylidenemethyl)-4-(1-p-nitrobenzyloxycarbonyl-3-piperidylthio) carbonylmethyl-2-azetidinone
27. 4-(5-methoxycarbonyl-1-p-nitrobenzyloxycarbonyl-4-piperidylthio)carbonylmethyl-3-(1-p-nitrobenzyloxycarbonyl-oxyethyl)-1-(1-p-nitrobenzyloxycarbonyl-1-triethoxyphosphoranylidenemethyl)-2-azetidinone
28. 4-(2-p-nitrobenzyloxycarbonylamino-4,5-dihydro-1,3-thiazol-5-ylthio)carbonylmethyl-3-[1-p-nitrobenzyloxycarbonyloxyethyl]- 1-(1-p-nitrobenzyloxycarbonyl-1-tris (dimethylamino)phosphoranylidenemethyl]-2-azetidinone
29. 4-(2-methyl-3,4,5,6-tetrahydro-5-pyrimidinylthio)-carbonylmethyl-3-(1-p-nitrobenzyloxycarbonyloxyethyl)-1-(1-p-nitrobenzyloxycarbonyl-1-triethoxyphosphoranylidenemethyl)-2-azetidinone
30. 4-(2-methoxymethyl-1-p-nitrobenzyloxycarbonyl-1,4,5,6-tetrahydro-5-pyrimidinylthio)carbonylmethyl-1-(p-nitrobenzyloxycarbonyl-1-triethoxyphosphoranylidenemethyl)-2-azetidinone
31. 4-(2-methoxycarbonylmethyl-1-p-nitrobenzyloxycarbonyl-1,4,5,6-tetrahydro-5-pyrimidinylthio)carbonylmethyl-1-(p-nitrobenzyloxycarbonyl-1-triethoxyphosphoranylidenemethyl)-2-azetidinone
32. 4-[1-(4-p-nitrobenzyloxycarbonyl-2-morpholinyl) ethylthio]carbonylmethyl-3-(1-p-nitrobenzyloxycarbonyloxyethyl)-1-(1-p-nitrobenzyloxycarbonyl-1-tripropoxy-phosphoranylidenemethyl)-2-azetidinone
33. 4-[1-(4-acetyl-2-morpholinyl) ethylthio]carbonylmethyl-3-(1-p-nitrobenzyloxycarbonyloxyethyl)-1-(1-p-nitrobenzyloxycarbonyl-1-tripropoxyphosphoranylidenemethyl)-2-azetidinone
34. 4-(1-[4-(N-p-nitrobenzyloxycarbonylacetimidoyl)-2-morpholinyl]ethylthio)carbonylmethyl-3-(1-p-nitrobenzyloxycarbonyloxyethyl)-1-(1-p-nitrobenzyloxycarbonyl-1-tripropoxyphosphoranylidenemnethyl)-2-azetidinone
35. 3-(1-t-butyldimethylsilyloxyethyl)-4-(1-[4-(N-p-nitrobenzyloxycarbonylformimidoyl)-3-piperidyl]ethylthio)-carbonylmethyl-1-(1-p-nitrobenzyloxycarbonyl-1-tripropoxyphosphoranylidenemethyl )-2-azetidinone
36. 3-(1-t-butyldimethylsilyloxyethyl)-4-[1-(1-p-nitrobenzyloxycarbonyl-3-pyrrolidinyl)ethylthio]carbonylmethyl-1-[1-p-nitrobenzyloxycarbonyl-1-tris(dipropylamino)-phosphoranylidenemethyl]-2-azetidinone
37. 4-[1-(1-acetyl-3-pyrrolidinyl) ethylthio]carbonylmethy-3-(1-t-butyldimethylsilyloxethyl)-1-1-p-nitrobenzyloxycarbonyl-1-triethoxyphosphoranylidenemethyl)-2-azetidinone
38. 3-(1-t-butyldimethylsilyloxyethyl)-4-(1-[N-p-nitrobenzyloxycarbonylformimidoyl)-3-pyrrolidinyl]ethylthio)-carbonylmethyl-1-(1-p-nitrobenzyloxycarbonyl-1-triethoxyphosphoranylidenemethyl)-2-azetidinone
39. 3-(1-t-butyldimethylsilyloxyethyl)-4-(1-[1-(N-p-nitrobenzyloxycarbonylacetimidoyl)-3-pyrrolidinyl]ethylthio)-carbonylmethyl-1-[1-p-nitrobenzyloxycarbonyl-1-tris-(dibutylamino)phosphoranylidenemethyl]-2-azetidinone
40. 3-(1-t-butyldimethylsilyloxyethyl)-1-(1-p-nitrobenzyloxycarbonyl-1-triisopropoxyphosphoranylidenemethyl)-4-(2-pyridylthio)carbonylmethyl-2-azetidinone
41. 3-(1-t-butyldimethylsilyloxyethyl)-1-(1-carboxy-1-triisopropoxyphosphoranylidenemethyl)-4-(3-pyridylthio)-carbonylmethyl-2-azetidinone
42. 3-(1-t-butyldimethylsilyloxyethyl)-1-(1-p-nitrobenzyloxycarbonyl-1-triisopropoxyphosphoranylidenemethyl)-4-(4-pyridylthio)carbonylmethyl-2-azetidinone
43. 3-(1-t-butyldimethylsilyloxyethyl)-1-(1-,p-nitrobenzyloxycarbonyl-1-triisopropoxyphosphoranylidenemethyl)-4-(2-thienylthio)carbonylmethyl-2-azetidinone
44. 3-(1-t-butyldimethylsilyloxyethyl)-1-(1-p-nitrobenzyloxycarbonyl-1-triisopropoxyphosphoranylidenemethyl)-4-(4-nitro-2-furylthio) carbonylmethyl-2-azetidinone
45. 3-(1-p-nitrobenzyloxycarbonyloxyethyl)-1-(1-p-nitrobenzyloxycarbonyl-1-triethoxyphosphoranylidenemethyl)-4-[1-(2-(1,3,5-triazinyl) thio) carbonylmethyl1]-2-azetidinone 46. 4-(2-p-nitrobenzyloxycarbonylamino-4-imidazolylthio)-carbonylmethyl-3-(1-p-nitrobenzyloxycarbonyloxyethyl)-1-(1-p-nitrobenzyloxycarbonyl-1-triethoxyphosphoranylidenemethyl)-2-azetidinone 47. 4-(2-methoxy-5-pyrimidinylthio)carbonylmethyl-3-(1-p-nitrobenzyloxycarbonyloxyethyl)-1-(1-p-nitrobenzyloxycarbonyl-1-triethoxyphosphoranylidenemethyl)-2-azetidinone 48. 4-[1-(N-p-nitrobenzyloxycarbonylacetimidoyl)-3-pyrrolidinylthio]carbonylmethyl-1-(1-p-nitrobenzyloxycarbonyl-1-triethoxyphosphoranylidenemethyl1)-3-(1-p-nitrobenzyloxycarbonyloxyethyl)-2-azetidinone 49. 3-(1-p-nitrobenzyloxycarbonyloxyethyl)-1-(1-p-nitrobenzyloxycarbonyl-1-triisopropoxyphosphoranylidenemethyl)-4-(2-oxo-5-hexahydropyrimidinylthio) carbonylmethyl-2-azetidinone 50. 4-(2-[(N-p-nitrobenzyloxycarbonylformimidoyl) amino]-ethylthio)carbonylmethyl-1-(1-p-nitrobenzyloxycarbonyl-1-triethoxyphosphoranylidenemethyl)-3-(1-p-nitrobenzyloxycarbonyloxyethyl)-2-azetidinone.

Preferred compounds of formula (IV) are those in which:

$R^1$ represents a hydrogen atom or a trimethylsilyl, t-butyldimethylsilyl, p-nitrobenzyl, p-nitrobenzyloxycarbonyl, allyloxycarbonyl, 2,2,2-tribromoethoxycarbonyl, 1-ethoxyethyl or chloroacetyl group;

$R^2$ and $R^3$ both represent hydrogen atoms;

$R^4$ represents: an alkyl group (such as the methyl, ethyl or t-butyl group); a protected hydroxyalkyl group (such as a protected 2-hydroxyethyl or protected 2-hydroxy-1-methylethyl group; a protected aminoalkyl group, such as a protected 2-aminoethyl, protected 2-amino-1-methylethyl, protected 2-(2-aminoethoxy)ethyl or protected 2-(2-aminoethoxy)-1-methylethyl group; an $N^1$, $N^1$, $N^2$-trimethylamidinomethyl group; the benzyl group; an aryl group, such as the phenyl or 2-naphthyl group; an alicyclic heterocyclic group, such as the 1-(p-nitrobenzyloxycarbonyl)-pyrrolidin-3-yl, 1-acetylpyrrolidin-3-yl, 1-[N-(p-nitrobenzyloxycarbonyl) acetimidoyl]pyrrolidin-3-yl,1-methylactimidoyl)pyrrolidin-3-yl, 1-[N-(,-nitrobenzyloxycarbonyl) formimidoyl] pyrrolidin-3-yl, 1-(N-methylformimidoyl)pyrrolidin-3-yl, 2-oxo-hexahydropyrimidin-5-yl, 3,4,5,6-tetrahydro-2-methyl-pyrimidin-5-yl or 1,4,5,6-tetrahydro-2-methyl-1-(p-nitrobenzyloxycarbonyl) pyrimidin-5-yl group; an alkyl group having an aliphatic heterocyclic substituent, such as the 1-[1-(p-nitrobenzyloxycarbonyl) pyrrolidin-3-yl]ethyl, 1-(1-acetylpyrrolidin-3-yl) ethyl, 1-(1-[N-(p-nitrobenzyloxycarbonyl)-formimidoyl]pyrrolidin-3-yl) ethyl, 1-(1-[N-(p-nitrobenzyloxycarbonyl) acetimidoyl]morpholin-3-yl)ethyl, 1-(4-[N-(p-nitrobenzyloxycarbonyl) formimidoyl]morpholin-2-yl) ethyl, 1-(4-[N-(p-nitrobenzyloxycarbonyl)-acetimidoyl]morpholin-2-yl)ethyl, 1-[4-(p-nitrobenzyloxycarbonyl) morpholin-2-yl]ethyl, 1-(4-acetylmorpholin-2-yl)ethyl or 2-[(N-p-nitrobenzyloxycarbonylformimidoyl) amino]ethyl groups; and aromatic heterocyclic groups, such as the 2-pyridyl, 3-pyridyl, 4-pyridyl, 2-thienyl, 3-thienyl, 2-furyl, 3-furyl, 1,2,4-triazol-3-yl or 2-thiazolyl groups; and $R^5$ represents a hydrogen atom or a carboxy-protecting group, such as the methyl, t-butyl, benzyl, diphenylmethyl, p-nitrobenzyl, o-nitrobenzyl, allyl, 2-chloroallyl, 2,2,2-trichloroethyl, 2,2,2-tribromoethyl or 2-trimethylsilylethyl groups.

Examples of compounds of formula (IV) are those compounds specifically derivable by the process of the invention from the compounds of formula (I) listed above. In particular, the following compounds of formula (IV) are of a special interest.

51. t-butyl 6-(1-t-butyldimethylsilyloxyethyl)-2-methyl-thiocarbapen-2-em-3-carboxylate 52. p-nitrobenzyl 6-(1-t-butyldimethylsilyloxyethyl)-2-methylthiocarbapen-2-em-3-carboxylate 53. Benzhydryl 2-t-butylthio-6-(1-p-nitrobenzyloxyethyl)-carbapen-2-em-3-carboxylate 54. o-nitrobenzyl 2-t-butylthio-1-methyl-6-(p-nitrobenzyloxycarbonyloxyethyl) carbapen-2-em-3-carboxylate 55. 2,2,2-trichloroethyl 6-(1-allyloxycarbonyloxyethyl)-2-t-butylthio-1,1-dimethylcarbapen-2-em-3-carboxylate 56. p-nitrobenzyl 2-benzylthio-6-[1-(2,2, 2-trichloroethoxycarbonyloxy)ethyl]carbapen-2-em-3-carboxylate 57. 2-methyl-2-propenyl 2-benzylthio-6-[(1-(1-ethoxyethoxy) ethyl]carbapen-2-em-3-carboxylate 58. 2-trimethylsilylethyl 6-(1-o-nitrobenzyloxycarbonyloxyethyl)-2-phenylthiocarbapen-2-em-3-carboxylate 59. p-nitrobenzyl 6-(1-chloroacetoxyethyl)-2-($N^1,N^1,N^2$-trimethylamidinomethylthio)carbapen-2-em-3-carboxylate 60. p-nitrobenzyl 2-(2-p-nitrobenzyloxycarbonyloxyethylthio)-6-(1-p-nitrobenzyloxyethyl) carbapen-2-em-3-carboxylate 61. p-nitrobenzyl 2-(2-t-butyldimethylsilyloxy-1-methylethylthio)-6-(1-p-nitrobenzyloxycarbonyloxyethyl) carbapen-2-em-3-carboxylate 62. 2-methyl-2-propenyl 2-(2-p-nitrobenzyloxycarbonylaminoethylthio)-6-(1-o-nitrobenzyloxycarbonyloxyethyl)-carbapen-2-em-3-carboxylate 63. p-nitrobenzyl 6-[(1-(2-chloroallyloxycarbonyloxyethyl)]-2-[2-(2,2,2-tribromoethoxycarbonylamino)-1-methylethylthio]carbapen-2-em-3-carboxylate 64. Benzhydryl 2-[2-(p-nitrobenzyloxycarbonylaminoetioxy) ethylthio]-6-(1-p-nitrobenzyloxycarbonyloxyethyl)-carbapen-2-em-3-carboxylate 65. p-nitrobenzyl 6-(1-p-nitrobenzyloxycarbonyloxyethyl)-2-(1-p-nitrobenzyloxycarbonyl-3-pyrrolidinylthio) carbapen-2-em-3-carboxylate 66. p-nitrobenzyl 2-(1-acetyl-3-pyrrolidinylthio)-6-(1-p-nitrobenzyloxycarbonyloxyethyl) carbapen-2-em-3-carboxylate 67. p-nitrobenzyl 2-[1-(N-p-nitrobenzyloxycarbonylacetimidoyl)- 3-pyrrolidinylthio]-6-(1-trimetaylsilyloxyethyl) carbapen-2-em-3-carboxylate 68. 6-(1-hydroxyethyl)-2-(i-acetimidoyl-3-pyrrolidinylthio) carbapen-2-em-3-carboxylic acid 69. p-nitrobenzyl 2-[1-(N-p-nitrobenzyloxycarbonyl-formimidoyl)-3-pyrrolidinylthio]-6-(1-p-nitrobenzyloxycarbonyloxyethyl) carbapen-2-em-3-carboxylate 70. t-butyl 2-[(1-(N-methylacetimidoyl)-3-pyrrolidinylthio]-6-(1-p-nitrobenzyloxycarbonyloxyethyl) carbapen-2-em-3-carboxylate 71. 6-(1-hydroxyethyl)-2-[1-(N-methylacetimidoyl)-3-pyrrolidinylthio]carbapen-2-em-3-carboxylic acid 72. 2-(4-methylsulphonyl-1-p-nitrobenzyloxycarbonyl-3-pyrrolidinylthio)-6-(1-p-nitrobenzyloxycarbonyloxyethyl)-carbapen-2-em-3-carboxylic acid 73. Benzyl 2-(2-ethoxy-1-p-nitrobenzyloxycarbonyl-4-pyrrolidinylthio)-6-(1-p-nltrobenzyloxycarbonyloxyethyl)-carbapen-2-em-3-carboxylate 74. p-nitrobenzyl 6-(1-p-nitrobenzyloxycarbonyloxyethyl)-2-(1-p-nitrobenzyloxycarbonyl-3-piperidylthio)carbapen-2-em-3-carboxylate 75. p-nitrobenzyl 2-(3-methoxycarbonyl-1-p-nitrobenzyloxycarbonyl-4-piperidylthio)-6-(1-p-nitrobenzyloxycarbonyloxyethyl) carbapen-2-em-3-carboxylate
76. p-nitrobenzyl 2-(2-p-nitrobenzyloxycarbonylamino-4,5-dihydro-thiazol-5-ylthio)-6-(1-p-nitrobenzyloxy-carbonyloxyethyl) carbapen-2-em-3-carboxylate
77. p-nitrobenzyl 2-(2-methyl-3,4,5,6-tetrahydro-5-pyrimidinylthio)-6-(1-p-nitrobenzyloxycarbonyl-oxyethyl)-carbapen-2-em-3-carboxylate
78. p-nitrobenzyl 2-(2-methoxymethyl-1-p-nitrobenzyloxycarbonyl-1,4,5,6-tetrahydro-5-pyrimidinylthio)-6-(1-p-nitrobenzyloxycarbonyl-oxyethyl)carbapen-2-em-3-carboxylate
79. p-nitrobenzyl 2-(2-methoxycarbonylmethyl-1-p-nitrobenzyloxycarbonyl-1,4,5,6-tetrahydro-5-pyrimidinylthio)-6-(1-p-nitrobenzyloxy-carbonyloxyethyl)carbapen-2-em-3-carboxylate
80. p-nitrobenzyl 2-[1-(4-p-nitrobenzyloxycarbonyl-2-morpholinyl)ethylthio]-6-(1-p-nitrobenzyloxycarbonyl-oxyethyl) carbapen-2-em-3-carboxylate
81. p-nitrobenzyl 2-[1-(4-acetyl-2-morpholinyl) ethylthio]-6-(1-p-nitrobenzyloxycarbonyloxyethyl) carbapen-2-em-3-carboxylate
82. p-nitrobenzyl 2-(1-[4-(N-p-nitrobenzyloxy-carbonylacetimidoyl)-2-morpholinyl]ethylthio)-6-(1-p-nitrobenzyloxycarbonyloxyethyl) carbapen-2-em-3-carboxylate
83. p-nitrobenzyl 6-(1-t-butyldimethylsilyloxyethyl)-2-(1-[1-(N-p-nitrobenzyloxycarbonylformimidoyl)-3-piperidyl]-ethylthio)carbapen-2-em-3-carboxylate
84. p-nitrobenzyl 6-(1-t-butyldimethylsilyloxyethyl)-2-[1-(1-p-nitrobenzyloxycarbonyl-3-pyrrolidinyl)ethylthio]-carbapen-2-em-3-carboxylate
85. p-nitrobenzyl 6-(1-t-butyldimethylsilyloxyethyl)-2-[1-(1-acetyl-3-pyrrolidinyl)ethylthio]carbapen-2-em-3-carboxylate
86. p-nitrobenzyl 6-(1-t-butydimethylsilyloxyethyl)-2-[1-1-(N-p-nitrobenzyloxycarbonylformimidoyl)-3-pyrrolidinyl]ethylthio)carbapen-2-em-3-carboxylate
87. p-nitrobenzyl 6-(1-t-butyldimethylsilyloxyethyl)-2-(1-[1-(N-p-nitrobenzyloxycarbonylacetimidoyl)-3-pyrrolidinyl]ethylthio)carbapen-2-em-3-carboxylate
88. p-nitrobenzyl 6-(1-t-butyldimethylsilyloxyethyl)-2-(2-pyridylthio)carbapen-2-em-3-carboxylate
89. p-nitrobenzyl 6-(1-t-butyldimethylsilyloxyethyl)-2-(3-pyridylthio)carbapen-2-em-3-carboxylate
90. p-nitrobenzyl 6-(1-t-butyldimethylsilyloxyethyl)-2 (4-pyridylthio)carbapen-2-em-3-carboxylate
91. p-nitrobenzyl 6-(1-t-butyldimethylsilyloxyethyl)-2-(2-thienylthio)carbapen-2-em-3-carboxylate
92. p-nitrobenzyl 6-(1-t-butyldimethylsilyloxyethyl)-2-(4-nitro-2-furylthio)carbapen-2-em-3-carboxylate
93. p-nitrobenzyl 1-1-methyl-6-(1-p-nitrobenzyloxy-carbonyloxyethyl)-2-(2-(1,3,5-triazinyl)thio)carbapen-em-3-carboxylate
94. p-nitrobenzyl 2-(2-p-nitrobenzyloxycarbonylamino-4-imidazolylthio)-6-(1-p-nitrobenzyloxycarbonyloxyethyl)-carbapen-2-em-3-carboxylate
95. p-nitrobenzyl 2-(2-methoxy-5-pyrimidinylthio)-6-(1-p-nitrobenzyloxycarbonyloxyethyl)carbapen-2-em-3-carboxylate
96. p-nitrobenzyl 2-(2-[(N-p-nitrobenzyloxycarbonyl-formimidoyl) amino]ethylthio)-6-(1-p-nitrobenzyl-oxycarbonyloxyethyl)-carbapen-2-em-3-carboxylate
97. p-nitrobenzyl 2-(2-oxo-5-hexahydropyrimidinylthio)-6-(1-p-nitrobenzyloxycarbonyloxyethyl)carbapen-2-em-3-carboxylate
98. p-nitrobenzyl 2-(2-acetamidovinylthio)-6-[1-(p-nitrobenzyloxycarbonyloxy)ethyl]carbapen-2-em-3-carboxylate There is no particular limitation on the stereochemistry of the compounds of formulae (I), (II) and (IV), although we prefer that they should have the same steric configuration as that of thienamycin. If there are asymmetric carbon atoms in the groups represented by $R^4$, then individual isomers or mixtures thereof may be employed.

The compounds of formula (I):

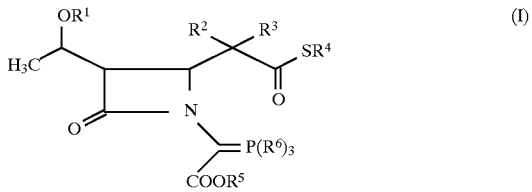

may be prepared by reacting a compound of formula (II):

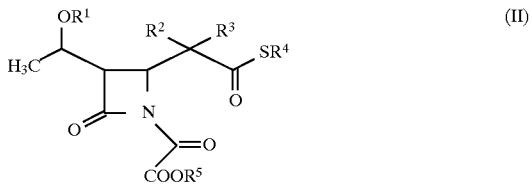

with a phosphorus compound of formula (III):

(in the above formulae, $R^1$–$R^6$ are as defined above).

Suitable trivalent organophosphorus compounds of formula (III) for use in the process of the present invention are cyclic and/or acyclic trialkyl phosphites, triaryl phosphites, mixed alkylaryl phosphites or phosphorus amides. Particularly preferred are trialkyl phosphites, of which triethyl phosphite, tripropyl phosphite and triisopropyl phosphite are the most preferred.

Examples of suitable aryl and mixed alkylaryl phosphites include: triphenyl phosphite; catechol phosphites, e.g. compounds of formula (V):

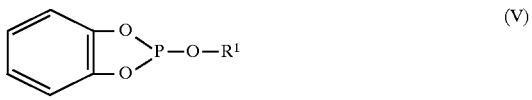

in which R' represents an alkyl group (e.g. the methyl or ethyl group) or an aryl group (e.g. the phenyl group); and catechol dimer phosphites, e.g. compounds of formula (VI):

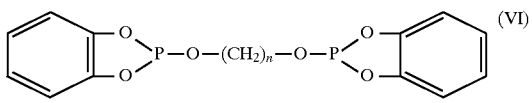

in which n is an integer, preferably 2.

A suitable cyclic phosphite is the compound of formula (VII):

Suitable phosphorus amides are those compounds of formula (VIII):

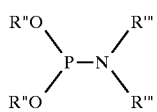

(VIII)

in which R" and R'" are the same or different and each represents an alkyl group (e.g. the methyl or ethyl group) or an aryl group (e.g. the phenyl group); the two groups represented by R" may be the same or different, although they are preferably the same and similarly the two groups represented by R'" may be the same or different, although they are preferably the same.

The reaction is preferably effected in an aprotic solvent, preferably: an aliphatic or aromatic hydrocarbon, such as hexane, benzene, toluene or xylene; a halogenated hydrocarbon, such as chloroform, methylene chloride or 1,2-dichloroethane; an ester, such as ethyl acetate; an ether, such as tetrahydrofuran or dioxane; acetonitrile; or dimethylformamide.

The reaction of compounds (II) and (III) is preferably effected with heating, for example at a temperature within the range from 50° to 150° C., for a period of, for example, from 1 to 10 hours. At the end of this time, the solvent and other volatile substances are distilled off under reduced pressure, giving the desired compound of formula (I). Depending upon the reaction temperature and time allowed for the reaction, the compound of formula (I) may have already undergone cyclisation to convert some or all of that compound into the compound of formula (IV). Thus, if the mixture of the compounds of formulae (II) and (III) is kept at a temperature within the range of from 80° to 150° C. for a period of from 10 hours to 5 days, without isolation of the compound of formula (I), the compound (IV) is obtained directly. This is an advantage of the process of the invention, as it enables the desired final product, the compound of formula (IV), to be obtained with fewer reaction steps and purification and/or separation steps, thus enabling higher yields to be achieved.

However, where the compound of formula (I) has been prepared and isolated, on heating a solution of the compound in, for example, one of the aprotic solvents illustrated above, at a temperature of from 80° to 150° C. for a period of from 10 hours to 5 days, the compound of formula (IV) is obtained.

Following preparation of the compounds of formulae (I) and/or (IV), the desired compound may be separated, preferably simply by distilling off the solvent and any other volatile matter under reduced pressure, after which it may, if necessary, be further purified by a variety of conventional techniques, such as recrystallisation, column chromatography or preparative thin layer chromatography.

The ease with which the two preparative processes of the present invention take place is wholly unexpected. Thus, a compound similar to those of formula (I) but in which $R^6$ represents a phenyl group can be prepared by the procedure of Woodward et al [ J. Chem. Soc., 101, 6301 (1979)], for example as described by Kametani et al [J. C. S. Perkin 1, 964 (1981)], but cyclisation will only proceed if $R^4$ is an electron-attracting group and proceeds hardly at all when $R^4$ represents an alkyl group. On the contrary, compounds of formula (I) can easily be prepared and readily cyclised to give carbapenem derivatives of formula (IV).

The starting materials of formula (II) used in the preparation of the compounds of the invention may be prepared by a variety of methods, for example as illustrated below.

METHOD A

A compound of formula (IX):

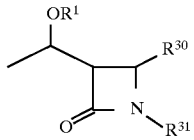

(IX)

(in which $R^1$ is as defined above, $R^{30}$ represents a leaving group and $R^{31}$ represents a hydrogen atom or an amide-protecting group) is reacted with a compound of formula (X):

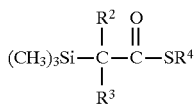

(X)

(in which $R^2$, $R^3$ and $R^4$ are as defined above) in the presence of trimethylsilyl trifluoromethane-sulphonate. The subsequent course of the reaction depends upon the nature of the group represented by $R^{31}$.

(i) Where $R^{31}$ represents a trimethylsilyl group, desilylation occurs easily during subsequent treatment of the reaction mixture, giving a compound of formula (XI):

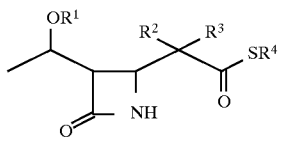

(XI)

(in which $R^1$, $R^2$, $R^3$ and $R^4$ are as defined above), This is then acylated with an alkoxyoxalyl chloride of formula ClCOCOOR$^5$ (in which $R^5$ is as defined above), to give the desired product of formula (II).

(ii) Where $R^{31}$ represents a group of formula

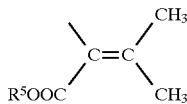

(in which $R^5$ is as defined above), there is obtained a compound of formula (XII):

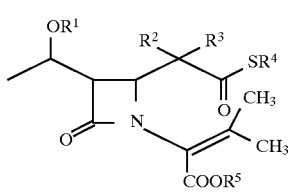

(XII)

(in which $R^1$, $R^2$, $R^3$, $R^4$ and $R^5$ are as defined above). This is then oxidatively cleaved with ozone to give the desired compound of formula (II).

(iii) Where $R^{31}$ represents a group of formula

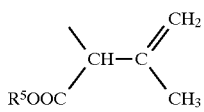

(in which $R^5$ is as defined above), there is obtained a compound of formula (XIII):

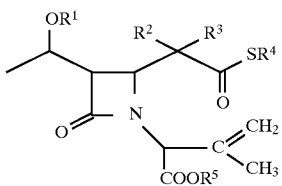

(in which $R^1$, $R^2$, $R^3$, $R^4$ and $R^5$ are as defined above). This is treated with a base, to give the compound of formula (XII) defined above, which is then oxidatively cleaved, to give the desired compound of formula (II).

(iv) Where $R^{31}$ represents an alkoxyoxalyl group, the compound of formula (II) is obtained directly.

METHOD B

Compound of formula (II) may also be prepared by the reaction sequence illustrated in the following reaction scheme:

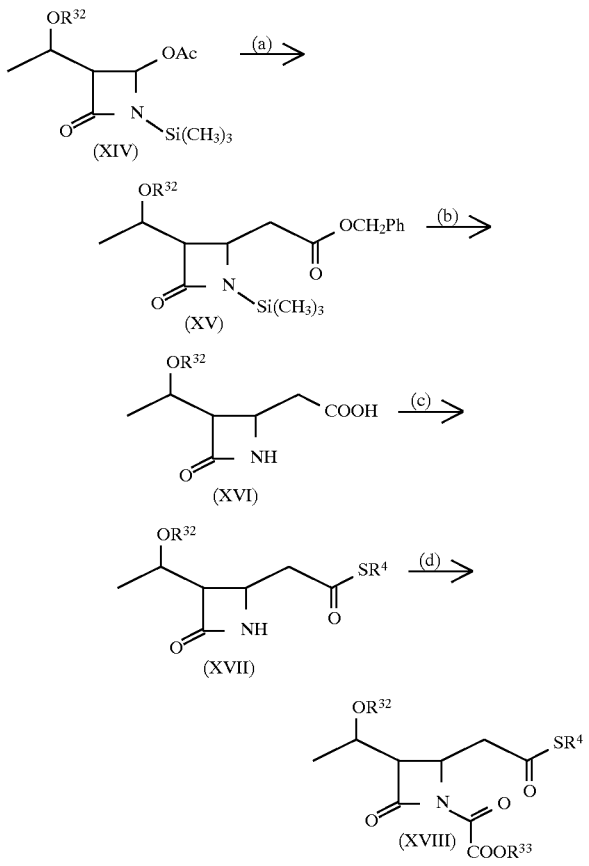

In the above reaction scheme, $R^4$ is as defined above; $R^{32}$ represents a hydroxy-protecting group. examples of which have been given above; $R^{33}$ represents a carboxy-protecting group, examples of which have been given above; Ac represents an acetyl group and Ph represents a phenyl group.

In step (a) of the reaction scheme, the compound of formula (XIV) is reacted with benzyl (trimethylsilyl)-acetate to give the compound of formula (XV) which is then reacted first with water and then with hydrogen in the presence of palladium-on-charcoal to give the compound of formula (XVI).

The compound of formula (XVI) is reacted with a mercaptan of formula $R^4SH$ (in which $R^4$ is as defined above), in the presence of a condensing agent, such as N,N'-dicyclohexylcarbodiimide or diphenylphosphoryl azide/triethylamine, to give the compound of formula (XVII). This is then reacted with an alkoxyoxalyl chloride, to give the desired compound of formula (XVIII), i.e. a compound of formula (II) in which $R^1$ represents a hydroxy-protecting group and $R^5$ represents a carboxy-protecting group.

METHOD C

Compounds of formula (XVIII) can also be prepared by the following reaction scheme:

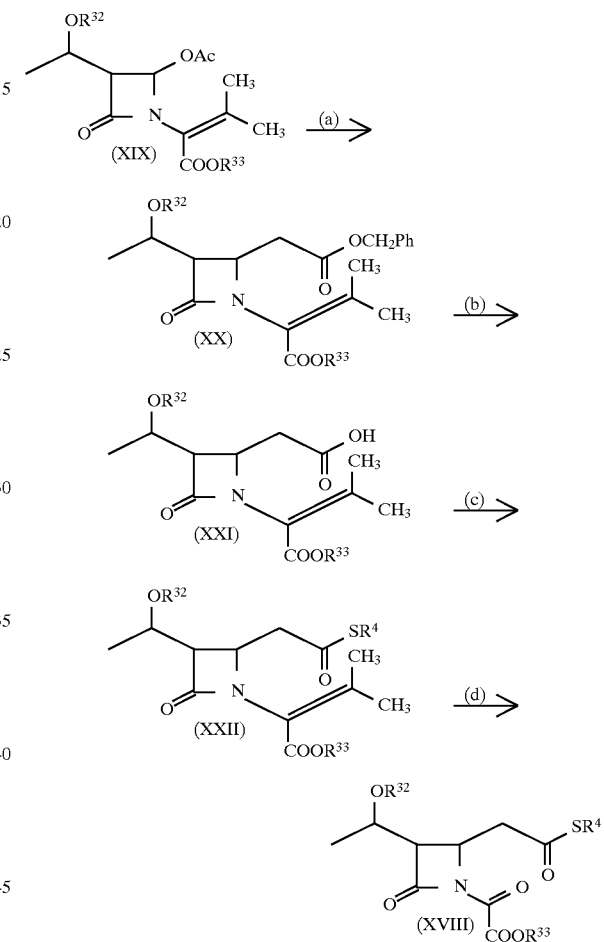

In the above formulae, $R^{32}$, $R^{33}$, $R^4$, Ac and Ph are as defined above.

A compound of formula (XIX) is reacted with benzyl (trimethylsilyl) acetate to give the compound of formula (XX). The benzyl group of this compound is then removed by conventional means, e.g. hydrogenation using hydrogen gas in the presence of palladium-on-charcoal, to give the compound of formula (XXI). This compound of formula (XXI) is reacted with a mercaptan derivative of formula $R^4SH$ (in which $R^4$ is as defined above), in the presence of a condensing agent, such as N, N'-dicyclohexylcarbodiimide or diphenylphosphoryl azide/triethylamine, to give the compound of formula (XXII), which is then oxidised with ozone to the compound of formula (XVIII).

METHOD D

Compounds of formula (II) may also be prepared as illustrated by the following reaction scheme:

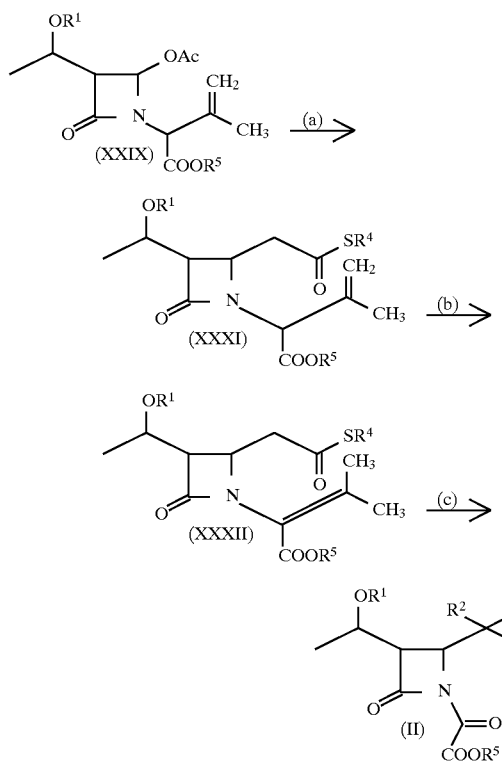

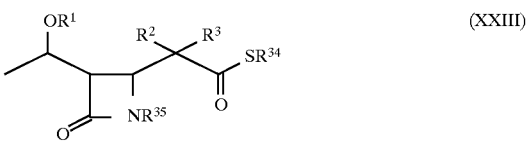

(in which: $R^1$, $R^2$ and $R^3$ are as defined above; $R^{34}$ represents an aryl group or an aromatic heterocyclic group, such as those hitherto exemplified for $R^4$; and $R^{35}$ represents a hydrogen atom or any organic group which is inert to the thioester-exchange reaction) with a compound of formula $R^4SH$ (in which $R^4$ is as defined above).

Provided that the group represented by $R^{35}$ does not participate in or interfere with the thioester-exchange reaction, its nature is not critical. Accordingly, this reaction may be effected at any stage during the processes of the invention and the Methods described above and thus $R^{35}$ can represent any of the groups of formulae:

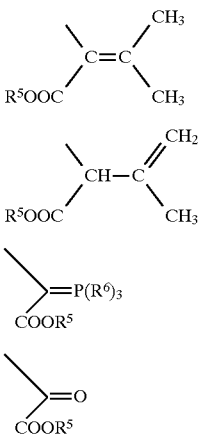

In the above formulae, $R^1$, $R^4$, $R^5$ and Ac are as defined above.

In step (a) of this reaction scheme, the compound of formula (XXIX) is reacted with a compound of formula (XXX):

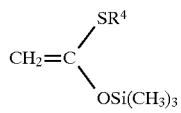
(XXX)

to give the compound of formula (XXXI). This is preferably effected in the presence of a solvent (such as hexane, benzene, toluene, methylene chloride, chloroform, diethyl ether, tetrahydrofuran, dioxane, acetonitrile or dimethylformamide) and in the presence of a catalytic amount of trimethylsilyl trifluoromethanesulphonate, the compound of formula (XXX) being employed in an amount of from 1 to 3 equivalents per equivalent of compound of formula (XXIX). The reaction temperature may vary over a wide range, for example from −15° C. to +100° C. and the time required for the reaction will generally be from 5 hours to 7 days.

In step (b) of the reaction, the resulting compound of formula (XXXI) is treated with a base, for example triethylamine, 1,5-diazabicyclo[4.3.0]non-5-ene, 1,4-diazabicyclo[2.2.2]octane or 4-(N,N-dimethylamino)-pyridine, to give the compound of formula (XXXII). This may then be subjected to ozonolysis in step (c) to give the desired compound of formula (II).

It is also possible to convert one group of formula $SR^4$ to another group in which $R^4$ bears a different meaning, by reacting a compound of formula (XXIII):

This reaction is preferably effected in the presence of a solvent, the nature of which is not critical provided that it does not interfere with the reaction. Examples of suitable solvents include: ethers, such as diethyl ether, tetrahydrofuran or dioxane: aromatic hydrocarbons, such as benzene or toluene; dialkylamides, such as dimethylformamide or dimethylacetamide; halogenated hydrocarbons, such as methylene chloride, chloroform or 1,2-dichloroethane: esters, such as ethyl acetate; alcohols, such as methanol, ethanol or propanol; acetonitrile; dimethyl sulphoxide; and mixtures of any two or more of these. The reaction is promoted by the presence of a base and is, accordingly, preferably effected in the presence of a base, although it is not essential. Suitable bases are such organic bases as triethylamine, diisopropylethylamine, pyridine, 1,4-diazabicyclo[2.2.2]octane and 1, 5-diazabicyclo-[4.3.0]non-5-ene, and such inorganic bases as alkali metal hydroxides (particularly lithium hydroxide, sodium hydroxide or potassium hydroxide) or alkali metal carbonates and bicarbonates (particularly sodium carbonate, potassium carbonate or sodium bicarbonate). The reaction temperature is not particularly critical and we normally prefer to carry out the reaction at a temperature within the range from −20° C. to 100° C. Although it is preferred to carry out the reaction under an atmosphere of an inert gas (such as nitrogen), the reaction also proceeds in air. From 10 minutes to 3 days should be allowed for the reaction, depending upon the nature of the starting materials and the reaction temperature.

The compound of formula (XXIII) employed as a starting material for this thioester-exchange reaction may have been prepared by any of Methods A to D described above. In addition, it may be prepared by the following Method E.

METHOD E

As illustrated in the following reaction scheme:

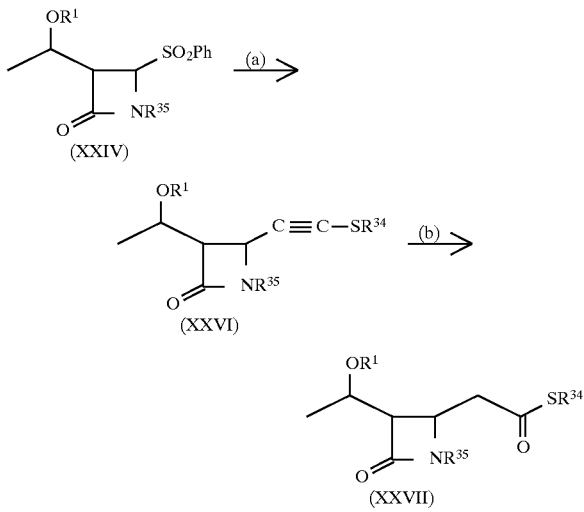

In the above reaction scheme, $R^1$, $R^4$, $R^{34}$, $R^{35}$ and Ph are as defined above.

The compound of formula (XXIV) is reacted in step (a) with a Grignard reagent of formula (XXV):

to give the compound of formula (XXVI). This reaction can be carried out by the method disclosed in Japanese Patent Application Kokai (i.e. as laid open to public inspection) No. 7251/80. The compound of formula (XXVI) can be converted to the compound of formula (XXVII) by hydration using an acidic catalyst, such as trifluoroacetic acid. It will, of course, be appreciated that this Method can also be applied to other starting materials for use in the processes of the present invention.

The processes of the present invention are further illustrated in the following Examples, which also include various steps for the preparation of starting materials for the processes of the invention. Other starting materials for the processes of the invention may be prepared as illustrated in the following Preparations. All values for specific rotation were measured using the sodium D line, i.e. all values are $[\alpha]_d$.

EXAMPLE 1(a)

(3S, 4R)-3-[(R)-1-t-Butyldimethylsilyloxyethyl]-4-[(butylthio)carbonylmethyl]-2-azetidinone.

542 mg (1.89 mmole) of (3S, 4R)-3-[(R)-1-t-butyldimethylsilyloxyethyl]-4-carboxymethyl-2-azetidinone, 212 mg (2.36 mmole) of butyl mercaptan, 381 mg (3.77 mmole) of triethylamine and 1.04 g (3.78 mmole) of diphenylphosphoryl azide were dissolved in 10 ml of N,N-dimethylformamide and the solution was allowed to stand overnight at room temperature. After dilution with ethyl acetate, the mixture was washed with water several times and then dried. The solvent was distilled off and the residue (1.25 g) was purified by column chromatography through 23 g of silical gel, eluted with mixtures of hexane and ethyl acetate in volume ratios ranging from 4:1 to 2:1, to give 649 mg (yield 96%) of the title product. Recrystallization from hexane gave colourless needles, melting at 56.5°–57° C.

Elemental Analysis Calculated for $C_{17}H_{33}NO_3SSi$ C, 56.78%; H, 9.25%; N, 3.90%; S, 8.92%. Found: C, 56.88%; H, 9.15%; N, 3.89%; S, 9.08%. Infrared absorption spectrum (Nujol) $v_{max}$ cm$^{-1}$: 3160, 3090, 1762, 1722, 1683.

Nuclear Magnetic Resonance Spectrum (CDCl$_3$) δ ppm 0.06 (6H, singlet); 0.89 (9H, singlet); 0.6–1.8 (7H, multiplet); 1.16 (3H, doublet, J=6 Hz); 2.7–3.2 (5H, multiplet); 3.9 (1H, multiplet); 4.15 (1H, quintet, J=6 Hz); 6.4 (1H, broad singlet).

EXAMPLE 1(b)

(3S, 4R)-3-[(R)-1-t-Butyldimethylsilyloxyethyl]-4-[(butylthio)carbonylmethyl]-1-(p-nitrobenzyloxyethyl)-2-azetidinone.

To a solution of 150 mg (0.418 mmole) of (3S, 4R)-3-[(R)-1-t-butyldimethylsilyloxyethyl]-4-[(butylthio)-carbonylmethyl]-2-azetidinone in 6 ml of 1,2-dichloroethane were added successively 140 mg (1.25 mmole) of 1,4-diazabicyclo[2,2,2]octane and 305 mg (1.25 mmole) of p-nitrobenzyloxyethyl chloride, with ice cooling and stirring under a nitrogen atmosphere.

After the mixture had been stirred for 2 hours, a 0.1M phosphate buffer solution (pH 7.2) was added to the reaction mixture to complete the reaction. To the reaction mixture was then added methylene chloride and the organic layer was separated, washed with water and then dried. The solvent was distilled off and the resulting residue (232 mg) was purified by column chromatography through 6 g of silical gel, eluted with a 5:1 by volume mixture of hexane and ethyl acetate, to give 132 mg (yield 56%) of the title product as an oil.

Infrared absorption spectrum (CHCl$_3$) $v_{max}$ cm$^{-1}$: 1802, 1756, 1687, 1520, 1346.

Nuclear Magnetic Resonance Spectrum (CDCl$_3$) δ ppm 0.01 (3H, singlet); 0.08 (3H, singlet); 0.80 (9H, singlet); 0.90 (3H, triplet, J=6 Hz); 1.19 (3H, doublet, J=6 Hz); about 1.5 (4H, multiplet); 2.90 (2H, triplet, J=6 Hz); 3.00 (1H, doubled doublet, J=15 & 8 Hz); 3.33 (1H, triplet, J=3 Hz); 3.40 (1H, doubled doublet, J=15 & 4 Hz); 4.31 (1H, quadrupled doublet, J=6 & 3 Hz); 4.61 (1H, doubled doubled doublet, J=8 & 4 & 3 Hz); 5.40 (2H, singlet); 7.58 (2H, doublet, J=9 Hz); 8.23 (2H, doublet, J=9 Hz).

EXAMPLE 1(c)

(3S, 4R)-3-[(R)-1-t-Butyldimethylsilyloxyethyl]-4-[(butylthio)carbonylmethyl)]-1-[1-(p-nitrobenzyloxycarbonyl)-1-trimethoxyphosphoranylidenemethyl]-2-azetidinone.

A mixture of 61 mg (0.11 mmole) of (3S, 4R)-3-[(R)-1-t-butyldimethylsilyloxyethyl]-4-[(butylthio)-carbonylmethyl]-1-(p-nitrobenzyloxyethyl)-2-azetidinone, 107 mg (0.86 mmole) of trimethyl phosphite and 7 ml of ethyl acetate was stirred at 70°–80° C. for 65 hours under a nitrogen atmosphere. The solvent and excess trimethyl phosphite were distilled off under reduced pressure to give 69 mg (yield 95%) of the title product as an oil.

Infrared absorption spectrum (CHCl$_3$) $v_{max}$ cm$^{-1}$: 1740: 1675, 1631, 1520, 1343.

Nuclear Magnetic Resonance Spectrum (CDCl$_3$) δ ppm: 0.05 (6H, singlet); 0.85 (9H, singlet); 0.90 (3H, triplet, J=6

Hz); 1.23 (3H, doublet, J=6 Hz); about 1.5 (4H, multiplet); 2.5–3.1 (5H, multiplet); 3.87 (9H, doublet, J=12 Hz); about 4.0 (2H, multiplet); 5.0–5.4 (2H, multiplet); 7.48 and 7.54 (2H, doublet), 8.15 and 8.19 (2H, doublet).

EXAMPLE 1(d)

p-Nitrobenzyl (5R, 6S)-6-[(R)-1-t-butyldimethylsilyl-oxyethyl]-2-(butylthio)carbapen-2-em-3-carboxylate A mixture of 69 mg (0.10 mmole) of crude (3S, 4R)-3-[(R)-1-t-butyldimethylsilyloxyethyl]-4-[(butylthio)-carbonylmethyl]-1-[1-(p-nitrobenzyloxycarbonyl)-1-trimethoxyphosphoranylidenemethyl]-2-azetidinone, prepared as described in Example 1(c), 5 mg (0.05 mmole) of hydroquinone and 9 ml of xylene was heated at 120° C. for 21 hours under a nitrogen atmosphere. The solvent was distilled off under reduced pressure and the resulting residue was purified by preparative thin layer chromatography on silica gel, developed with a 1.5:1 by volume mixture of hexane and ethyl acetate, to give 10 mg (yield 18%) of the title product as an oil.

Infrared absorption spectrum (CHCl$_3$) $v_{max}$ cm$^{-1}$: 1768, 1695, 1605, 1520, 1345.

Nuclear Magnetic Resonance Spectrum (CDCT3) δ ppm: 0.00 (6H, singlet); 0.80 (9H, singlet); 0.86 (3H, triplet, J=6 Hz); 1.18 (3H, doublet, J=6 Hz); about 1.5 (4H, multiplet); 2.77 (2H, triplet-like, J=6 Hz); 3.0–3.2 (3H, multiplet); 4.0–4.3 (2H, multiplet); 5.17 (1H, doublet, J=14 Hz); 5.42 (1H, doublet, J=14 Hz); 7.59 (2H, doublet, J=9 Hz); 8.16 (2H, doublet, J=9 Hz).

EXAMPLE 2(a)

(3S, 4R)-3-[(R)-1-t-Butyldimethylsilyloxyethyl]-4-[(isopropylthio)carbonylmethyl]-2-azetidinone.

1.15 g (4.00 mmole) of (3S, 4R)-3-[(R)-1-t-butyldimethylsilyloxyethyl]-4-carboxymethyl-2-azetidinone, 380 mg (5.00 mmole) of isopropyl mercaptan, 808 mg (8.00 mmole) of triethylamine and 2.20 g (8.00 mmole) of diphenylphosphoryl azide were dissolved successively in 20 ml of N,N-dimethylformamide, and the solution was allowed to stand for 15 hours at room temperature, After completion of the reaction, the reaction mixture was poured into ice-water, and was extracted twice with ethyl acetate; the extract was washed with water and dried. The solvent was distilled off and the resulting residue was purified by column chromatography through 30 g of silica gel, eluted with a 3:1 by volume mixture of hexane and ethyl acertate, to give 1.06 g (yield 77%) of the title product as a solid.

Recrystallization from hexane gave pure product, melting at 87–90° C.

Elemental Analysis Calculated for C$_{16}$H$_{31}$NO$_3$SSi: C, 55.61%; H; 9.04%; N, 4.05%; S, 9.28% Found: C, 55.71%; H, 8.92%; N, 4.25%; S, 9.24%

Infrared absorption spectrum (CHCl$_3$) $v_{max}$ cm$^{-1}$: 3420, 1756, 1670.

Nuclear Magnetic Resonance Spectrum (CDCl$_3$) δ ppm 0.08 (6H, singlet); 0.88 (9H, singlet); 1.18 (3H, doublet, J=6 Hz), 1.30 (6H, doublet, J=7 Hz); about 2.8 (3H, multiplet); 3.64 (1H, multiplet); 3.8–4.4 (2H, multiplet); 6.3 (1H, broad singlet).

EXAMPLE 2(b)

(3S, 4R)-3-[(R)-1-t-Butyldimethylsilyloxyethyl]-4-[(isopropylthio)carbonylmethyl]-1-(p-nitrobenzloxyoxalyl)-2-azetidinone To a solution of 708 mg (2.05 mmole) of (3S, 4R)-3-[(R)-1-t-butyldimethylsilyloxyethyl]-4-[(isopropylthio)-carbonylmethyl]-2-azetidinone in 30 ml of methylene chloride were added successively 689 mg (6.15 mmole) of 1,4-diazabicyclo[2,2,2] octane and 1.50g (6.15 mmole) of p-nitrobenzyloxyethyl chloride, with ice cooling and stirring. After the mixture had been stirred for 1.5 hours, 20 ml of a 0.1M phosphate buffer solution were added.

The organic layer was separated, washed with water and then dried. The solvent was distilled off and the resulting residue was purified by column chromatography through 20 g of silica gel eluted with mixtures of hexane and ethyl acetate in volume ratios ranging from 5:1 to 4:1, to give 1.12 g (yield 99%) of the title product as an oil.

Infrared absorption spectrum (CHCl$_3$) $v_{max}$ cm$^{-1}$: 1804, 1755, 1695.

Nuclear Magnetic Resonance Spectrum (CDCl$_3$) δ ppm 0.03 (3H, singlet); 0.05 (3H, singlet); 0.80 (9H, singlet); 1.18 (3H, doublet, J=6 Hz); 1.30 (6H, broad doublet J=7 Hz); 2.96 (1H, doubled doublet J=15 & 8 Hz); 3.32 (1H, doubled doublet J=15 & 4 Hz); 3.33 (1H, triplet, J=3 Hz); 3.65 (1H, multiplet); about 4.3 (1H, multiplet); about 4.6 (1H, multiplet); 5.40 (2H, singlet); 7.56 (2H, doublet); 8.17 (2H, doublet).

EXAMPLE 2(c)

p-Nitrobenzyl (5R, 6S)-6-[(R)-1-t-butyldimethyl-silyloxyethyl]-2-(isopropylthio)carbapen-2-em-3-carboxylate A mixture of 55 mg (0.10 mmole) of (3R, 4R)-3-[(R)-1-t-butyldimethylsilyloxyethyl]-4-[(isopropylthio)carbonyl-methyl]-1-(p-nitrobenzyloxyethyl)-2-azetidinone, 100 mg (0.60 mmole) of triethyl phosphate, 3 mg of hydroquinone and 5.5 ml of xylene was heated at 120° C. for 70 hours under a nitrogen atmosphere. After completion of the reaction, the solvent and the volatile substances were distilled off under reduced pressure. The resulting oil was again dissolved in 5.5 ml of xylene and the solution was heated at 120° C. for 70 hours under a nitrogen atmosphere. After completion of the reaction, the solvent was distilled off under reduced pressure, and the residue was purified by preparative thin layer chromatography, developed with a 3:1 by volume mixture of hexane and ethyl, acetate, to give 26.6 mg (yield 51%) of the title product as an oil.

Infrared absorption spectrum (CHCl$_3$) $v_{max}$ cm$^{-1}$: 1768, 1690.

Nuclear Magnetic Resonance Spectrum (CDCl$_3$) δ ppm: 0.08 (6H, singlet); 0.87 (9H, singlet); 1.25 (3H, doublet, J=6 Hz); 1.35 (6H, broad doublet, J=7 Hz); 2.9–3.6 (3H, multiplet); 3.9–4.4 (2H, multiplet); 5.20 (1H, doublet, J=14 Hz); 5.45 (1H, doublet, J=14 Hz); 7.62 (2H, doublet); 8.19 (2H, doublet).

EXAMPLE 3(a)

(3S, 4R)-3-[(R)-1-t-Butyldimethylsilyloxyethyl]-4-[(Phenylthio)carbonylmethyl]-2-azetidinone 1.10 g (3.06 mmole) of (3R, 4R)-4-acetoxy-3-[(R)-1-t-butyldimethylsilyloxyethyl]-1-trimethylsilyl-2-azetidinone and 961 mg (4.29 mmole) of S-phenyl-trimethylsilyl ethanethiol were dissolved in 20 ml of methylene chloride. To the solution was added 0.07 ml (0.32 mmole) of trim-ethylsilyl trifluoromethane-sulphonate, at −20° C. under a nitrogen atmosphere, and the reaction mixture was stirred for 4.5 hours at from −10° to +5° C. Water was then added to the mixture to complete the reaction. The methylene chloride layer was separated and washed successively with a dilute aqueous solution of sodium bicarbonate and with a saturated aqeuous solution of sodium chloride.

The solvent was then distilled off and the residue was dissolved in 2.5 ml of ethanol. To the solution were added 58 mg (1.00 mmole) of potassium fluoride, and the reaction mixture was stirred for 1.5 hours at room temperature and then diluted with ethyl acetate. It was then washed successively with water and with a saturated aqueous solution of sodium chloride. The solvent was distilled off and the resulting residue was purified by Lobar column chromatography (E. Merck Co., Ltd.), to give 961 mg (yield 83%) of the title product as crystals from the fraction eluted with a 2:1 by volume mixture of hexane and ethyl acetate. Recrystallization from hexane gave needles, melting at 94°–95° C.

Elemental Analysis Calculated for $C_{19}H_{29}NO_3SSi$; C, 60.12%; H, 7.70%; N, 3.69%; S, 8.45%. Found: C, 60.11%; H, 7.72%; N, 3.67%; S, 8.54%.

Infrared absorption spectrum (Nujol) $84_{max}$ cm$^{-1}$: 3160, 3000, 1767, 1726, 1703.

Nuclear Magnetic Resonance Spectrum (CDCl$_3$) δ ppm: 0.08 (6H, singlet); 0.88 (9H, singlet); 1.21 (3H, doublet, J=6 Hz); 2.7–3.2 (3H, multiplet); 4.0 (1H, multiplet); 4.18 (1H, quintet, J=6 Hz); 6.10 (1H, broad singlet); 7.4 (5H, singlet).

EXAMPLE 3(b)

(3S, 4R)-3-[(R)-1-t-Butyldimethylsilyloxyethyl]-1-(p-nitrobenzyloxyethyl)-4-[(phenylthio)carbonylmethyl]-2-azetidinone 747 mg (1.97 mmole) of (3S, 4R)-3-[(R)-1-t-butyldimethylsilyloxyethyl]-4-[(phenylthio)carbonylmethyl]-2-azetidinone and 398 mg (3.94 mmole) of triethylamine were dissolved in 20 ml of methylene chloride. To the solution were added 960 mg (3.94 mmole) of p-nitrobenzyloxyethyl chloride, with ice cooling under a stream of nitrogen. The mixture was stirred for 2 hours and then a 0.1M phosphate buffer solution (pH 7.2) was added to the reaction mixture to complete the reaction. The organic layer was separated and washed with water, after which it was dried. The solvent was distilled off and the resulting residue was purified by column chromatography through 15 g of silica gel, to give 1,032 mg (yield 89%) of the desired product as an oil from the fractions eluted with mixtures of hexane and ethyl acetate in volume ratios from 6:1 to 3:1.

Infrared absorption spectrum (CHCl$_3$) $v_{max}$ -cm$^{-1}$: 1805, 1757, 1699, 1609, 1522, 1344.

Nuclear Magnetic Resonance Spectrum (CDCl$_3$) δ ppm: 0.02 (3H, singlet); 0.04 (3H, singlet); 0.08 (9H, singlet); 1.14 (3H, doublet, J=6 Hz); 3.11 (1H, doubled doublet, J=15 & 8 Hz); 3.35 (1H, triplet, J=3 Hz); 3.43 (1H, doubled doublet, J=15 & 4 Hz); 4.29 (1H, quadrupled doublet, J=6 & 3 Hz); 4.64 (1H, doubled doubled doublet, J=8 & 4 & 3 Hz); 5.37 (2H, singlet); 7.52 (2H, doublet, J=8 Hz); 8.16 (2H, doublet, J=8 Hz);

EXAMPLE 3(c)

p-Nitrobenzyl (5R, 6S)-6-[(R)-1-t-butyldimethyl-silyloxyethyl]-2-(phenylthio)carbapen-2-em-3-carboxylate A mixture of 511 mg (0.872 mmole) of (3S, 4R)-3-[(R)-1-t-butyldimethylsilyloxyethyl]-1-(p-nitrobenzyloxyethyl)-4-[(phenylthio)carbonylmethyl]-2-azetidinone, 1.03 g (8.46 mmole) of trimethyl phosphite and 50 ml of ethyl acetate was stirred at 70° C. for 4 days under a nitrogen atmosphere.

The solvent was then distilled off and the residue was purified by high pressure liquid chromatography using a Lobar column (E. Merck Co., Ltd.), eluted with a 1:3 by volume mixture of benzene and ethyl acetate, to give 158 mg of the title product containing some impurities and 176 mg (yield 29%) of (3S, 4R)-3-[(R)-1-t-butyldimethyl-silyloxyethyl]-1-[1-(p-nitrobenzyloxy-carbonyl)-1-trimethoxyphosphoranylidenemethyl]-4-[(phenylthio)carbonylmethyl]-2-azetidinone.

The mixture containing the title product was further purified by chromatography using a Lobar column, eluted with a 3.5:1 by volume mixture of hexane and acetone, to give 103 mg (yield 21%) of the title product as a solid, which, on recrystallization from acetone-hexane, gave pure colourless needles melting at 144°145.5° C.

Trimethoxyphosphoranylidene compound

Infrared absorption spectrum (CHCl$_3$) $v_{max}$ cm$^{-1}$: 1740, 1695, 1636, 1520, 1345.

Nuclear Magnetic Resonance Spectrum (CDCl3) δ ppm: 0.00 (6H, singlet); 0.87 (9H, singlet); 1.26 (3H, doublet, J=6 Hz); 2.7–3.5 (3H, multiplet); 3.84 (9H, doublet, J=12 Hz); about 4.2 (2H, multiplet); 4.9–5.5 (2H, multiplet); 7.36 (5H, singlet); 7.53 (2H, doublet, J=9 Hz); 8.17 (2H, doublet, J=9 Hz).

Carbapenem

Elemental Analysis Calculated for $C_{28}H_{34}N_2O_6SSi$: C, 60.62%; H, 6.18%; N, 5.05%; S, 5.78%. Found: C, 60.50%; H, 6.11%; N, 4.77%; S, 5.91%.

Infrared absorption spectrum (Nujol-trade mark) $v_{max}$ cm$^{-1}$: 1777, 1697, 1524.

Nuclear Magnetic Resonance Spectrum (CDCl$_3$) δ ppm 0.06 (6H, singlet); 0.83 (9H, singlet); 1.15 (3H, doublet, J=6 Hz); 2.63 (2H, doublet, J=10 Hz); 3.05 (1H, doubled doublet, J=4 & 2 Hz); 4.04 (1H, doubled doublet, J=10 & 2 Hz); 4.19 (1H, doubled quartet, J=4 & 6 Hz); 5.22 (1H, doublet, J=14 Hz); 5.50 (1H, doublet, J=14 Hz); 7.2–7.7 (5H, multiplet); 7.64 (2H, doublet, J=9 Hz); 8.19 (2H, doublet, J=9 Hz).

EXAMPLE 4 p-Nitrobenzyl (5R, 6S)-6-[(R)-1-t-butyldimethyl-silyloxyethyl]-2-(phenylthio)carbapen-2-em-3-carboxylate A mixture of 19 mg (0.027 mmole) of (3S, 4R)-3-[(R)-1-t-butyldimethylsilyloxyethyl]-1-[1-(p-nitrobenzyloxy-carbonyl)-1-trimethoxyphosphoranylidenemethyl]-4-[(phenylthio)carbonylmethyl]-2-azetidinone [prepared as described in Example 3(c)], a catalytic amount of hydroquinone and 2 ml of xylene was stirred at 120° C. for 4 hours under a nitrogen atmosphere. After completion of the reaction, the solvent was distilled off, and the residue was purified using Lobar column chromatography, using as eluent a 3.5:1 by volume mixture of hexane and acetone, to give 75 mg (yield 45%) of the title product as a solid.

EXAMPLE 5 p-Nitrobenzyl (5R, 6S)-6-[(R)-1-t-butyldimethylsilyloxyethyl]-2-(phenylthio)carbapen-2-em-3-carboxylate A mixture of 114 mg (0.194 mmole) of (3S, 4R)-3-[(R)-1-t-butyldimethylsilyloxyethyl]-1-(p-nitrobenzyloxyethyl)-4-[( phenylthio)carbonylmethyl]-2-azetidinone, 258 mg (1.55 mmole) of triethyl phosphate and 10 ml of toluene was stirred at 100° C. for 18 hours under a nitrogen atmosphere.

EXAMPLE 6 p-Nitrobenzyl (5R, 6S)-6-[(R)-1-t-butyldimethylsilyloxyethyl]-2-(phenylthio)carbapen-2-em-3-carboxylate Following the procedure of Example 5, 83 mg (yield 77%) of the title product was obtained as crystals, using 324 mg (1.56 mmole) of triisopropyl phosphite instead of the triethyl phosphate.

EXAMPLE 7 p-Nitrobenzyl (5R, 6S)-6-[(R)-i-t-butyldimethylsilyloxyethyl]-2-(phenylthio)carbapen-2-em-3-carboxylate Following the procedure of Example 5, 37 mg (yield 34%) of the desired product was obtained as crystals, using 195 mg (1.56 mmole) of trimethyl phosphite instead of the triethyl phosphate.

EXAMPLE 8(a)

(3S, 4R)3-[(R)-1-t-Butyldimethylsilyloxyethyl]-4-([2-(p-nitrobenzyloxycarbonylamino)ethylthio]carbonyl-methyl)-2-azetidinone.

1.00 9 (3,48 mmole) of (3S, 4R)-3-[(R)-1-t-butyldimethylsilyloxyethyl]-4-carboxymethyl-2-azetidinone and 1.07 g (4.8 mmole) of 2-(p-nitrobenzyloxycarbonyl-amino)ethanethiol were dissolved in 20 ml of benzene. To this solution were added 861 mg (4.18 mmole) of dicyclohexylcarbodiimide and 10 mg (0.082 mmole) of 4-dimethylaminopyridine, at room temperature with stirring. The mixture was stirred for 2 hours, after which the insolubles which had formed were filtered off and the resulting filtrate was concentrated to dryness by evaporation under reduced pressure, The residue was purified by column chromatography through 40 g of silica gel, to give 1.59 g (yield 87%) of the desired product as an oil from the fractions eluted with a 1:1 volume mixture of benzene and ethyl acetate.

Infrared absorption spectrum (CHCl$_3$) $v_{max}$ cm$^{-1}$: 3390, 1746, 1715, 1673.

Nuclear Magnetic Resonance Spectrum (CDCl$_3$) δ ppm: 0.07 (6H, singlet); 0.87 (9H, singlet); 1.17 (3H, doublet, J=6 Hz); 2.7–3.6 (7H, multiplet); 3.8–4.4 (2H, multiplet); 5.12 (2H, singlet); 5.88 (1 Hz, broad triplet, J=6 Hz); 6.91 (1H, singlet); 7.41 (2H, doublet); 8.10 (2H, doublet).

EXAMPLE 8(b)

(3S, 4R)-3-[(R)-1-t-Butydimethylsilyloxyethyl]-4-([2-(p-nitrobenzyloxycarbonylamino)ethylthio]-carbonylmethyl)-1-(p-nitrobenzyloxyethyl)-2-azetidinone To a solution of 500 mg (0.95 mmole) of (3S, 4R)-3-[(R)-1-t-butyldimethylsilyloxyethyl]-4-([2-(p-nitrobenzyl-oxycarbonylamino)ethylthio]carbonylmethyl)-2-azetidinone in 6 ml of methylene chloride were added successively 288 mg (2.85 mmole) of triethylamine and 694 mg (2.85 mmole) of p-nitrobenzyloxyethyl chloride, at 0° C. with stirring.

After 1 hour, 10 ml of 0.1M phosphate buffer solution (pH 7.0) were added to the reaction mixture. The organic layer was separated and then dried. The solvent was distilled off and the resulting residue was purified by column chromatography through 8 g of silica gel eluted with a 1:1 by volume mixture of hexane and ethyl acetate, to give 642 mg (yield 92%) of the title product as an oil.

Infrared absorption spectrum (CHCl$_3$) $v_{max}$ cm$^{-1}$: 3450, 1802, 1745 (shoulder), 1715, 1700 (shoulder).

Nuclear Magnetic Resonance Spectrum (CDCl$_3$) δ ppm: 0.02 (3H, singlet); 0.05 (3H, singlet); 0.80 (9H, singlet); 1.18 (3H, doublet, J=6 Hz); 2.8–3.6 (7H, multiplet); about 4.25 (1H, multiplet); about 4.6 (1H, multiplet); 5.15 (2H, singlet); 5.36 (2H, singlet); 7.46 (2H, doublet); 7.54 (2H, doublet); 8.17 (2H, doublet); 8.19 (2H, doublet).

EXAMPLE 8(c)

p-Nitrobenzyl (5R, 6S)-6-[(R)-1-t-butyldimethylsilyloxyethyl]-2-[2-(p-nitrobenzyloxycarbonylamino)ethylthio]carbapen-2-em-3-carboxylate.

A mixture of 165 mg (0.23 mmole) of (3S, 4R)-3-[(R)-1-t-butyldimethylsilyloxyethyl]-4-([2-(p-nitrobenzyloxycarbonylamino)ethylthio]carbonylmethyl)-1-(p-nitrobenzyloxyethyl)-2-azetidinone, 229 mg (1.38 mmole) of triethyl phosphite, 4 mg of hydroquinone and 16.5 ml of toluene was heated at 90° C. for 30 hours under a nitrogen atmosphere, and then the toluene was distilled off under reduced pressure and the residue was purified by liquid chromatography using a Lobar column B (E. Merck Co., Ltd.), eluted with a 2:1 by volume mixture of benzene and ethyl acetate, to afford 107 mg (yield 68%) of the title product as a solid.

Recrystallization from benzene-hexane gave pure product melting at 65°–67° C.

Infrared absorption spectrum (CHCl$_3$) ) $v_{max}$ cm$^{-1}$: 3450, 1770, 1715, 1696 (shoulder).

Nuclear Magnetic Resonance Spectrum (CDCl3) δ ppm 0.09 (6H, singlet); 0.88 (9H, singlet); 1.23 (3H, doublet, J=6 Hz); 2,7–3.7 (6H, multiplet); 3.9–4.5 (2H, multiplet); 5.13 (2H, singlet); 5.15 (1H, doublet, J=14 Hz); 5.39 (1H, doublet, J=14 Hz); 7.41 (2H, doublet); 7.56 (2H, doublet; 8.13 (4H, doublet).

EXAMPLE 9(a)

(3S, 4R)-3-[(R)-1-t-Butyldimethylsilyloxyethyl-4-([(S)-1-(p-nitrobenzyloxycarbonyl)pyrrolidin-3-ylthio]-carbonylmethyl)-2-azetidinone.

180 mg (0.50 mmole) of (3R, 4R)-4-acetoxy-3-[(R)-1-t-butyldimethylsilyloxyethyl]-1-(trimethylsilyl)-2-azetidinone and 414 mg (1.00 mmole) of (S)-1-(p-nitrobenzyloxycarbonyl)-3-(trimethylsilylacetylthio) pyrrolidine were dissolved in 3 ml of methylene chloride. To the solution were added 15 mg (0.07 mmole) of trimethylsilyl trifluoromethanesulphonate, and the mixture was allowed to stand at room temperature for 15 hours. After completion of the reaction, the reaction mixture was poured into an aqueous solution of sodium bicarbonate, with stirring. The organic layer was separated, washed with water and then dried. The solvent was distilled off and the resulting residue was purified by preparative thin layer chromatography, developed with a 6:1 by volume mixture of chloroform and ethyl acetate, to give 185 mg (yield 67%) of the desired product as a solid. Recrystallization from hexane-ethyl acetate gave a pure product, melting at 104°–106° C.

Infrared absorption spectrum (CHCl$_3$) $\nu_{max}$ cm$^{-1}$: 3410, 1775, 1685.

Nuclear Magnetic Resonance Spectrum (CDCl$_3$) δ ppm 0.08 (6H, singlet); 0.88 (9H, singlet); 1.19 (3H, doublet, J=6 Hz); 1.7–2.5 (2H, multiplet); 2.7–3.0 (2H, multiplet); 3.53 (2H, triplet, J=7 Hz); 3.2–4.4 (6H, multiplet); 5.19 (2H, singlet); 6.15 (1H, broad singlet); 7.42 (2H, doublet); 8.20 (2H, doublet).

EXAMPLE 9(b)

(3S, 4R)-3-[(R)-1-t-Butyldimethylsilyloxyethyl]-1-(p-nitrobenzyloxyethyl)-4-([(S)-1-(p-nitrobenzyloxycarbonyl)pyrrolidin-3-ylthio]carbonylmethyl)-2-azetidinone.

57.7 mg (0.105 mmole) of (3S, 4R)-3-[(R)-1-t-butyldimethylsilyloxyethyl]-4-([(S)-1-(p-nitrobenzyloxycarbonyl)pyrrolidin-3-ylthio]carbonylmethyl)-2-azetidinone and 33 mg (0.33 mmole) of triethylamine were dissolved in 3 ml of methylene chloride. To the solution were added 73 mg (0.30 mmole) of p-nitrobenzyloxyethyl chloride, with ice-cooling under a nitrogen atmosphere. The mixture was stirred for 1 hour and then poured into a 0.1M phosphate buffer solution (pH 7.2). The organic layer was separated and washed with a saturated aqueous solution of sodium chloride. The solvent was distilled off and the residue was purified by column chromatography through 1.3 g of silica gel, to give 67.8 mg (yield 83%) of the desired product as an oil from the fraction eluted with mixtures of benzene and ethyl acetate in volume ratios from 12:1 to 4:1.

Infrared absorption spectrum (CHCl$_3$) $\nu_{max}$ cm$^{-1}$: 1800, 1754, 1685, 1682.

Nuclear Magnetic Resonance Spectrum (CDCl3) δ ppm 0.03 (3H, singlet); 0.13 (3H, singlet); 0.85 (9H, singlet); 1.23 (3H, doublet, J=6 Hz); 1.5–2.5 (2H, multiplet); 3.0–5.0 (10H, multiplet); 5.23 (2H, singlet); 5.43 (2H, singlet); 7.50 (2H, doublet, J=8 Hz); 7.56 (2H, doublet, J=8 Hz); 8.22 (4H, doublet, J=8 Hz).

EXAMPLE 9(c)

p-Nitrobenzyl (5R, 6S)-6-[(R)-1-t-butyldimethylsilyloxyethyl]-2-[(S)-1-(p-nitrobenzyloxycarbonyl)-pyrrolidin-3-yl thiocarbapen-2-em-3-carboxylate.

A mixture of 190 mg (0.25 mmole) of (3S, 4R)-3-[(R)-1-t-butyldimethylsilyloxyethyl]-1-( -nitrobenzyloxyethyl)-4-([(S)-1-(p-nitrobenzyloxycarbonyl)pyrrolidin-3-ylthio]carbonylmethyl)-2-azetidinone, 250 mg (1.5 mmole) of triethyl phosphite, 10 mg (0.09 mmole) of hydroquinone and 20 ml of toluene was heated at 95° C. for 15 hours under a nitrogen atmosphere. The reaction mixture was subjected to thin layer chromatography and, as the reaction proceeded, the spot of the starting substance disappeared and the desired carbapenem and (3S, 4R)-3-[(R)-1-t-butyldimethylsilyl-oxyethyl]-1-[1-(p-nitrobenzyloxycarbonyl)-1-triethoxy-phosphoranylidenemethyl]-4-([(S)-1-(p-nitrobenzyloxy-carbonyl)pyrrolidin-3-ylthio]carbonylmethyl)-2-azetidinone were observed.

The solvent and excess triethyl phosphite were distilled off under reduced pressure and the oily residue was dissolved again in 20 ml of toluene. The solution was heated at 95° C. for 57 hours in order to complete the cyclization reaction of the phosphorane. The solvent was distilled off and the residue was purified using a Lobar column (eluent: a 2:1 by volume mixture of benzene and ethyl acetate), to give 151.5 mg (yield 83%) of the title product as an oil.

Infrared absorption spectrum (CHCL$_3$) $\nu_{max}$ cm$^{-1}$: 1770, 1695.

Nuclear Magnetic Resonance Spectrum (CDCl$_3$) δ ppm 0.07 (6H, singlet); 0.87 (9H, singlet); 1.24 (3H, doublet, J=6 Hz); 1.6–2.8 (2H, multiplet),; 2.8–4.5 (10H, multiplet); 5.14 (1H, doublet J=14 Hz); 5.18 (2H, singlet); 5.41 (1H, doublet J=14 Hz); 7.46 (2H, doublet, J=9 Hz); 7.61 (2H, doublet, J=9 Hz); 8.17 (4H, doublet, J=9 Hz).

EXAMPLE 10(a)

(3S, 4R)-3-[(R)-1-t-Butyldimethylsilyloxyethyl]-4-([(S)-1-[N-(p-nitrobenzyloxycarbonyl)acetimidoyl]-pyrrolidin-3-ylthio]carbonylmethyl)-2-azetidinone 2.67 mg (0.93 mmole) of (3S, 4R)-3-[(R)-1-t-butyldimethylsilyloxyethyl]-4-carboxymethyl-2-azetidinone and 330 mg (1.02 mmole) of (S)-3-mercapto-1-[N-(p-nitrobenzyloxycarbonyl)acetimidoyl]pyrrolidine were dissolved in 5 ml of benzene. 210 mg (9.02 mmole) of dicyclohexylcarbodiimide and 5 mg (0.04 mmole) of 4-dimethylaminopyridine were added, and the mixture was stirred at room temperature for 1 hour, after which insolubles were filtered off. The filtrate was concentrated to dryness by evaporation under reduced pressure and the resulting oily residue was purified by column chromatography through 15 g of silica gel eluted with mixtures of benzene and ethyl acetate in volume ratios from 1:2 to 1:5, to give 495 mg (yield 90%) of the title product in the form of an oil.

Infrared absorption spectrum (CHCl$_3$) $\nu_{max}$ cm$^{-1}$: 3410, 1760, 1677.

Nuclear Magnetic Resonance Spectrum (CDCl$_3$) δ ppm 0.09 (6H, singlet); 0.88 (9H, singlet); 1.20 (3H, doublet, J=6.5 Hz); 2.29 (3H, singlet); 1.5–2.5 (2H, multiplet); 2.7–3.0 (2H, multiplet); 3.3–4.4 (8H, multiplet); 5.18 (2H, singlet); 6.27 (1H, broad singlet); 7.52 (2H, doublet); 8.17 (2H, doublet).

EXAMPLE 10(b)

(3S, 4R)-3-[(R)-1-t-Butyldimethylsilyloxyethyl]-1-(p-nitrobenzyloxyethyl)-4-([(S)-1-[N-(p-nitrobenzyloxycarbonyl)acetimidoyl]pyrrolidin-3-ylthio]-carbonylmethyl)-2-azetidinone 185 mg (0.31 mmole) of (3S, 4R)-3-[(R)- 1-t-butyldimethylsilyloxyethyl]-4-([(S)-1-[N-(p-nitrobenzyloxycarbonyl)acetimidoyl]pyrrolidin-3-ylthio] carbonylmethyl)-2-azetidinone were dissolved in 5 ml of tetrahydrofuran. To the solution was added dropwise 0.20 ml (0.32 mmole) of a 15% w/v butyllithium in hexane solution, under a nitrogen atmosphere at −78° C. with stirring. The mixture was stirred for 2 minutes at the same temperature, and then 120 mg (0.49 mmole) of p-nitrobenzyloxyethyl chloride were added, and the reaction solution was stirred for 4 minutes. 10 ml of a 0.1M phosphate buffer solution (pH 7.1) were then added to the reaction mixture, after which it was extracted with ethyl acetate. The organic extracts were dried and the crude product obtained after concentration was purified by column chromatography through 6 g of silica gel.

Elution of the column with an 8:1 by volume mixture of benzene and ethyl acetate gave impure material and then elution with mixtures of benzene and ethyl acetate in volume ratios from 4:1 to 3:1 gave 99 mg (yield 45%) of the title product as an oil.

Furthermore, elution with mixtures of benzene and ethyl acetate in volume ratios from 1:2 to 1:5 gave 51 mg (28%) of the starting material.

Infrared absorption spectrum (CHCl$_3$) $v_{max}$ cm$^{-1}$: 1808, 1756, 1689.

Nuclear Magnetic Resonance Spectrum (CDCl$_3$) δ ppm 0.03 (3H, singlet); 0.08 (3H, singlet); 0.82 (9H, singlet); 1.20 (3H, doublet, J=6.5 Hz); 2.29 (3H, singlet); 1.5–2.5 (2H, multiplet); 3.0–4.7 (10H, multiplet); 5.17 (2H, singlet); 5.36 (2H, singlet); 7.51 (2H, doublet); 7.53 (2H, doublet); 8.18 (2H, doublet); 8.22 (4H, doublet).

EXAMPLE 10(c)

p-Nitrobenzyl (5R, 6S)-6-[(R)-1-t-butyldimethylsilyloxyethyl]-2-[(S)-1-[N-(p-nitrobenzyloxycarbonyl)acetimidoyl]pyrrolidin-3-ylthio]carbapen-2-em-3-carboxylate.

99 mg (0.14 mmole) of (3S, 4R)-3-[(R)-1-t-butyldimethylsilyloxyethyl]-1-(p-nitrobenzyloxyethyl)-4-([(S)-1-[N-(p-nitrobenzyloxycarbonyl)acetimidoyl]pyrrolidin-3-yl thio]carbonylmethyl)-2-azetidinone, 139 mg (0.84 mmole) of triethyl phosphate and 4 mg (0.04 mmole) of hydroquinone were dissolved in 10 ml of toluene, and the solution was heated at 95° C. for 24 hours under a nitrogen atmosphere. The solvent was then distilled off and the residue was purified by preparative silica gel thin layer chromatography (developing solvent: a 3:1 by volume mixture of benzene and ethyl acetate), to afford 71 mg (yield 75%) of the title product as an oil.

Infrared absorption spectrum (CHCl$_3$) $v_{max}$ cm$^{-1}$: 1773, 1690 (shoulder).

Nuclear Magnetic Resonance Spectrum (CDCl$_3$) δ ppm 0.09 (6H, singlet); 0.88 (9H, singlet); 1.23 (3H, doublet, J=6 Hz); 2.28 (3H, singlet); 1.5–2.5 (2H, multiple); 2.9–4.5 (10H, multiplet); 5.16 (2H, singlet); 5.17 (1H, doublet, J=14 Hz); 5.40 (1H, doublet, J=14 Hz); 7.49 (2H, doublet); 7.56 (2H, doublet); 8.15 (4H, doublet).

EXAMPLE 11 p-Nitrobenzyl (5R, 63)-2-[2-(p-nitrobenzyloxycarbonylamino)ethylthio]-6-[(R)-1-trimetaylsilyloxyethyl]-carbapen-2-em-3-carboxylate.

114 mg (0.16 mmole) of (3S, 4R)-4-([2-(p-nitrobenzyloxycarbonylamino)ethylthio]carbonylmethyl)-1-(p-nitrobenzyloxyethyl)-3-[(R)-1-trimetaylsilyloxyethyl]-2-azetidinone, 164 mg (0.99 mmole) of triethyl phosphite and 3 mg (0.03 mmole) of hydroquinone were dissolved in 15 ml of toluene, and the solution was heated at 100° C. for 24 hours, under a nitrogen atmosphere. After completion of the reaction, the solvent was distilled off under reduced pressure and the residue was purified using Lobar column chromatography (eluent: a 2:1 volume mixture of benzene and ethyl acetate), to give 43 mg (yield 40%) of the title product as a solid. This was recrystallized from benzene-hexane as crystals melting at 105°–106° C.

Infrared absorption spectrum (CHCl$_3$) $v_{max}$ cm$^{-1}$: 1773, 1718, 1700 (shoulder).

Nuclear Magnetic Resonance Spectrum (CDCl$_3$) δ ppm 0.14 (9H, singlet); 1.26 (3H, doublet, J=6 Hz); 2.8–3.7 (7H, multiplet); 3.9–4.5 (2H, multiplet); 5.15 (2H, singlet); 5.18 (1H, doublet, J=14 Hz); 5.44 (1H, doublet, J=14 Hz); about 5.3 (1H, broad singlet); 7.43 (2H, doublet); 7.59 (2H, doublet); 8.17 (4H, doublet).

EXAMPLE 12(a)

(3S, 4R)-3-[(R)-1-(p-Nitrobenzyloxycarbonyloxy)ethyl]-4-([(S)-1-(p-nitrobenzyloxycarbonyl)pyrrolidin-3-ylthio]-carbonylmethyl)-1-(p-nitrobenzyloxyethyl )-2-azetidinone 182 mg (0.295 mmole) of (3S, 4R)-3-[(R)-1-(p-nitrobenzyloxycarbonyloxy)ethyl]-4-([(S)-1-(p-nitrobenzyloxycarbonyl)pyrrolidin-3-ylthio]carbonylmethyl)-2-azetidinone were dissolved in 10 ml of methylene chloride. To this solution were added successively 110 mg (0.98 mmole) of 1,4-diazabicyclo[2,2,2]octane and 450 mg (1.85 mmole) of p-nitrobenzyloxyethyl chloride, at 0° C. with stirring. After 1 hour, the reaction mixture was poured into 40 ml of a 0.1M phosphate buffer solution (pH 7) and extracted with methylene chloride. The organic extracts were washed with a saturated aqueous solution of sodium chloride and dried. The solvent was distilled off. The resulting residue was purified by column chromatography through 5 g of silica gel, eluted with 10% to 17.5% by volume solutions of ethyl acetate in benzene, to afford 169 mg (yield 69.5%) of the title product in the form of an oil.

Infrared absorption spectrum (CHCl$_3$) $v_{max}$ cm$^{-1}$: 1805, 1745, 1695, 1690 (shoulder).

Nuclear Magnetic Resonance Spectrum (CDCl 3) δ ppm 1.42 (3H, doublet, J=6.5 Hz); 1.5–2.5 (2H, multiplet); 2.7–4.2 (9H, multiplet); about 4.5 (1H, multiplet); 5.17 (2H, singlet); 5.20 (2H, singlet); 5.36 (2H, singlet); 7.47 (4H, doublet); 7.52 (2H, doublet); 8.18 (6H, doublet).

EXAMPLE 12(b)

p-Nitrobenzyl (5R, 6S)-6-[(R)-1-(p-nitrobenzyloxycarbonyloxy)ethyl]-2-[S)-1-(p-nitrobenzyloxycarbonyl) -pyrrolidin-3-yl thiocarbapen-2-em-3-carboxylate.

128 mg (0.155 mmole) of (3S, 4R)-3-[(R)-1-(p-nitrobenzyloxycarbonyloxy)ethyl]-4-([(S)-1-(p-nitrobenzyloxycarbonyl)pyrrolidin-3-ylthio]carbonylmethyl)-1-(p-nitrobenzyloxyethyl)-2-azetidinone, 155 mg (0.934 mmole) or triethyl phosphite and 7 mg (0.06 mmole) of hydroquinone were dissolved in 13 ml of toluene, and the solution was heated at 90° C. for 1.5 hours, under a nitrogen atmosphere. After completion of the reaction, the solvent and excess triethyl phosphite were distilled off under reduced pressure and the resulting residue was dissolved in 13 ml of toluene and heated at 100° C. for 80 hours under a nitrogen atmosphere. The solvent was distilled off and the residue was purified using Lobar column chromatography (eluent: a 1:1 by volume mixture of ethyl acetate and benzene), to give 69.6 mg (yield, 56.6%) of the desired product in the form of an oil.

Infrared absorption spectrum (CHCl$_3$) $v_{max}$ cm$^{-1}$: 1778, 1745, 1695, 1690 (shoulder).

Nuclear Magnetic Resonance Spectrum (CDCl$_3$) δ ppm 1.47 (3H, doublet, J=6 Hz); 1.7–2.7 (2H, multiplet); 2.9–4.5 (10H, multiplet); 5.18 (2H, singlet); 5.21 (2H, singlet); 5.19 (1H, doublet, J=14 Hz); 5.45 (1H, doublet, J=14 Hz); 7.47 (4H, doublet); 7.58 (2H, doublet); 8.17 (6H, doublet).

EXAMPLE 13(a)

(3R, 4R)-4-Acetoxy-3-[(R)-1-t-butyldimethylsilyloxyethyl]-1-trimethylsilyl-2-azetidinone To an ice-cooled solution of 50g (0.174 mole) of (3R, 4R)-4-acetoxy-3-[(R)-1-t-butyldimethylsilyloxyethyl]-2-azetidinone and 24.69 (0.244 mole) of triethylamine in 500 ml of tetrahydrofuran were added 26.5g (0.244 mole) of trimethylchlorosilane under a nitrogen stream. The reaction temperature was allowed to rise to room temperature and the reaction mixture was stirred for 2 hours. The precipitate was filtered off using a Celite (trade mark) filter aid. After the precipitate had been washed with ether twice, the filtrate and the washings were combined, and the solvent was evaporated. The residue was washed with ether to filter off the insoluble materials, Evaporation of the solvent from the filtrate gave 6.23 g (yield 100%) of the title compound as a semi-solid.

Infrared absorption spectrum (Nujol) $v_{max}$ cm$^{-1}$: 1770, 1745.

Nuclear Magnetic Resonance Spectrum (CDCl$_3$) δ ppm 0.06 (6H, singlet); 0.26 (9H, singlet); 0.85 (9H, singlet); 1.19 (3H, doublet, J=6 Hz); 2.03 (3H, singlet); 3.07 (1H, doubled doublet, J=3 & 1 Hz); 4.13 (1H, doubled quartet, J-3 & 6 Hz); 6.04 (1H, doublet, J=1 Hz).

EXAMPLE 13(b)

(3S, 4R)-3-[(R)-1-t-Butyldimethylsilyloxyethyl-4-([(S)-1-(p-nitrobenzyloxycarbonyl)pyrrolidin-3-ylthio] carbonylmethyl)-2-azetidinone 180 mg (0.50 mmole) of (3R, 4R)-4-acetoxy-3-[(R)-1-t-butyldimethylsilyloxyethyl]-1-(trimethylsilyl)-2-azetidinone and 414 mg (1.00 mmole) of (S)-1-(p-nitrobenzyloxycarbonyl)-3-(trimethylsilylacetylthio) pyrrolidine were dissolved in 3 ml of methylene chloride, and then 15 mg (0.07 mmole) of trimethylsilyl trifluoromethanesulphonate were added to the solution and the resulting mixture was allowed to stand at room temperature for 15 hours. After the reaction was completed, the reaction mixture was poured into an aqueous solution of sodium bicarbonate, with stirring. The organic layer was separated, washed with water and dried, and the organic solvent was evaporated. The residue was purified by preparative thin layer chromatography, developed with a 6:1 by volume mixture of chloroform and ethyl acetate. There were obtained 185mg (yield 67%) of a solid material, which on recrystallization from a mixture of hexane and ethyl acetate, gave a purified product melting at 104°–106° C.

Infrared absorption spectrum (CHCl$_3$) $v_{max}$ cm$^{-1}$: 3410, 1775, 1685.

Nuclear Magnetic Resonance Spectrum (CDCl$_3$) δ ppm 0.08 (6H, singlet); 0.88 (9H, singlet); 1.19 (3H, doublet, J=6Hz); 1.7–2.5 (2H, multiplet); 2.7–3.0 (2H, multiplet); 3.53 (2H, triplet, J=7 Hz); 3.2–4.4 (6H, multiplet); 5.19 (2H, singlet); 6.15 (1H, broad singlet); 7.42 (2H, doublet); 8.20 (2H, doublet).

EXAMPLE 13(c)

(33,4R)-3-[(R)-1-t-Butyldimethylsilyloxyethyl]-1-(p-nitrobenzyloxyethyl)-4-([(S)-1-(p-nitrobenzyloxycarbonyl)pyrrolidin-3-ylthio] carbonylmethyl)-2-azetidinone A solution of 57.7mg (0.105 mmole) of (3S, 4R)-3-[(R)-1-t-butyldimethylsilyloxyethyl]-4-([(S)-1-(p-nitrobenzyloxycarbonyl)pyrrolidin-3-ylthio] carbonylmethyl)-2-azetidinone and 33 mg (0.33 mmole) of triethylamine in 3 ml of methylene chloride was ice-cooled, after which 73 mg (0.30 mmole) of p-nitrobenzyloxyethyl chloride were added under a nitrogen stream, and the mixture was stirred for 1 hour. The reaction solution was poured into a 0.1M phosphate buffer solution (pH 7.2), and the organic layer was washed with a saturated aqueous solution of sodium chloride. After evaporation of the solvent, the residue was purified by column chromatography using 1.3 g of silica gel. The eluted fractions obtained with a mixed solvent of benzene and ethyl acetate in volume ratios from 12:1 to 4:1 were collected, and 67.8 mg (yield 83%) of the title compound was obtained as an oil.

Infrared absorption spectrum (CHCl$_3$) $v_{max}$ cm$^{-1}$: 1800, 1754, 1695, 1682.

Nuclear Magnetic Resonance Spectrum (CDCl 3) δ ppm 0.03 (3H, singlet); 0.13 (3H, singlet); 0.85 (9H, singlet); 1.23 (3.4, doublet, J=6 Hz); 1.5–2.5 (2H, multiplet); 3.0–5.0 (10H, multiplet); 5.23 (2H, singlet); 5.43 (2H, singlet); 7.50 (2H, doublet, J=8 Hz); 7.56 (2H, doublet, J=8 Hz); 8.22 (4H, doublet, J=8 Hz).

EXAMPLE 13 (d)

p-Nitrobenzyl (5R, 6S)-6-[(R)-1-t-butyldimethylsilyloxyethyl]-2-[(S)-1-(p-nitrobenzyloxycarbonyl)-pyrrolidin-3-ylthio] carbapen-2-em-3-carboxylate A solution of 190 mg (0.25 mmole) of (3S, 4R)-3-[(R)-1-t-butyldimethylsilyloxyethyl]-1-(p-nitrobenzyloxyethyl)-4-([(S)-1-(p-nitrobenzyloxycarbonyl)pyrrolidin-3-ylthio] carbonylmethyl)-2-azetidinone, 250 mg (1.5 mmole) of triethyl phosphite and 10 mg (0.90 mmole) of hydroquinone in 20 ml of toluene was heated at 95° C. for 15 hours. On thin layer chromatography, disappearance of the starting materials and appearance of 1-(N-methylformimidoyl) pyrrolidin-3-yl, (3S,4R)-3-[(R)-1-t-butyldimethylsilyloxyethyl]-1-[1-(p-nitrobenzyloxycarbonyl)-1-triethoxyphosphoranylidenemethyl]-4-([(S)-1-(p-nitrobenzyloxy-carbonyl)pyrrolidin-3-ylthio] carbonylmethyl)-2-azetidinone and the desired carbapenem compound were observed. The solvent and excess triethyl phosphite were evaporated off under reduced pressure. To the oily residue were added 20 ml of toluene and the mixture was heated at 95° C. For 57 hours to complete the cyclization reaction of the phosphoranylidene compound. After evaporation of the solvent, the residue was purified with a Lobar column. The fraction eluted with a 2:1 by volume mixture of benzene and ethyl acetate was collected and 151.5 mg (yield 83%) of the title compound was obtained as an oil.

Infrared absorption spectrum (CHCl$_3$) $v_{max}$ cm$^{-1}$: 1770, 1695.

Nuclear Magnetic Resonance Spectrum (CDCl$_3$) δ ppm: 0.07 (6H, singlet); 0.87 (9H, singlet); 1.24 (3H, doublet, J=6 Hz); 1.6–2.8 (2H, multiplet); 2.8–4.5 (10H, multiplet); 5.14 (1H, doublet, J=14 Hz); 5.18 (2H, singlet); 5.41 (1H, doublet, J=14 Hz); 7.46 (2H, doublet, J=9 Hz); 7.61 (2H, doublet, J=9 Hz); 8.17 (4H, doublet, J=9 Hz).

EXAMPLE 14(a)(i)

(3S, 4R)-3-[(R)-1-(p-Nitrobenzyloxycarbonyloxy) ethyl]-4-[(phenylthio)carbonylmethyl]-2-azetidinone To a solution of 448 mg of (3S, 4S)-3-[(R)-1-(p-nitrobenzyloxycarbonyloxy)ethyl]-4-[(phenylthio)ethynyl]-2-azetidinone in 5 ml of anhydrous methylene chloride was added, under an atmosphere of nitrogen gas, 0.4 ml of trifluoroacetic acid, with stirring and ice-cooling. Stirring was continued for 30 minutes under ice-cooling and for a further 1.5 hours at room temperature. The reaction mixture was then poured into a mixture of 1.0 g of sodium bicarbonate, 10 ml of water and 20 ml of ethyl acetate. The mixture was saturated with sodium chloride and the organic layer was separated. The aqueous layer was extracted twice with ethyl acetate. The organic layer and the ethyl acetate extracts were combined, and the combined solution was washed successively with an aqueous solution of sodium bicarbonate and a saturated aqueous solution of sodium chloride and dried over anhydrous magnesium sulphate. The solvent was distilled off under reduced pressure and the residue was subjected to column chromatography through silica gel, eluted with a 1:1 by volume mixture of cyclohexane and ethyl acetate, to afford 95.0 mg (yield 63.0%) of the title thioester compound, as a viscous oil.

Infrared absorption spectrum (CHCl$_3$) $\nu_{max}$ cm$^{-1}$: 1770.

Nuclear Magnetic Resonance Spectrum (CDCl$_3$) δ ppm: 1.43 (3H, doublet, J=6 Hz), 2.9–3.3 (3H, multiplet); 3.8–4.2 (1H, multiplet), 4.7–5.4 (1H, multiplet); 5.13 (2H, singlet); 6.40 (1H, broad singlet); 7.33 (5H, singlet); 7.75 (4H, A$_2$B$_2$-quartet, Δδ=44 Hz, J=9 Hz). Mass Spectrum m/e : 444 (M$^+$)

EXAMPLE 14(a)(ii)

(3S, 4R)-3-[(R)-1-(p-Nitrobenzyloxycarbonyloxy) ethyl]-1-(p-nitrobenzyloxyethyl)-4-[(phenylthio) carbonylmethyl]-2-azetidinone 1.00 g (2.25 mmole) of (3S, 4R)-3-[(R)-1-(p-nitrobenzyloxycarbonyloxy)ethyl]-4-[(phenylthio)carbonylmethyl]-2-azetidinone was dissolved in 20 ml of methylene chloride. To the solutiion were added 350 mg (2.71 mmole) of diisopropylethylamine and then 660 mg (2.71 mmole) of p-nitrobenzyloxyethyl chloride, with stirring at 0° C. After 15 minutes, a further 230 mg (1.78 mmole) of diisopropylethylamine and 433 mg (1.78 mmole) of p-nitrobenzyloxyethyl chloride were added, and the mixture was stirred at that temperature for 15 minutes. After completion of the reaction, 30 ml of a 0.1M phosphate buffer solution (pH 7.1) was added to the reaction mixture and the organic layer was separated. The aqueous lager was extracted with chloroform. The organic layer was combined with the chloroform extract and then the solvent was distilled from the mixture. The residue was dissolved in 50 ml of a 1:1 by volume mixture of benzene and ethyl acetate, washed successively with 0.02N hydrochloric acid, water, a 5% w/v aqueous solution of sodium bicarbonate and a saturated aqueous solution of sodium chloride and dried over anhydrous magnesium sulphate. The solvent was distilled off, to afford 1.47 g (yield 100%) of the title product as crystals which were recrystallized from a mixture of benzene and ethyl acetate, to afford the pure product melting at 129°–130° C.

EXAMPLE 14(b)(i)

(3S, 4R)-3-[(R)-1-t-butyldimethylsilyloxyethyl]-1-[(R)-2-methyl-1-(p-nitrobenzyloxycarbonyl)prop-2-ethyl]-4-[(phenylthio)carbonylmethyl]-2-azetidinone 83 mg (0.160 mmole) of (3R, 4RS)-4-acetoxy-3-[(R)-1-t-butyldimethylsilyloxyethyl]-1-[(R)-1-(p-nitrobenzyloxycarbonyl)-2-methylpropyl-2-enyl]-2-azetidinone and 54 mg (0.24 mmole) of 1-phenylthio-l-(trimethylsilyloxy)-ethylene were dissolved in 3 ml of dry methylene chloride. To the solution were added 6 mg (0.025 mmole) of trimethylsilyl trifluoromethanesulphonate and the mixture was left to stand in an atmosphere of nitrogen gas for 72 hours. After completion of the reaction, the reaction mixture was poured into a dilute aqueous solution of sodium bicarbonate and extracted with chloroform. The chloroform was distilled from the extract and the residue was subjected to thin layer chromatography using silica gel developed with a 4:1 by volume mixture of hexane and acetic acid, to afford 86 mg (yield 88%) of the title product.

Infrared absorption spectrum (CHCl$_3$) $\nu_{max}$ cm$^{-1}$: 1750 (shoulder), 1740, 1695.

Specific rotation [α]$^{25}$–50° (C=1.04, chloroform).

Nuclear Magnetic Resonance Spectrum (CDCl$_3$) δ ppm: 0.03 (3H, singlet); 0.06 (3H, singlet); 0.85 (9H, singlet); 1.18 (3H, doublet, J=6 Hz); 1.85 (3H, broad singlet); 2.86 (1H, doubled doublet, J=15 & 7 Hz); 3.00 (1H, doubled doublet, J=5 & 2.5 Hz); 3.20 (1H, doubled doublet, J15 & 5.5 Hz); 3.9–4.6 (2H, multiplet); 4.78 (1H, singlet); 4.87 (1H, broad singlet); 5.02 (1H, broad); 5.20 (2H, singlet); 7.36 (5H, singlet); 7.45 (2H, doublet); 8.16 (2H, doublet).

EXAMPLE 14(b)(ii)

(3S, 4R)-3-[(R)-1-Hydroxyethyl]-1-[2-methyl-1-(p-nitrobenzyloxycarbonyl)prop-1-enyl]-4-[(phenylthio)carbonylmethyl]-2-azetidinone 64 mg (0.104 mmole) of (3S, 4R)-3-[(R)-1-t-butyldimethylsilyloxyethyl]-1-[(R)-2-methyl-1-(p-nitrobenzyloxycarbonyl)prop-2-enyl]-4-[(phenylthio)-carbonylmethyl]-2-azetidinone were dissolved in 1.5 ml of acetonitrile. To the solution were added, with stirring at –15° C., 15 mg (0.106 mmole) of boron trifluoride etherate. After 30 minutes, the reaction mixture was diluted with ethyl acetate and washed with a dilute aqueous solution of sodium bicarbonate. The solvent was distilled off under reduced pressure and the resulting residue was subjected to thin layer chromatography using silica gel, developed with a 2:3 by volume mixture of benzene and ethyl acetate, to afford 48 mg (yield 92%) of the title product.

Infrared absorption spectrum (CHCl$_3$) $\nu_{max}$ cm$^{-1}$: 3480, 1748, 1720 (shoulder), 1700 (shoulder), 1625.

Nuclear Magnetic Resonance Spectrum (CDCl$_3$) δ ppm: 1.26 (3H, doublet, J=6.5 Hz); 1.99 (3H, singlet); 2.23 (3H, singlet); about 2.95 (1H, multiplet); 2.97 (2H, doublet, J=6.5 Hz); 3.9–4.5 (2H, multiplet); 5.24 (2H, singlet); 7.35 (5H, broad singlet); 7.49 (2H, doublet); 8.17 (2H, doublet).

EXAMPLE 14(b)(iii)

(3S, 4R)-1-[2-methyl-1-(p-nitrobenzyloxycarbonyl) prop-1-enyl]-3-[(R)-1-(p-nitrobenzyloxycarbonyloxy)ethyl]-4-[(phenylthio) carbonylmethyl]-2-azetidinone 44 mg (0.088 mmole) of (3S, 4R)-3-[(R)-1-hydroxyethyl]-1-[2-methyl-1-(p-nitrobenzyloxycarbonyl)prop-1-enyl]-4-[(phenylthio)carbonylmethyl]-2-azetidinone were dissolved in 2 ml of methylene chloride. To the solution were added 32 mg (0.26 mmole) of 4-(N,N-dimethylamino) pyridine and 57 mg (0.26 mmole) of p-nitrobenzyloxycarbonyl chloride, with stirring at 0° C. The mixture was stirred at that temperature for 3 hours, after which it was poured into a dilute aqueous solution of sodium bicarbonate and extracted with chloroform. The chloroform extract was washed successively with dilute hydrochloric acid and a dilute aqueous solution of sodium bicarbonate and dried over anhydrous magnesium sulphate. The solvent was then distilled off. The residue was subjected to thin layer chromatography using silica gel developed with a 3:1 by volume mixture of benzene and ethyl acetate, to afford 21 mg (yield 35%) of the title product as an oil.

Infrared absorption spectrum (CHCl$_3$) $\nu_{max}$ cm$^{-1}$: 1756, 1720 (shoulder), 1700 (shoulder), 1625.

Nuclear Magnetic Resonance Spectrum (CDCl$_3$) δ ppm: 1.41 (3H, doublet, J=6.5 Hz); 1.96 (3H, singlet); 2.23 (3H, singlet); 2.91 (2H, doublet, J=6.5 Hz); 3.11 (1H, doubled doublet, J=8.5 & 2.5 Hz); 4.31 (1H, tripled doublet, J=6.5 & 2.5 Hz); 5.08 (2H, singlet); 5.23 (2H, singlet); 5.1 (1H, multiplet); 7.32 (5H, singlet); 7.39 (2H, doublet); 7.49 (2H, doublet); 8.15 (4H, doublet).

EXAMPLE 14(b) (iv)

(3S, 4R)-3-[(R)-1-(p-Nitrobenzyloxycarbonyloxy) ethyl]-1-(p-nitrobenzyloxyethyl)-4-[(phenylthio) carbonylmethyl]-2-azetidinone Ozone was bubbled through a solution of 97 mg of (3S, 4R)-1-[2-methyl-1-(p-nitrobenzyloxycarbonyl)prop-1-enyl]-3-[(R)-1-(p-nitrobenzyloxycarbonyloxy)ethyl]-4-[(phenylthio)carbonylmethyl]-2-azetidinone in 10 ml of methylene chloride at −78° C. After the reaction mixture had turned blue, nitrogen gas was bubbled through the mixture to drive out the excess ozone. 0.1 ml of dimethyl sulphide was then added to the reaction mixture and its temperature was elevated to room temperature over about 5 minutes. The mixture was then concentrated by evaporation under reduced pressure. The residue was dissolved in benzene, washed twice with water and dried. The solvent was distilled off, to afford 93 mg (yield 100%) of the title product as a solid, which was recrystallized from a mixture of benzene and ethyl acetate to afford the pure product melting at 129°–130° C.

Elemental Analysis Calculated for $C_{30}H_{25}O_{12}N_3S$: C, 55.30%; H, 3.87%; N, 6.45%; S, 4.92%. Found: C, 55.49%; H, 3,92%; N, 6.30%; S, 4.87%.

Infrared absorption spectrum (Nujol) $v_{max}$ cm$^{-1}$: 1810, 1748, 1728, 1700, 1690 (shoulder).

Specific rotation $[\alpha]^{25}$ −48° (C=1.02, chloroform).

Nuclear Magnetic Resonance Spectrum (CDCl$_3$) δ ppm: 1.43 (3H, doublet, J=6.5 Hz); 3.12 (1H, doubled doublet, J=16 & 8 Hz); 3.53 (1H, doubled doublet, J=16 & 4 Hz); 3.66 (1H, doubled doublet, J=7 & 3.5 Hz); 4.55 (1H, multiplet); 5.11 (2H, singlet); 5.35 (2H, singlet); about 5.2 (1H, multiplet); 7.52 (4H, doublet); 8.12 (2H, doublet); 8.16 (2H, doublet).

EXAMPLE 14(c)

(3S, 4R)-3-[(R)-1-(p-Nitrobenzyloxycarbonyloxy) ethyl]-1-[1-(p-nitrobenzyloxycarbonyl)-1-triisopropoxyphosphoranylidenemethyl]-4-[(phenylthio)carbonylmethyl]-2-azetidinone 147 mg (0.225 mmole) of (3S, 4R)-3-[(R)-1-(p-nitrobenzyloxycarbonyloxy)ethyl]-1-(p-nitrobenzyloxyethyl)-4-[(phenylthio)carbonylmethyl]-2-azetidinone and 234 mg (1.13 mmole) of triisopropyl phosphate were dissolved in 3 ml of benzene, and then the mixture was stirred in a stream of a nitrogen gas at 70° C. For 1.5 hours. The solvent was then distilled off and the resulting residue was subjected to chromatography using a Lobar column A (a product of E. Merck Co.), eluted with a 3:1 by volume mixture of benzene and ethyl acetate, to afford 161 mg (yield 85%) of the title compound as an oily substance.

Infrared absorption spectrum (CHCl$_3$) $v_{max}$ cm$^{-1}$: 1748, 1700, 1630.

EXAMPLE 15(a)

(3S, 4R)-3-[(R)-1-Hydroxyethyl]-4-( [2-(p-nitrobenzyloxycarbonylamino)ethylthio] carbonylmethyl)-1-[-(1-(p-nitrobenzyloxycarbonyl)-2-methyl-l-propenyl]-2-azetidinone To a solution of 150 mg (0.198 mmole) of (3S, 4R)-3-[(R)-1-t-butyldimethylsilyloxyethyl]-4-([2-(p-nitrobenzyl-oxycarbonylamino)ethylthio]carbonylmethyl)-1-[2-methyl-1-(p-nitrobenzyloxycarbonyl)prop-1-enyl]-2-azetidinone in 5 ml of acetonitrile were added 28 mg (0.197 mmole) of boron trifluoride etherate, with stirring and ice-cooling. After 20 minutes, the reaction mixture was diluted with 10 ml of ethyl acetate, washed with an aqueous solution of sodium bicarbonate and dried. The solvent was distilled off, to afford 125 mg (yield 98%) of the title product, as an oily substance.

Infrared absorption spectrum (CHCl$_3$) $v_{max}$ cm$^{-1}$: 3450, 3400, 1747, 1720, 1700 (shoulder), 1680.

Nuclear Magnetic Resonance Spectrum (CDCl$_3$) δ ppm: 1.25 (3H, doublet, J=6 Hz); 1.94 (3H, singlet); 2.18 (3H, singlet); 2.5–3.6 (7H, multiplet); 3.8–4.5 (2H, multiplet); 5.13 (2H, singlet); 5.22 (2H, singlet); 5.4 (1H, broad singlet); 7.42 (2H, doublet); 7.50 (2H, doublet); 8.14 (4H, doublet).

EXAMPLE 15(b)

(3S, 4R)-4-([2-(p-Nitrobenzyloxycarbonylamino) ethylthio]carbonylmethyl)-1-[2-methyl-1-(p-nitrobenzyloxycarbonyl)prop-1-enyl]-3-[(R)-1-(p-nitrobenzyloxycarbonyloxy)ethyl]-2-azetidinone 125 mg (0.194 mmole) of (3S, 4R)-3-[(R)-1-hydroxyethyl]-4-([2-(p-nitrobenzyloxycarbonylamino) ethylthio]-carbonylmethyl)-1-[2-methyl-1-(p-nitrobenzyloxycarbonyl)-prop- 1-enyl]-2-azetidinone were dissolved in 4 ml of methylene chloride. To the solution were added, in turn, 71 mg (0.58 mmole) of 4-(N,N-dimethylamino)-pyridine and 126 mg (0.58 mmole) of p-nitrobenzyloxy-carbonyl chloride, with stirring at 0° C. The reaction mixture was then stirred at room temperature for 1 hour, after which it was diluted with methylene chloride and washed with a saturated aqueous solution of sodium chloride. The solvent was distilled off and the residue was subjected to chromatography using a Lobar column B eluted with a 2:3 by volume mixture of hexane and ethyl acetate, to afford 82 mg (yield 51%) of the title product as an oily substance. Infra-red and nuclear magnetic resonance spectra of the product agreed with those of the product of Preparation 7.

EXAMPLE 15(c)

(3S, 4R)-4-([2-(p-Nitrobenzyloxycarbonylamino) ethyl-thiolcarbonylmethyl)-3-[(R)-1-(p-nitrobenzyloxycarbonyloxy)ethyl]-1-(p-nitrobenzyloxyethyl)-2-azetidinone 31 mg of (3S, 4R)-4-([2-(p-nitrobenzyloxycarbonyl-amino)-ethylthio]carbonylmethyl)-1-[2-methyl-1-(p-nitrobenzyloxycarbonyl)prop-1-enyl]-3-[(R)-1-(p-nitrobenzyloxycarbonyloxyethyl]-2-azetidinone were dissolved in 15 ml of methylene chloride, and ozone was bubbled through the solution at −78° C. For 5 minutes. The mixture was then left to stand at that temperature for 15 minutes, after which nitrogen gas was bubbled through the mixture to drive out the excess ozone. 50 mg of dimethyl sulphide were added to the reaction mixture, which was then warmed to room temperature over 10 minutes. The solvent was distilled off and the residue was dissolved in benzene, washed twice with water and dried. The solvent was distilled off under reduced pressure, to afford 27 mg (yield 90%) of the title product as an oily substance.

Infrared absorption spectrum (CHCl$_3$) $v_{max}$ cm$^{-1}$: 1808, 1749, 1718 (broad), 1700 (shoulder), 1682 (shoulder).

Nuclear Magnetic Resonance Spectrum (CDCl$_3$) δ ppm: 1.40 (3H, doublet, J=6.5 Hz); 2.7–3.7 (7H, multiplet); 4.5 (1H, multiplet); 5.13 (2H, singlet); 5.19 (2H, singlet); 5.35 (2H, singlet); 4.9–5.4 (2H, multiplet); 7.43 (2H, doublet); 7.46 (2H, doublet); 7.50 (2H, doublet); 8.15 (2H, doublet); 8.17 (4H, doublet).

EXAMPLE 15(d)

(3S, 4R)-4-([2-(p-Nitrobenzyloxycarbonylamino) ethylthio]carbonylmethyl)-3-[(R)-1-(p-nitrobenzyloxycarbonyl-thio]carbonyloxy)ethyl]-1-[1-(p-nitrobenzyloxycarbonyl)-1-triisopropoxyphosphoranylidenemethyl]-2-azetidinone A mixture of 165 mg (0.207 mmole) of (3S, 4R)-4-([2-(p-nitrobenzyloxycarbonylamino)ethylthio]carbonyl-methyl)-3-[(R)-1-(p-nitrobenzyloxycarbonyloxy)ethyl]-1-(p-nitrobenzyloxyethyl)-2-azetidinone and 215 mg (1.04 mmole) of triisopropyl phosphite in 3 ml of toluene was stirred at 80° C. in a stream of a nitrogen gas for 1.5 hours. The solvent was then distilled off and the residue was subjected to chromatography using a Lobar column A (product of E. Merck Co.), eluted with a 1:1 by volume mixture of benzene and ethyl acetate, to give 182 mg (yield 89%) of the title product as an oil substance.

Infrared absorption spectrum (CHCl$_3$) $v_{max}$ cm$^{-1}$: 3450, 1745 (broad), 1682, 1632.

EXAMPLE 15(e)

p-Nitrobenzyl (5R, 6S)-2-[2-(p-nitrobenzyloxycarbonylamino)ethylthio]-6-[(R)-1-(p-nitrobenzyloxycarbonyloxy)ethyl]carbapen-2-em-3-carboxylate.

A mixture of 48 mg of (3S, 4R)-4-([2-(p-nitrobenzyloxycarbonylamino)ethylthio]carbonylmethyl)-3-[(R)-1-(p-nitrobenzyloxycarbonyloxy)ethyl]-1-[1-(p-nitrobenzyloxycarbonyl)-1-triisopropoxy-phosphoranylidenemethyl]-2-azetidinone and 30 mg of hydroquinone in 5 ml of xylene was heated at 120° C. under a stream of a nitrogen gas for 13 hours. The xylene was then distilled off and the residue was subjected to chromatography using a Lobar column A eluted with a 2:1 by volume mixture of chloroform and ethyl acetate, to give crude crystals, which were recrystallized from a mixture of benzene and ethyl acetate, affording 19 mg (yield 51%) of colourless prisms, melting at 148°–150° C.

Elemental Analysis Calculated for C$_{34}$H$_{31}$O$_{16}$N$_5$S: C, 53.33%; H, 4.08%; N, 9.15%; S, 4.19%.

Found: C, 53.19%; H, 4.07%; N, 9.13%; S, 4.43%.

Infrared absorption spectrum (CHCl$_3$) $v_{max}$ cm$^{-1}$: 3450, 1780, 1740 (shoulder), 1718, 1700 (shoulder). Specific Rotation [α]$^{25}$+66° (C=0.81, chloroform).

Nuclear Magnetic Resonance Spectrum (CDCl$_3$) δ ppm: 1.47 (3H, doublet, J=6 Hz); 2.7–3.7 (7H, multiplet); 4.20 (1HZ, multiplet); about 5.1 (1H, multiplet); 5.16 (2H, singlet); 5.22 (2H, singlet); 5.18 (1H, doublet, J=14 Hz); 5.47 (1H, doublet, J=14 Hz); 7.45 (2H, doublet); 7.49 (2H, doublet); 7.60 (2H, doublet); 8.20 (6H, doublet).

EXAMPLE 16(a)(i)

(3S, 4R)-3-[(R)-1-Hydroxyethyl]-4-([(S)-1-[N-(p-nitrobenzyloxycarbonyl)acetimidoyl]pyrrolidin-3-ylthio]carbonylmethyl)-1-[2-methyl-1-(p-nitrobenzyloxycarbonyl)prop-1-enyl]2-azetidinone.

511 mg (0.62 mmole) of (3S, 4R)-3-[(R)-1-t-butyldimethylsilyloxyethyl]-4-([(S)-1-[N-(p-nitrobenzyloxycarbonyl)acetimidoyl]pyrrolidin-3-ylthio] carbonylmethyl)-1-[2-methyl-1-(p-nitrobenzyloxy-carbonyl)prop-1-enyl]-2-azetidinone were dissolved in 20 ml of acetonitrile. To this solution were added 176 mg (1.24 mmole) of boron trifluoride etherate, with stirring and ice-cooling. The reaction mixture was then left to stand at room temperature for 2.5 hours, after which it was diluted with ethyl acetate, washed with an aqueous solution of sodium bicarbonate and dried. The solvent was distilled off, to afford 462 mg of the title product.

Infrared absorption spectrum (CHCl$_3$) $v_{max}$ cm$^{-1}$: 3500, 1749, 1718, 1674.

Nuclear Magnetic Resonance Spectrum (CDCl$_3$) δ ppm: 1.24 (3H, doublet, J =6 Hz); 1.94 (3H, singlet); 2.19 (3H, singlet); 2.28 (3H, singlet); 1.7–2.5 (2H, multiplet); 2.87 (2H, doublet, J=6.5 Hz); 3.1–4.5 (8H, multiplet); 5.15 (2H, singlet); 5.22 (2H, singlet); 7.49 (2H, doublet); 7.51 (2H, doublet); 8.13 (2H, doublet); 8.17 (2H, doublet).

EXAMPLE 16(a)(ii)

(3S, 4R)-4-([(S)-1-[N-(p-Nitrobenzyloxycarbonyl) acetimidoyl]pyrrolidin-3-ylthio]carbonylmethyl)-1-(2-methyl-1-(p-nitrobenzyloxycarbonyl)prop-1-enyl]-3-[(R)-1-(p-nitrobenzyloxycarbonyloxy)ethyl]-2-azetidinone 56 mg (0.079 mmole) of (3S, 4R)-3-[(R)-1-hydroxy-ethyl]-4-([(S)-1-[N-(p-nitrobenzyloxycarbonyl) acetimidoyl]pyrrolidin-3-ylthio]carbonylmethyl)-1-[2-methyl-1-(p-nitrobenzyloxycarbonyl)prop-1-enyl]-2-azetidinone were dissolved in 1.5 ml of methylene chloride. To the solution were added, in turn, 29 mg (0.24 mmole) of 4-(N,N-dimethylamino)pyridine and 51 mg (0.24 mmole) of p-nitrobenzyloxycarbonyl chloride, with stirring at 0° C. The reaction mixture was stirred at room temperature for 3 hours, diluted with methylene chloride, washed with an aqueous solution of sodium chloride and dried over anhydrous magnesium sulphate. The solvent was distilled off and the residue was subjected to thin layer chromatography using silica gel, developed with a 1:5 by volume mixture of hexane and ethyl acetate, to afford 30 mg (yield 42%) of the title product as an oily substance. 8 mg (14%) of the starting material was also recovered.

Infrared absorption spectrum (CHCl$_3$) $v_{max}$ cm$^{-1}$: 1756, 1720 (shoulder), 1677.

Nuclear Magnetic Resonance Spectrum (CDCl$_3$) δ ppm: 1.41 (3H, doublet, J=6 Hz); 1.94 (3H, singlet); 2.21 (3H, singlet); 2.27 (3H, singlet); 1.7–2.5 (2H, multiplet); 2.81 (2H, doublet, J=6.5 Hz); 3.06 (1H, doubled doublet, J=7.5 & 2 Hz); 3.2–4.1 (5H, multiplet); 4.26 (1H, tripled doublet, J=6.5 & 2 Hz); about 5.1 (1H, multiplet); 5.18 (4H, singlet); 5.23 (2H, singlet); 7.46 (2H, doublet); 7.50 (4H, doublet); 8.13 (2H, doublet); 8.16 (4H, doublet).

EXAMPLE 16(a)(iii)

(3S, 4R)-4-([(S)-1-(N-(p-Nitrobenzyloxycarbonyl) acetimidoyl]pyrrolidin-3-ylthio]carbonylmethyl)-3-[ (R)-1-(p-nitrobenzyloxycarbonyloxy)ethyl]-1[-p-nitrobenzyloxyethyl]-2-azetidinone 34 mg (0.038 mmole) of (3S, 4R)-4-([(S)-1-[N-(p-nitrobenzyloxycarbonyl)acetimidoyl]pyrrolidin-3-ylthio] carbonylmethyl)-1-[2-methyl-1-(p-nitrobenzyloxycar-bonyl)-prop-1-enyl]-3-[(R)-1-(p-nitrobenzyloxy-carbonyloxy)ethyl]-2-azetidinone were dissolved in 10 ml of methylene chloride. Ozone was bubbled through the solution at −78° C. For 3 minutes. The mixture was then left to stand at that temperature for 10 minutes, after which nitrogen gas was bubbled through to drive out the excess ozone. 50 mg of dimethyl sulphide were then added to the mixture, which was then warmed to room temperature over about 10 minutes and poured into a mixture of ice and water. The chloroform layer was separated, washed with water and dried over anhydrous sodium sulphate. The solvent was distilled off, to afford 33 mg (yield 100%) of the title product as an oily substance.

Infrared absorption spectrum (CHCl$_3$) $\nu_{max}$ cm$^{-1}$: 1810, 1753, 1682 (broad).

Nuclear Magnetic Resonance Spectrum (CDCl$_3$) δ ppm: 1.42 (3H, doublet, J=6.5 Hz); 1.8–2.5 (2H, multiplet); 2.26 (3H, singlet); 2.8–4.2 (8H, multiplet); about 4.5 (1H, multiplet); 5.17 (2H, singlet); 5.21 (2H, singlet); 5.37 (2H, singlet); about 5.2 (lH, multiplet); 7.52 (6H, broad doublet); 8.15 (2H, doublet); 8.19 (4H, doublet).

EXAMPLE 16(b)(i)

(3S, 4R)-3-[(R)-1-(p-Nitrobenzyloxycarbonyloxy) ethyl]-4-[(phenylthio)carbonylmethyl]-2-azetidinone 203 mg (0.36 mmole) of the azetidinone obtained as described in Preparation 9(a) were dissolved in 10 ml of acetone. To the resulting solution were added 3.0 g (15.2 equivalents) of ceric ammonium nitrate in 5 ml of water, with stirring, at room temperature. The mixture was stirred further at room temperature whilst 200 ml of ethyl acetate and 50 ml of water were added thereto. The mixture was then stirred and its pH was adjusted to a value of about 7.0 by the addition of a 5% w/v aqueous solution of sodium bicarbonate. The ethyl acetate layer was separated, washed with 50 ml of a saturated aqueous solution of sodium chloride and dried over anhydrous magnesium sulphate. The magnesium sulphate was filtered off and the ethyl acetate was distilled from the filtrate under reduced pressure. The residue was subjected to Lobar column chromatography, eluted with a 2:1 by volume mixture of cyclohexane and ethyl acetate, to give 119 mg (69.5%) of the desired azetidinone compound.

Infrared absorption spectrum (CHCl$_3$) $\nu_{max}$ cm$^{-1}$: 1770

Nuclear Magnetic Resonance Spectrum (CDCl$_3$) δ ppm: 1.43 (3H, doublet, J=6 Hz); 2.9–3.3 (3H, multiplet); 3.8–4.2 (1H, multiplet); 4.7–5.4 (1H, multiplet); 5.13 (2H, singlet); 6.40 (1H, broad singlet); 7.33 (5H, singlet); 7.75 (4H, A$_2$B$_2$-quartet, Δδ=44 Hz, J=9 Hz).

Mass Spectrum mn/e: 444 (M$^+$).

EXAMPLE 16(b)(ii)

(3S, 4R)-4-([(S)-1-[N-(p-Nitrobenzyloxycarbonyl) acetimidoyl]pyrrolidin-3-ylthio]carbonylmethyl)-3-[(R)-1-(p-nitrobenzyloxycarbonyloxy)ethyl]-2-azetidinone To a solution of 115 mg (0.26 mmole) of the azetidinone obtained as described in Example 16(b)(i) in 5 ml of dry methylene chloride were added 125 mg (0.386 mmole) of (S)-3-mercapto-1-[N-(p-nitrobenzyloxycarbonyl) acetimidoyl]pyrrolidine. To the resulting mixture was added a catalytic amount of triethylamine, with stirring at room temperature, followed by stirring overnight.

After completion of the reaction, the solvent was distilled off and the residue was subjected to chromatography using a Lobar column eluted with ethyl acetate to afford 168 mg (yield 98.0%) of the title azetidinone compound.

Nuclear Magnetic Resonance Spectrum CDCl$_3$) δ ppm 1.42 (3H, doublet, J=6 Hz); 2.28 (3H, singlet); 1.5–2.6 (2H, multiplet); 2.90 (2H, doublet, J=6.5 Hz); 3.05 (1H, broad doublet, J=7 Hz); 3.2–4.2 (6H, multiplet); 4.9–5.3 (lH, multiplet); 5.18 (2H, singlet); 5.22 (2H, singlet); 6.7 (1H, singlet); 7.4–8.3 (8H, multiplet).

EXAMPLE 16(b)(iii)

(3R, 4R)-1-[1-Hydroxy-1-(p-nitrobenzyloxycarbonyl)methyl]-4-([(S)-1-[N-(p-nitrobenzyloxycarbonyl)acetimidoyl]pyrrolidin-3-ylthio]carbonylmethyl)-3-[(R)-1-(p-nitrobenzyloxycarbonyloxy)ethyl]-2-azetidinone A mixture of 950 mg (1.45 mmole) of (3S, 4R)-4-([(S)-1-[N-(p-nitrobenzyloxycarbonyl)acetimidoyl]pyrrolidin-3-ylthio]carbonylmethyl)-3-[(R)-1-(p-nitrobenzyloxy)ethyl]-2-azetidinone, 492 mg (2.17 mmole) of p-nitrobenzyl glycolate hydrate, 9 g of Molecular Sieve 4A and 18 mg (0.17 mmole) of triethylamine in 20 ml of tetrahydrofuran was stirred at room temperature for 3 hours. At the end of this time, the reaction mixture was filtered and the solvent was distilled from the filtrate. The residue was subjected to chromatography using a Lobar column 8 eluted with a 1:5 by volume mixture of benzene and ethyl acetate, to afford 970 mg (yield 77%) of the title product as an oily substance.

Infrared absorption spectrum (CHCl$_3$) $\nu_{max}$ cm$^{-1}$: 3400, 1748, 1675.

Nuclear Magnetic Resonance Spectrum (CDCl$_3$) δ ppm: 1.37 (3H, doublet, J=6.5 Hz); 1.7–2.5 (2H, multiplet); 2.27 (3H, singlet); 2.7–3.2 (3H, multiplet); 3.3–4.3 (6H, multiplet); 5.15 and 5.27 (2H, singlet); 5.19 (4H, singlet); 4.8–5.6 (2H, multiplet); 7.51 (4H, doublet); 7.53 (2H, doublet); 8.17 (2H, doublet); 8.20 (4H, doublet).

EXAMPLE 16(b)(iv)

(3S, 4R)-4-([(S)-1-[N-(p-Nitrobenzyloxycarbonyl) acetimidoyl]pyrrolidin-3-ylthio]carbonylmethyl)-3-[(R)-1-(p-nitrobenzyloxycarbonyloxy)ethyl]-1-[p-nitrobenzyloxyethyl]-2-azetidinone 110 mg (0.87 mmole) of oxalyl chloride were dissolved in 5 ml of methylene chloride. To the solution was added 137 mg (1.75 mmole) of dimethyl sulphoxide under a stream of a nitrogen gas at −780° C. The mixture was then stirred for 10 minutes, after which a solution of 500 mg (0.577 mmole) of (3R, 4R)-1-[1-hydroxy-1-(p-nitrobenzyloxycarbonyl) methyl]-4-([(S)-1-[N-(p-nitrobenzyloxycarbonyl) acetimidoyl]pyrrolidin-3-ylthio]carbonylmethyl)-3-[(R)-1-(p-nitrobenzyloxycarbonyloxy)ethyl]-2-azetidinone was added to the mixture over 2 minutes. The mixture was stirred for 5 minutes and then 250 mg (2.48 mmole) of triethylamine were added thereto and the mixture was stirred for 15 minutes. About 30 ml of a 0.1M phosphate buffer solution (pH 7.1) was added to the mixture, which was then stirred and extracted with methylene chloride. The extract was dried over anhydrous magnesium sulphate and the solvent was distilled off. The residue was quickly subjected to column chromatography through 10 g of silica gel eluted with 2:1 to 1:1 by volume mixtures of benzene and ethyl acetate, to afford 350 mg (yield 70%) of the title product as an oily substance. Infra-red and nuclear magnetic resonance spectra of the product agreed with those of the product obtained as described in Example 16(a)(iii).

EXAMPLE 16(c)

(3S, 4R)-4-([(S)-1-[N-(p-Nitrobenzyloxycarbonyl) acetimidoyl]pyrrolidin-3-ylthio]carbonylmethyl)-3-[(R)-1-(p-nitrobenzyloxycarbonyloxy)ethyl]-1-[1-(p-nitrobenzyloxycarbonyl)-1-triisopropoxyphosphoranylidenemethyl]-2-azetidinone 430 mg (0.497 mmole) of (3S, 4R)-4-([(S)-1-[N-(p-nitrobenzyloxycarbonyl)acetimidoyl]pyrrolidin-3-ylthio]- carbonylmethyl)-3-[(R)-1-(p-nitrobenzyloxycarbonyloxy)-ethyl]-1-(p-nitrobenzyloxyethyl)-2-azetidinone and 517 mg (2.49 mmole) of triisopropyl phosphite were dissolved in 10 ml of toluene. The solution was heated in a stream of a nitrogen gas at 90° C. For 2 hours. The solvent was then distilled off under reduced pressure. The residue was subjected to chromatography using a Lobar column eluted with a 30:10:1 by volume mixture of ethyl acetate, chloroform and methanol, to afford 447 mg (yield 85%) of the title product as an oily substance. Infra-red and nuclear magnetic resonance spectra of the product agreed with those of the product of Example 18.

EXAMPLE 16(d)

p-Nitrobenzyl (5R, 6S)-2-((S)-1-[N-(p-nitrobenzyloxycarbonyl)acetimidoyl]pyrrolidin-3-ylthio)-6-[(R)-1-(p-nitrobenzyloxycarbonyloxy)ethyl]carbapen-2-em-3-carboxylate A mixture of 100 mg of (3S, 4R)-4-([(S)-1-[N-(p-nitrobenzyloxycarbonyl)acetimidoyl]pyrrolidin-3-ylthio]carbonylmethyl)-3-[(R)-1-(p-nitrobenzyloxycarbonyloxy)ethyl]-1-[1-(p-nitrobenzyloxycarbonyl)-1-triisopropoxyphosphoranylidenemethyl]-2-azetidinone and 6 mg of hydroquinone in 10 ml of toluene was heated at 110° C. under a stream of a nitrogen gas for 24 hours. The toluene was then distilled off under reduced pressure and the residue was subjected to liquid chromatography using a Lobar column A eluted with a 10:30:1 by volume mixture of chloroform, ethyl acetate and methanol, to afford 41 mg (yield 52%) of the title product as an oily substance.

Infrared absorption spectrum (CHCl$_3$) v$_{max}$ cm$^{-1}$: 1780, 1744, 1690 (shoulder), 1676.

Specific rotation [α]$^{25}$ +68° (C=0.17, chloroform).

Nuclear Magnetic Resonance Spectrum (CDCl 3) δ ppm: 1.48 (3H, doublet, J=6.5 Hz); 2.31 (3H, singlet); 1.8–2.6 (2H, multiplet); 3.0–4.5 (9H, multiplet); 5.16 (2H, singlet); 5.20 (2H, singlet); 5.14 (1H, doublet, J=14 Hz); 5.43 (1H, doublet, J=14 Hz); about 5.2 (1H, multiplet); 7.50 (4H, doublet); 7.57 (2H, doublet); 8.17 (6H, doublet).

EXAMPLE 16(e)

(5R, 6S)-2-[(S)-1-Acetimidoylpyrrolidin-3-ylthio]-6-[(R)-1-hydroxyethyl]carbapen-2-em-3-carboxylic acid 485 mg of p-nitrobenzyl (5R, 6S)-2-((S)-1-[N-(P-nitrobenzyloxycarbonyl)acetimidoyl]pyrrolidin-3-ylthio)-6-[(R)-1-(p-nitrobenzyloxycarbonyloxy)ethyl]carbapen-2-em-3-carboxylate were dissolved in a mixture of 25 ml of tetrahydrofuran and 25 ml of a 0.1M phosphate buffer solution (pH 7.1). To the solution was added 1.4 g of a 10% w/w palladium-on-charcoal catalyst and the mixture was stirred under a stream of hydrogen gas at atmospheric pressure for 70 minutes. After completion of the reaction, the catalyst was filtered off and 15 ml of the above buffer solution was added to the filtrate. The mixture was washed with ethyl acetate. The aqueous layer was separated and concentrated to above one half of its original volume by evaporation at room temperature under reduced pressure. The concentrate was subjected to column chromatography through 15 ml of HP20 AG resin (a product of Mitsubishi Chemical Industries Co.). Fractions eluted with 3% v/v aqueous acetone were collected and lyophilized, to afford 115 mg (yield 58%) of the title product as a white powder.

Infrared absorption spectrum (KBr) v$_{max}$ cm$^{-1}$: 3400, 1760, 1675.

Nuclear Magnetic Resonance Spectrum (D$_2$O) δ ppm: 1.29 (3H, doublet, J=6.5 Hz); 1.8–2.7 (2H, multiplet); 2.29 (3H, singlet); 3.22 (2H, doublet, J=9.5 Hz); 3.3–4.4 (8H, multiplet).

EXAMPLE 17

(3S, 4R)-4-([2-(p-Nitrobenzyloxycarbonylamino)ethylthio]carbonylmethyl)-3-[(R)-1-(p-nitrobenzyloxycarbonyloxy)ethyl]-1-[1-(p-nitrobenzyloxycarbonyl)-1-triisopropoxyphosphoranylidenemethyl]-2-azetidinone 52 mg (0.062 mmole) of (3S, 4R)-3-[(R)-1-(p-nitrobenzyloxycarbonyloxy)ethyl]-1-[1-(p-nitrobenzyloxycarbonyl)-1-triisopropoxyphosphoranylidenemethyl]-4-[(phenylthio)carbonylmethyl]-2-azetidinone obtained as described in Example 14(c), 32 mg (0.125 mmole) of 2-(p-nitrobenzyloxycarbonylamino)ethanethiol and 13 mg (0.13 mmole) of triethylamine were dissolved in 1 ml of methylene chloride. The solution was left to stand in an atmosphere of nitrogen gas at room temperature for 24 hours. The solvent was then distilled off under reduced pressure and the residue was subjected to liquid chromatography using a Lobar column A eluted with a 1:1 by volume mixture of benzene and ethyl acetate, to afford 48 mg (yield 79%) of the title product as an oily substance.

Infrared absorption spectrum (KBr) v$_{max}$ cm$^{-1}$: 3450, 1745 (broad), 1682, 1632.

Nuclear Magnetic Resonance Spectrum (CDCl$_3$) δ ppm: 1.33 (18H, doublet, J=6 Hz); 1.42 (3H, doublet, J=6 Hz); 2.7–3.5 (7H, multiplet); 3.5–4.2 (1H, multiplet); 4.3–5.4 (5H, multiplet); 5.12 (4H, singlet); 5.18 (2H, singlet); 7.43 (6H, multiplet); 8.16 (6H, doublet).

EXAMPLE 18

(3S, 4R)-4-([(S)-1-[N-(p-Nitrobenzyloxycarbonyl)acetimidoyl]pyrrolidin-3-ylthio]carbonylmethyl)-3-[(R)-1-(p-nitrobenzyloxycarbonyloxy)ethyl]-1-[1-(p-nitrobenzyloxycarbonyl)-1-triisopropoxyphosphoranylidenemethyl]-2-azetidinone 756 mg (0.896 mmole) of (3S, 4R)-3-[(R)-1-(p-nitrobenzyloxycarbonyl)-1-triisopropoxyphosphoranylidenemethyl]-4-[(phenylthio)carbonylmethyl]-2-azetidinone obtained as described in Example 14(c), 580 mg (0.180 mmole) of (S)-3-mercapto-1-[N-(p-nitrobenzyloxycarbonyl)acetimidoyl]pyrrolidine and 181 mg (0.179 mmole) of triethylamine were dissolved in 14 ml of methylene chloride. The solution was left to stand in an atmosphere of nitrogen gas at room temperature overnight. The solvent was then distilled off under reduced pressure and the residue was subjected to column chromatography through 20 g of silica gel eluted with 1:1 to 1:10 by volume mixtures of benzene and ethyl acetate, to afford a crude product, which was subjected to chromatography using a Lobar Column B eluted with a 10:30:1 by volume mixture of chloroform, ethyl acetate and methanol, to give 489 mg (yield 51%) of the title product as an oily substance.

Infrared absorption spectrum (KBr) v$_{max}$ cm$^{-1}$: 1750, 1675, 1630.

Nuclear Magnetic Resonance Spectrum (CDCl$_3$) δ ppm: 1.35 (18H, doublet, J=6.5 Hz); 1.43 (3H, doublet, J=6 Hz); 2.24 (3H, singlet); 1.7–2.5 (2H, multiplet); 2.6–3.1 (2H, multiplet); 3.1–4.2 (7H, multiplet); 4.4–5.3 (4H, multiplet); 5.13 (4H, singlet); 5.18 (2H, singlet); 7.45 (2H, doublet); 7.48 (4H, doublet); 8.13 (6H, doublet).

EXAMPLE 19(a)

(3S, 4R)-4-([(R)-1-[N-(p-Nitrobenzyloxycarbonyl) acetimidoyl]pyrrolidin-3-ylthio]carbonylmethyl)-3-[(R)-1-(p-nitrobenzyloxycarbonyloxy)ethyl]-1-[1-(p-nitrobenzyloxycarbonyl)-1-triisopropoxyphosphoranylidenemethyl]-2-azetidinone 325 mg (0.385 mmole) of (3S, 4R)-3-[(R)-1-(p-nitrobenzyloxycarbonyloxy)ethyl]-1-[1-(p-nitrobenzyloxycarbonyl)-1-triisopropoxyphosphoranylidenemethyl]-4-[(phenylthio)carbonylmethyl]-2-azetidinone obtained as described in Example 14(c), 248 mg (0.77 mmole) of (R)-3-mercapto-1-[N-(p-nitrobenzyloxycarbonyl)acetimidoyl]pyrrolidine and 78 mg (0.77 mmole) of triethylamine were dissolved in 6 ml of methylene chloride. The solution was left to stand in an atmosphere of nitrogen gas at room temperature overnight. The solvent was then distilled off and the residue was subjected to chromatography through 10 g of silica gel eluted with a 1:10 by volume mixture of benzene and ethyl acetate to yield a crude product, which was subjected to chromatography using a Lobar column 8 eluted with a 10:30:1 by volume mixture of chloroform, ethyl acetate and methanol, to afford 231 mg (yield 56%) of the title product as an oily substance.

Infrared absorption spectrum (KBr) $\nu_{max}$ cm$^{-1}$: 1750, 1675, 1635.

Nuclear Magnetic Resonance Spectrum (CDc13) δ ppm: 1.35 (18H, doublet, J=6.5 Hz); 1.43 (3H, doublet, J=6 Hz); 2.24 (3H, singlet); 1.7–2.5 (2H, multiplet); 2.6–3.1 (2H, multiplet); 3.1–4.2 (7H, multiplet); 4.4–5.3 (4H, multiplet); 5.13 (4H, singlet); 5.18 (2H, singlet); 7.45 (2H, doublet); 7.48 (4H, doublet); 8.13 (6H, doublet).

EXAMPLE 19(b)

(5R, 6S)-2-[(R)-1-(Acetimidoyl)pyrrolidin-3-ylthio]-6-[(R)-1-hydroxyethyl]carbapen-2-em-3-carboxylic acid Following the procedure described in Example 16(d), (3S, 4R)-4-([(R)-1-(N-(p-nitrobenzyloxycarbonyl)acetimidoyl]pyrrolidin-3-ylthio)carbonylmethyl]-3-[(R)-1-(p-nitrobenzyloxycarbonyloxy)ethyl]-1-[1-(p-nitrobenzyl-oxycarbonyl)-1-triisopropoxyphosphoranylidenemethyl]-2-azetidinone, prepared as described in Example 19(a), was subjected to a cyclization reaction and then the protecting groups were removed from the resulting p-nitrobenzyl (5R, 6S)-2-((R)-1-[N-(p-nitrobenzyloxycarbonyl)acetimidoyl] pyrrolidin-3-ylthio)-6-[-(R)-1-(P-nitrobenzyloxy-carbonyloxy)ethyl]carbapen-2-em-3-carboxylate by the method described in Example 16(e), to afford the title product as white crystals melting at 208°–209° C. (with decomposition).

Infrared absorption spectrum (KBr) $\nu_{max}$ cm$^{-1}$ 3400, 1760, 1675.

Nuclear Magnetic Resonance Spectrum (D$_2$O) δ ppm: 1.29 (3H, doublet, J=6.5 Hz); 1.8–2.7 (2H, multiplet); 2.29 (3H, singlet); 2.9–4.4 (1OH, multiplet).

PREPARATION 1(a)

(3S, 4R)-3-[(R)-1-t-Butyldimethylsilyloxyethyl]-1-(1-methoxy carbonyl-2-methylpropyl-1-enyl)-4-(benzyloxycarbonylmethyl)-2-azetidinone.

1.04 g (2.61 mmole) of (3R,4R)-4-acetoxy-3-[(R)-1-t-butyldimethylsilyloxyethyl]-1-(1-methoxycarbonyl2-methylpropyl-1-enyl)-2-azetidinone and 1.74 g (7.84 mmole) of benzyl trimethylsilylacetate were dissolved in 12 ml of methylene chloride. To the solution were added 50 mg (0.23 mmole) of trimethylsilyl trifluoromethanesulphonate, and the mixture was allowed to stand at room temperature for 7 days. The reaction mixture was then poured into an aqueous solution of sodium bicarbonate, The organic layer was separated, washed with water and dried. The solvent was then distilled off. The resulting residue was purified by liquid chromatography using a Lobar column B (E. Merck & Co. Ltd.), eluted with a 4:1 by volume mixture of hexane and ethyl acetate, to give 109 mg (8.6%) of the starting material and successively 693 mg (yield 55%) of the title product as an oil.

Infrared absorption spectrum (CHCl$_3$) $\nu_{max}$ cm$^{-1}$: 1740 (broad).

Nuclear Magnetic Resonance Spectrum (CDCl$_3$) δ ppm 0.09 (6H, singlet); 0.89 (9H, singlet); 1.23 (3H, doublet, J=6 & 5 Hz); 1.85 (3H, singlet); 2.10 (3H, singlet); 2.67 (2H, doublet, J=7 Hz); 2.85 (1H, doubled doublet, J=6.5 & 2.5 Hz); 3.64 (3H, singlet); 3.9–4.5 (2H, multiplet); 4.90 (1H, doublet, J=12 Hz); 5.06 (1H, doublet, J=12 Hz); 7.28 (5H, singlet).

PREPARATION 1(b)

(3S, 4R)-3-[(R)-1-t-Butyldimethylsilyloxyethyl]-4-(carboxymethyl)-1-(1-methoxycarbonyl-2-methylpropyl-1-enyl)-2-azetidinone 1.18 g of (3S, 4R)-4-(benzyloxycarbonylmethyl)-3-[(R)-1-t-butyldimethylsilyloxyethyl]-1-(1-methoxycarbonyl-2-methylpropyl-1-enyl)-2-azetidinone were dissolved in 26 ml of ethyl acetate. To the solution were added 500 mg of 10% w/w palladium-on-carbon and catalytic reduction was effected under a hydrogen atmosphere. The mixture was stirred for 1.5 hours, after which the catalyst was filtered off and the resulting filtrate was concentrated to dryness by evaporation under reduced pressure to give 960 mg (yield 99%) of the title product as a colourless oil.

Infrared absorption spectrum (CHCl$_3$) $\nu_{max}$ cm$^{-1}$: about 3300, 1734, 1715.

Nuclear magnetic Resonance Spectrum (CDCl$_3$) δ ppm: 0.10 (6H, singlet); 0.90 (9H, singlet); 1.26 (3H, doublet, J=6 Hz); 1.94 (3H, singlet); 2.18 (3H, singlet); 2.71 (2H, doublet, J=7 Hz); 2.94 (1H, doubled doublet, J=6.5 & 2.5 Hz); 3.76 (3H, singlet); 4.0–4.5 (2H, multiplet).

PREPARATION 1(c)

(3S, 4R)-3-[(R)-1-t-Butyldimethylsilyloxyethyl]-1-(1-methoxycarbonyl-2-methylpropyl-1-enyl)-4-([(S)-1-(p-nitrobenzyloxycarbonyl)pyrrolidin-3-ylthio] carbonylmethyl)-2-azetidinone 962 mg (2.41 mmole) of (3S, 4R)-3-[(R)-1-t-butyldimethylsilyloxyethyl]-4-carboxymethyl-1-(1-methoxycarbonyl-2-methylpropyl-1-enyl)-2-azetidinone and 748 mg (2.65 mmole) of (S)-3-mercapto-1-(p-nitrobenzyloxycarbonyl)pyrrolidine were dissolved in 15 ml of benzene. To the solution were added 596 mg (2.89 mmole) of dicyclohexylcarbodiimide and 10 mg (0.082 mmole) of 4-dimethylaminopyrimidine, under ice-cooling with stirring. After 1 hour, insolubles were filtered off and the resulting filtrate was concentrated to dryness by evaporation under reduced pressure. The residue was purified by column chromatography through 30 g of silica gel eluted with a 5:1 by volume mixture of benzene and ethyl acetate, to give 1.41 g (yield 88%) of the title product as an oil.

Nuclear magnetic Resonance Spectrum (CDCl$_3$) δ ppm: 0.09 (6H, singlet); 0.88 (9H, singlet); 1.26 (3H, doublet, J=6 Hz); 1.94 (3H, singlet); 2.17 (3H, singlet); 1.5–2.4 (2H, multiplet); 2.89 (2H, broad doublet, J=7 Hz); 3.52 (2H, triplet, J=7 Hz); 3.76 (3H, singlet); 3.0–4.6 (8H, multiplet); 5.19 (2H, singlet); 7.49 (2H, doublet); 8.21 (2H, doublet).

PREPARATION 1(d)

(3S, 4R)-3-[(R)-1-Hydroxyethyl-1-(1-methoxycarbonyl-2-methylpropyl-1-enyl)-4-([[(S)-1-(p-nitrobenzyloxycarbonyl)pyrrolidin-3-ylthio]carbonylmethyl)-2-azetidinone To a solution of 1.33 g (2.01 mmole) of (3S, 4R)-3-[(R)-1-t-butyldimethylsilyloxyethyl]-1-(1-methoxycarbonyl2-methylpropyl-1-enyl)-4-([[(S)-1-(p-nitrobenzyloxycarbonyl)pyrrolidin-3-ylthio]carbonylmethyl)-2-azetidinone in 24 ml of acetonitrile was added 0.66 g (4.65 mmole) of boron trifluoride etherate, with ice-cooling and stirring. After 5 minutes, the reaction mixture was poured into a mixture of an aqueous solution of sodium bicarbonate and ethyl acetate, with vigorous stirring. The organic layer was separated, washed with water and dried. The solvent was distilled off, to give 1.04 g (yield 96%) of the title product as a colourless oil.

Infrared absorption spectrum (CHCl$_3$) $\nu_{max}$ cm$^{-1}$: 3430, 1750, 1700 (broad).

Nuclear Magnetic Resonance Spectrum (CDCl$_3$) δ ppm: 1.32 (3H, doublet, J=6.5 Hz); 1.95 (3H, singlet); 2.19 (3H, singlet); 1.5–2.5 (2H, multiplet); 2.94 (2H, doublet-like); 3.53 (2H, triplet, J=7 Hz); 3.78 (3H, singlet); 3.0–4.4 (8H, multiplet); 5.21 (2H, singlet); 7.52 (2H, doublet); 8.26 (2H, doublet).

PREPARATION 1(e)

(3S, 4R)-1-(1-Methoxycarbonyl-2-methylpropyl-1-enyl)-3-[(R)-1-(p-nitrobenzyloxycarbonyloxy)ethyl]-4-([[(S)-1-(p-nitrobenzyloxycarbonyl)pyrrolidin-3-ylthio]carbonylmethyl)-2-azetidinone 110 mg (0.20 mmole) of (3S, 4R)-3-[(R)-1-hydroxyethyl]-1-(1-methoxycarbonyl-2-methylpropyl-1-enyl)-4-([[(S)-1-(p-nitrobenzyloxycarbonyl)pyrrolidin-3-ylthio]carbonyl-methyl)-2-azetidinone and 97.6 mg (0.80 mmole) of 4-dimethylaminopyridine were dissolved in 4 ml of methylene chloride. To the solution was added dropwise 1 ml of a methylene chloride solution containing 170 mg (0.80 mmole) of p-nitrobenzyloxycarbonyl chloride, with ice-cooling and stirring. After completion of the addition, the reaction mixture was allowed to stand for 3 hours at room temperature.

At the end of this time, the reaction mixture was poured into ice-water. The organic layer was separated, washed successively with 0.2 N hydrochloric acid, water and a saturated solution of sodium chloride and dried. The solvent was distilled off and the resulting residue was purified by column chromatography through 4 g of silica gel eluted with 12.5 to 60% by volume solutions of ethyl acetate in benzene, to give120 mg (yield 82%) of the title product as an oil.

Infrared absorption spectrum (CHCl$_3$) $\nu_{max}$ cm$^{-1}$: 1745, 1690 (broad).

Nuclear Magnetic Resonance Spectrum (CDCl$_3$) δ ppm: 1.45 (3H, doublet, J=6.5Hz); 1.94 (3H, singlet); 2.18 (3H, singlet); 1.5–2.6 (2H, multiplet); 2.88 (2H, doublet, J=7 Hz); 3.12 (1H, doubled doublet, J=7.5 & 2.5 Hz); 3.47 (2H, triplet-like); 3.75 (3H, singlet); 3.0–4.5 (7H, multiplet); 5.18 (2H, singlet); 5.22 (2H, singlet); 7.46 (2H, doublet); 7.49 (2H, doublet); 8.18 (4H, doublet).

PREPARATION 2(a)

(3S, 4R)-3-[(R)-1-t-Butyldimethylsilyloxyethyl]-4-[(phenylthio)carbonylmethyl]-2-azetidinone To a solution of 3.28 g of (3S, 4R)-3-[(R)-1-t-butyldimethylsilyloxyethyl]-4-[(phenylthio)ethynyl]-2-azetidinone in 75.0 ml of anhydrous methylene chloride were added, under an atmosphere of nitrogen gas, 3.5 ml of trifluoroacetic acid, with stirring and ice-cooling. The mixture was then stirred for 30 minutes under ice-cooling and for a further 1.5 hours at room temperature. The reaction mixture was then poured into a mixture of 1.14 g of sodium bicarbonate, 75 ml of water and 300 ml of ethyl acetate. The mixture was saturated with sodium chloride and the organic layer was separated. The aqueous layer was extracted twice with ethyl acetate. The organic layer and the ethyl acetate extracts were combined, and the combined solution was washed successively with an aqueous solution of sodium bicarbonate and a saturated aqueous solution of sodium chloride and then dried over anhydrous sodium sulphate. The solvent was distilled off under reduced pressure and the residue was subjected to column chromatography through silica gel, eluted with a 3:1 by volume mixture of cyclohexane and ethyl acetate, to give 3.09 g (yield 89.9%) of the title thioester compound, melting at 94°–95° C.

Infrared and NMR spectra thereof were identical with those obtained in Example 3(a).

PREPARATION 2(b)

(3S, 4R)-3-[(R)-1-t-Butyldimethylsilyloxyethyl]-4-([(S)-1-(p-nitrobenzyloxycarbonyl)pyrrolidin-3-yl-thio]carbonylmethyl)-2-azetidinone 191 mg (0.50 mmole) of the azetidinone compound obtained as described in Preparation 2(a) were dissolved in 5 ml of dry methylene chloride. To the solution were added, in turn, 159 mg (0.56 mmole) of (S)-3-mercapto-1-(p-nitrobenzyloxycarbonyl)pyrrolidine and a catalytic amount of triethylamine. The mixture was refluxed for 3 hours and then left to stand overnight. After completion of the reaction, the solvent was distilled off and the residue was dissolved in 40 ml of ethyl acetate, washed successively with water (10 ml twice) and saturated aqueous solution of sodium chloride and dried over anhydrous magnesium sulphate The magnesium sulphate was filtered off and the ethyl acetate was distilled off under reduced pressure. The resulting oily substance was subjected to Lobar column chromatography, eluted with ethyl acetate, to afford 253 mg (yield 91.2%) of the title azetidinone compound, melting at 104°–106° C.

infrared and NMR spectra thereof were identical with those obtained in Example 13(b).

PREPARATION 2(c)

(3S, 4R)-3-[(R)-1-t-Butyldimethylsilyloxyethyl]-4-([(S)-1-[N-(p-nitrobenzyloxycarbonyl)acetimidoyl]pyrrolidin-3-ylthio]carbonylmethyl)-2-azetidinone 382 mg (1.01 mmole) of the azetidinone compound obtained as described in Preparation 2(a) were dissolved in 10 ml of dry methylene chloride. To the solution were added, in turn, 357 mg (1.10 mmole) of (S)-3-mercapto-1-[N-(p-nitrobenzyloxycarbonyl)acetimidoyl]pyrrolidine and a catalytic amount of triethylamine, with stirring at room temperature. The mixture was left to stand at that temperature for 2 hours and then refluxed for 3 hours. After completion of the reaction, the solvent was distilled off and the residue was dissolved in 40 ml of ethyl acetate, washed successively with water (10 ml twice) and a saturated aqueous solution of sodium chloride and dried over anhydrous magnesium sulphate. The magnesium sulphate was filtered off and the ethyl acetate was distilled from the filtrate under reduced pressure. The oily substance obtained was subjected to Lobar column chromatography, eluted with ethyl acetate, to afford 514 mg (yield 86.1%) of the title azetidinone compound.

Infrared absorption spectrum (KBr) $v_{max}$ cm$^{-1}$: 1600, 1640, 1690, 1760, 3050–3500.

Nuclear Magnetic Resonance Spectrum (CDCl$_3$) δ ppm: 0.09 (6H, singlet); 0.88 (9H, singlet); 1.20 (3H, doublet, J=6.5 Hz); 2.29 (3H, singlet), 1.5–2.5 (2H, multiplet; 2.7–3.03 (2H, multiplet); 3.3–4.4 (8H, multiplet); 5.18 (2H, singlet); 6.27 (1H, broad singlet); 7.52 (2H, doublet); 8.17 (2H, doublet).

PREPARATION 3

(3S, 4R)-3-[(R)-1-Hydroxyethyl]-4-[(phenylthio) carbonylmethyl]-2-azetidinone

To a solution of 718 mg of (3S, 4S)-3-[(R)-1-hydroxyethyl]-4-[(phenylthio)ethynyl]-2-azetidinone in 8 ml of anhydrous methylene chloride was added, under an atmosphere of nitrogen gas, 1.1 ml of trifluoroacetic acid, with stirring and ice-cooling. The mixture was then stirred for 30 minutes under ice-cooling and for a further 1.5 hours at room temperature. The reaction mixture was then poured into a mixture of 2.44 g of sodium bicarbonate, 15 ml of water and 30 ml of ethyl acetate. The mixture was saturated with sodium chloride and the organic layer was separated. The aqueous layer was extracted twice with ethyl acetate. The organic layer and the ethyl acetate extracts were combined, and the combined solution was washed successively with an aqueous solution of sodium bicarbonate and a saturated aqueous solution of sodium chloride and dried over anhydrous sodium sulphate. The solvent was distilled off under reduced pressure and the residue was subjected to column chromatography through silica gel, eluted with a 1:3 by volume mixture of cyclohexane and ethyl acetate, to give 281 mg (yield 36.5%) of the title thioester compound, which was recrystallized from a mixture of ethyl acetate and hexane to give crystals melting at 121.5–123.5° C.

Infrared absorption spectrum (KBr) $v_{max}$ cm$^{-1}$: 1730.

Nuclear Magnetic Resonance Spectrum (deuteroacetone) δ ppm: 1.23 (3H, doublet, J=6 Hz); 2.77 (1H, singlet); 2.8–3.3 (3H, multiplet); 3.8–4.2 (2H, multiplet); 7.25 (1H, broad singlet); 7.50 (5H, singlet);

PREPARATION 4(a)

(3S, 4R)-3-[(R)-1-t-Butyldimethylsilyloxyethyl]-1-[1-(p-nitrobenzyloxycarbonyl)-2-methylpropyl-1-enyl]-4-[(phenylthio)carbonylmethyl]-2-azetidinone To a solution of 86 mg of (3S, 4R)-3-[(R)-1-t-butyldimethylsilyloxyethyl]-1-[(R)-2-methyl-1-(p-nitrobenzyloxycarbonyl)prop-2-enyl]-4-[(phenylthio) carbonylmethyl]-2-azetidinone in 1.5 ml of methylene chloride were added 15 mg of triethylamine. The mixture was left to stand at room temperature for 1 hour, after which the solvent was distilled off and the residue was dissolved in a 20:1 by volume mixture of benzene and ethyl acetate and subjected to column chromatography through 1 g of silica gel, to afford 84 mg (yield 98%) of the title product as an oil.

Infrared absorption spectrum (CHCl$_3$) $v_{max}$ cm$^{-1}$: cm$^{1}$ 1750, 1715 (shoulder), 1625.

Specific rotation [α]$^{25}$ +46° (C=1.32, chloroform).

Nuclear Magnetic Resonance Spectrum (CDCl$_3$) δ ppm: 0.00 (3H, singlet); 0.05 (3H, singlet); 0.86 (9H, singlet); 1.25 (3H, doublet, J=6 Hz); 2.00 (3H, singlet); 2.20 (3H, singlet); 2.90 (1H, doubled doublet, J=6 & 2.5 Hz); 2.95 (2H, doublet, J=6.5 Hz); 4.15 (1H, multiplet); 4.40 (1H, tripled doublet, J=6.5 & 2.5 Hz); 5.26 (2H, singlet); 7.33 (5H, broad singlet); 7.52 (2H, doublet); 8.17 (2H, doublet).

PREPARATION 4(b)

(3S, 4R)-3-[(R)-1-t-8butyldimethylsilyloxyethyl]-4-([2-(p-nitrobenzyloxycarbonylamino)ethylthio] carbonylmethyl)-1-[2-methyl-1-(p-nitrobenzyloxycarbonyl)prop-1-enyl]-2-azetidinone 166 mg (0.249 mmole) of (3S, 4R)-3-[(R)-1-t-butyldimethylsilyloxyethyl]-1-[2-methyl-1-(p-nitrobenzyloxycarbonyl)prop-1-enyl]-4-[(phenylthio) carbonylmethyl]-2-azetidinone obtained as described in Preparation 4(a), 139 mg (0.54 mmole) of 2-(R-nitrobenzyloxycarbonyl-amino)ethanethiol]and 55 mg (0.54 mmole) of triethylamine were dissolved in 38 ml of methylene chloride. The solution was left to stand in an atmosphere of nitrogen gas at room temperature overnight. The solvent was distilled off under reduced pressure and the residue was subjected to chromatography using a Lobar column B eluted with a 1:2 by volume mixture of hexane and ethyl acetate, to afford 156 mg (yield 76%) of the title product as an oily substance.

Infrared absorption spectrum (CHCl$_3$) $v_{max}$ cm$^{-1}$: 3460, 1748, 1720, 1685.

Nuclear Magnetic Resonance Spectrum (CDCl$_3$) δ ppm: 0.00 (3H, singlet); 0.04 (3H, singlet); 0.84 (9H, singlet); 1.21 (3H, doublet, J=6 Hz); 1.95 (3H, singlet); 2.15 (3H, singlet); 2.87 (2H, doublet, J=6.5 Hz); 2.8–3.5 (5H, multiplet); 4.13 (1H, multiplet); 4.35 (1H, tripled doublet, J=6,5 & 2.5 Hz); 5.14 (2H, singlet); 5.24 (2H, singlet); 5.37 (1H, broad singlet); 7.43 (2H, doublet); 7.51 (2H, doublet); 8.13 (2H, doublet); 8.17 (2H, doublet).

PREPARATION 4(c)

(3S, 4R)-3-[(R)-1-t-Butyldimethylsilyloxyethyl]-4-([(S)-1-[N-(p-nitrobenzyloxycarbonyl) acetimidoyllpyrrolidin-3-ylthio]carbonylmethyl)-1-[2-methyl-1-(p-nitrobenzyloxycarbonyl)prop-1-enyl]-2-azetidinone 491 mg (0.802 mmole) of (3S, 4R)-3-[(R)-1-t-butyldimethylsilyloxyethyl]-1-[2-methyl-1-(p-nitrobenzyloxycarbonyl)prop-1-enyl]-4-[(phenylthio) carbonylmethyl]-2-azetidinone obtained as described in Preparation 4 (a), 518 mg (1.60 mmole) of (S)-3-mercapto-1-[N-(p-nitrobenzyloxycarbonyl)acetimidoyl]pyrrolidine and 162 mg (1.60 mmole) of triethylamine were dissolved in 10 ml of methylene chloride. The solution was left to stand in an atmosphere of nitrogen gas at room temperature for 1.5 hours, after which the solvent was distilled off under reduced pressure and the residue was subjected to chromatography using a Lobar column B eluted with a 2:3 by volume mixture of benzene and ethyl acetate, to afford 511 mg (yield 77%) of the title product as an oily substance.

Infrared absorption spectrum(CHCl$_3$) $v_{max}$ cm$^{-1}$: 1747, 1720, 1676.

Nuclear Magnetic Resonance Spectrum CDCl$_3$) δ ppm: 0.00 (3H, singlet); 0.04 (3H, singlet); 0.85 (9H, singlet);

1.20 (3H, doublet, J=6 Hz); 1.94 (3H, singlet); 2.16 (3H, singlet); 2.26 (3H, singlet); 1.7–2.5 (2H, multiplet); 2.82 (2H, broad doublet, J=7 Hz); 3.1–4.5 (8H, multiplet); 5.14 (2H, singlet); 5.22 (2H, singlet); 7.46 (2H, doublet); 7.49 (2H, doublet); 8.10 (2H, doublet); 8.14 (2H, doublet).

PREPARATION 5

(3S, 4R)-4-([2-(p-Nitrobenzyloxycarbonylamino)ethylthio]carbonylmethyl)-1-F2-methyl-1-(p-nitrobenzyloxycarbonyl)prop-1-enyl]-3-[(R)-1-(p-nitrobenzyloxycarbonyloxy)ethyl]-2-azetidinone 21 mg (0.032 mmole) of (3S, 4R)-1-[2-methyl-1-(p-nitrobenzyloxycarbonyl)prop-1-enyl]-3-[(R)-1-(R-nitrobenzyloxycarbonyloxy)ethyl]-4-[(phenylthio)carbonylmethyl]-2-azetidinone obtained as described in Example 14(b)(iii), 16 mg (0.063 mmole) of 2-(p-nitrobenzyloxycarbonylamino)ethanethiol and 6 mg (0.06 mmole) of triethylamine were dissolved in 0.4 ml of methylene chloride. The solution was left to stand in an atmosphere of nitrogen gas at room temperature for 3 hours. The reaction mixture was then-diluted with chloroform, washed with water and dried. The solvent was distilled off and the residue was subjected to thin layer chromatography using silica gel, developed with a 2:3 by volume mixture of hexane and ethyl acetate, to afford 17 mg (yield 60%) of the title product as an oily substance.

Infrared absorption spectrum (CHCl$_3$) $v_{max}$ cm$^{-1}$: 3460, 1753, 1721, 1700 (shoulder), 1682.

Specific rotation [α]$^{25}$ +8.5° (C=0.86, chloroform).

Nuclear Magnetic Resonance Spectrum(CDCl) δ ppm: 1.42 (3H, doublet, J=6.5 Hz); 1.97 (3H, singlet); 2.23 (3H, singlet); 2.84 (2H, doublet, J=6.5 Hz); 2.7–3.7 (5H, multiplet); 4.27 (1H, tripled doublet, J=6.5 & 2 Hz); 4.8–5.5 (2H, multiplet); 5.16 (2H, singlet); 5.19 (2H, singlet); 5.23 (2H, singlet); 7.46 (4H, broad doublet); 7.51 (2H, doublet); 8.18 (6H, doublet).

PREPARATION 6 (a)

(3S, 4R)-3-[(R)-1-(Allyloxycarbonyloxy)ethyl]-1-(p-methoxybenzyl)-4-[(phenylthio)carbonylmethyl]-2-azetidinone To a solution of 377 mg of (3S, 4R)-4-acetoxy-3-[(R)-1-(allyloxycarbonyloxy)ethyl]-1-(p-methoxybenzyl)-2-azetidinone in 2 ml of dry methylene chloride were added 448 mg (2 mmole) of 1-phenylthio-1-(trimethylsilyloxy)ethylene and then the mixture was stirred at room temperature, A catalytic amount of trimethylsilyltrifluoromethanesulphonate was added to the mixture, which was then left to stand at room temperature overnight. The precipitate produced was dissolved in 200 ml of ethyl acetate, and the resulting solution was washed successively with 100 ml of water and 100 ml of a saturated aqueous solution of sodium chloride. It was then dried over anhydrous magnesium sulphate and subjected to Lobar column chromatography eluted with a 1:1 by volume mixture of cyclohexane and ethyl acetate, to afford 430 mg (yield 91%) of the title azetidinone.

Nuclear Magnetic Resonance Spectrum (CDCl$_3$) δ ppm: 1.39 (3H, doublet, J=6,5 Hz); 2.8 (2H, doubled doublet, J=3.0 & 9 Hz); 3.1 (1H, doubled doublet, J=2.5 & 6.5 Hz); 3.75 (3H, singlet); 3.8–4.62 (6H, multiplet); 4.8–5.4 (2H, multiplet); 5.6–7.1 (1H, multiplet); 6.7–7.5 (9H, multiplet).

Mass spectrum m/e: 469 (M$^+$).

PREPARATION 6 (b)

(3S, 4R)-3-[(R)-1-(Allyloxycarbonyloxy)ethyl]-4-[(phenylthio)carbonylmethyl]-2-azetidinone 140 mg (0.3 mmole) of the azetidinone compound obtained as described in Preparation 6(a) were dissolved in a mixture of 2 ml of acetone and 1 ml of water. To the solution were added 822 mg (1.5 mmole) of ceric ammonium nitrate, with stirring at room temperature, followed by stirring for 2 hours. 100 ml of ethyl acetate were added to the reaction mixture. The mixture was then washed successively with water (20 ml twice), 20 ml of a 5% w/v aqueous solution of sodium bicarbonate and 20 ml of a saturated aqueous solution of sodium chloride and dried over anhydrous magnesium sulphate. The ethyl acetate was distilled off and the residue was subjected to Lobar column chromatography eluted with a 1:1 by volume mixture of cyclohexane and ethyl acetate, to give 25 mg (yield 24.0%) of the title azetidinone compound.

Nuclear Magnetic Resonance Spectrum (CDCl$_3$) δ ppm; 1.4 (3H, doublet, J=6.5 Hz); 2.8–3.3 (3H, multiplet); 3.8–4.2 (2H, multiplet); 4.4–4.7 (2H, multiplet); 4.8–5.5 (2H, multiplet); 5.6–6.1 (1H, multiplet); 6.1–6.3 (1H, broad singlet); 7.36 (5H, singlet). Mass spectrum m/e: 349 (M$^+$). Elemental Analysis Calculated: C, 58.4%; H, 5.48%; N, 4.01%; S, 9.15%. Found: C, 58.1%; H, 5.49%; N, 3.89%; S, 9.34%.

PREPARATION 7(a)

(-3S, 4R)-1-(p-Methoxybenzyl)-3-[(R)-1-(p-nitrobenzyloxycarbonyloxy)ethyl]-4-[(phenylthio)carbonylmethyl]2-azetidinone 1.18 g (2.5 mmole) of (3S,4R)-1-(p-methoxybenzyl)-3-[(R)-1-(p-nitrobenzyloxycarbonyl)ethyl]-4-acetoxy-2-azetidinone were dissolved in 10 ml of dry methylene chloride, after which the mixture was stirred at room temperature. To the resulting solution were added 2.24 g (10 mmole) of 1-phenylthio-1-trimethylsilyl)oxyethylene and 0.11 g (0.50 mmole) of trimethylsilyl trifluoromethanesulphonate (as a catalyst). The mixture was left to stand at room temperature overnight. The methylene chloride was then distilled off and the residue was dissolved in 100 ml of ethyl acetate. The resulting solution was washed successively with 50 ml of water, with 50 ml of a 5% w/v aqueous solution of sodium bicarbonate and with 50 ml of a saturated aqueous solution of sodium chloride, after which it was dried over anhydrous magnesium sulphate. The magnesium sulphate was filtered off and the ethyl acetate was distilled from the filtrate under reduced pressure. The residue was subjected to column chromatography through 125 g of silica gel, eluted with a 1:1 by volume mixture of cyclohexane and ethyl acetate, to give 1.34 g (yield 94.9%) of the desired (R)-4-[(phenylthio)carbonylmethyl]-2-azetidinone derivative, as an oily substance.

Elemental Analysis Calculated: C, 61.60%; H, 5.00%; N, 4.96%; S, 5.67%. Found: C, 61.33%; H, 5.12%; N, 4.81%; S, 5.63%.

PREPARATION 7(b)

(3S, 4R)-1-(p-Methoxybenzyl)-4-([(S)-1-[N-(p-nitrobenzyloxycarbonyl)acetimidoyl]pyrrolidin-3-ylthio]-carbonylmethyl?-3-E (R)-1-(p-nitrobenzyloxycarbonyloxy)ethyl-2-azetidinone In 5 ml of dry methylene chloride was dissolved 219 mg (0.39 mmole) of the azetidinone compound obtained as described in Preparation 7(a).

To the solution were added, in turn, 250 mg (0.77 mmole) of (S)-3-mercapto-1-[N-(p-nitrobenzyloxycarbonyl)acetimidoyl]pyrrolidine and a catalytic amount of triethylamine, with stirring at room temperature The mixture was left to stand at that temperature overnight. After completion of the reaction, the solvent was distilled off and the residue was subjected to chromatography using a Lobar column eluted with ethyl acetate, to afford 276 mg (yield 91.5%) of the title azetidinone.

Nuclear Magnetic Resonance Spectrum (CDCl$_3$) δ ppm: 1.39 (3H, doublet, J=6.5 Hz); 1.7–2.5 (2H, multiplet); 2.25 (3H, singlet); 2.6–2.8 (2H, multiplet); 3.1 (1H, broad doublet, J=8 Hz); 3.2–4.0 (6H, multiplet); 3.73 (3H, singlet); 4.10 (1H, doublet, J=15 Hz); 4.50 (1H, doublet, J=15 Hz); 4.9–5.3 (1H, multiplet); 5.19 (2H, singlet); 6.75 (2H, doublet); 7.10 (2H, doublet); 7.50 (4H, doublet); 8.15 (2H, doublet); 8.20 (2H, doublet).

PREPARATION 8

((3S, 4R)-3-[(R)-1-(Allyloxycarbonyloxy)ethyl]-1-(p-methoxybenzyl)-4-([(S)-1-]N-(p-nitrobenzyloxycarbonyl)acetimidoyl]pyrrolidin-3-ylthio carbonylmethyl)-2-azetidinone To a solution of 461 mg (0.98 mmole) of the azetidinone compound obtained as described in Preparation 6(a) in 5 ml of dry methylene chloride were added 969 mg (3 mmole) of (S)-3-mercapto-1-[N-(p-nitrobenzyloxycarbonyl) acetimidoyl]pyrrolidine. A catalytic amount of triethylamine was added and the mixture was left to stand at room temperature overnight. After completion of the reaction, the solvent was distilled off and the residue was subjected to chromatography using a Lobar column eluted with ethyl acetate, to afford 546 mg (yield 76.7%) of the title azetidinone compound.

Nuclear Magnetic Resonance Spectrum (CDCl$_3$) δ ppm: 1.38 (3H, doublet, J=6 Hz); 2.27 (3H, singlet); 1.7–2.6 (2H, multiplet); 2.6–2.9 (2H, multiplet); 3.1 (Broad doublet, J=7 Hz); 3.2–4.5 (9H, multiplet); 4.5–4.7 (2H, multiplet); 4.85–5.20 (2H, multiplet); 4.80–5.50 (2H, multiplet); 5.6–6.2 (1H, multiplet); 6.82 (2H, doublet); 7.52 (2H, doublet); 8.15 (2H, doublet).

PREPARATION 9

(3S, 4R)-3-[(R)-1-(Allyloxycarbonyloxy)ethyl]-4-([(S)-1-[N-(p-nitrobenzyloxycarbonyl)acetimidoyl] pyrrolidin-3-ylthio]carbonylmethyl)-2-azetidinone To a solution of 115 mg (0.26 mmole) of the azetidinone compound obtained as described in Preparation 6(b) and 125 mg (0.386 mmole) of (S)-3-mercapto-1-[N-(p-nitrobenzyloxycarbonyl)acetimidoyl]pyrrolidine in 5 ml of dry methylene chloride was added a catalytic amount of triethylamine. The mixture was left to stand at room temperature overnight. The solvent was distilled off and the residue was subjected to chromatography using a Lobar column eluted with ethyl acetate to afford 168 mg (yield 98%) of the title azetidinone compound.

Nuclear Magnetic Resonance Spectrum (CDCl$_3$) δ ppm: 1.38 (3H, doublet, J=6 Hz); 2.26 (3H, singlet); 1.8–2.6 (2H, multiplet); 2.7–3.0 (2H, multiplet); 3.0 (Broad doublet, J=6.5 Hz); 3.2–4.2 (5H, multiplet); 4.5–4.7 (2H, multiplet); 4.9–5.1 (1H, multiplet); 5.1–5.4 (2H, multiplet); 5.6–6.1 (1H, multiplet); 6.17 (1H, broad singlet); 7.48 (2H, doublet); 8.15 (2H, doublet).

What is claimed is:
1. A process for preparing a compound of the formula (IV):

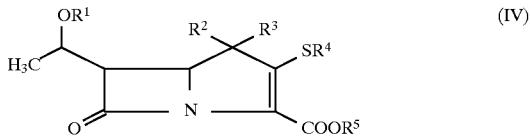

which comprises cyclising a compound of the formula (I):

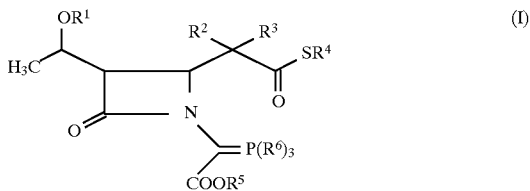

wherein:

$R^1$ represents hydrogen or a hydroxy-protecting group;

$R^2$ and $R^3$ may be the same or different and each represents hydrogen, a $C_1$–$C_6$ alkyl group or a phenyl group;

$R^4$ represents a $C_1$–$C_6$ alkyl group;

a non-aromatic heterocyclic group having from 4 to 8 ring carbon atoms and having one or two ring nitrogen atoms and optionally containing an oxygen atom, a sulphur atom, a sulphinyl group, a sulphonyl group or a carbonyl group, and optionally having one or more substituents attached to the carbon atoms or to any nitrogen atom, selected from the group consisting of (1) substituents for attachment to the ring carbon atoms selected from the group consisting of $C_1$–$C_6$ alkyl groups, cyclopropyl, cyclobutyl, cyclopentyl, cyclohexyl groups, $C_2$–$C_8$ alkoxyalkyl groups, methoxycarbonylmethyl, ethoxycarbonylmethyl, t-butoxycarbonylmethyl, benzyloxycarbonylethyl, methoxycarbonylpropyl groups, $C_2$–$C_7$ cyanoalkyl groups, $C_1$–$C_6$ haloalkyl groups, $C_1$–$C_6$ alkoxy groups, halogen atoms, $C_1$–$C_6$ aliphatic acyloxy groups, $C_1$–$C_6$ aliphatic acylamino groups, cyano group, azido group, carboxy group, $C_2$–$C_7$ alkoxycarbonyl groups, carbamoyl group, $C_1$–$C_6$ alkylthio groups, $C_1$–$C_6$ alkylsulphinyl groups, $C_1$–$C_6$ alkylsulphonyl groups, nitro group; and (2) substituents for attachment to said ring nitrogen atom(s) selected from the group consisting of $C_1$–$C_6$ alkyl groups, $C_2$–$C_6$ alkenyl groups, $C_2$–$C_6$ alkynyl groups, $C_3$–$C_8$ cycloalkyl groups, cyclopropylmethyl, cyclobutylethyl, cyclopentylmethyl, cyclohexylmethyl, cycloheptylmethyl, 2-cyclopentylmethyl, 2-cyclohexylmethyl, 3-cyclopentylpropyl, 2-cyclopentylpropyl, 3-cyclohexylmethyl, 2-cyclohexylpropyl, 4-cyclopentylbutyl, 3-cyclohexylbutyl, phenyl, naphthyl groups, benzyl, phenethyl, 3-phenylpropyl, $C_1$–$C_6$ aliphatic acyl groups, cyclopropanecarbonyl, cyclobutanecarbonyl, cyclopentanecarbonyl, cyclohexanecarbonyl, cyclopropylacetyl, cyclobutylacetyl, cyclopentylacetyl, cyclohexylacetyl, 3-cyclopentylpropionyl, 3-cyclohexylpropionyl, 4-cyclopentylbutyryl, 4-cyclohexylbutyryl, benzoyl, 1-naphthoyl, 2-naphthoyl groups, phenylacetyl, 1-naphthylacetyl, 3-phenylpropionyl, hydratropoyl, cinnamoyl, phenylpropioloyl, furoyl, thenoyl, nicotinoyl, isonicotinoyl, 4-thiazolecarbonyl, 5-pyrimidinecarbonyl, 2-pyrazinecarbonyl, 2-thienylacetyl, 3-(2-thienyl)propionyl, 4-thiazolylacetyl, 2-pyridylacetyl, 4-pyridylacetyl, 5-pyrimidinylacetyl, 1-aziridinylacetyl, 1-azetidinylacetyl, 3-azetidinylacetyl, 1-pyrrolidinylacetyl, 2-pyrrolidinylacetyl, 3-pyrrolidinylacetyl, 3-(2-pyrrolidinyl)propionyl, piperidinoacetyl, 2-piperidinylacetyl, 4-piperidinylacetyl, morpholinoacetyl, 1-aziridinecarbonyl, 1-azetidinecarbonyl, 3-azetidinecarbonyl, 1-pyrrolidinecarbonyl, 2-pyrrolidinecarbonyl, 3-pyrrolidinecarbonyl, 1-piperidinecarbonyl, 2-piperidinecarbonyl, 4-piperidinecarbonyl, 4-morpholinecarbonyl, phenacyl group, sulpho group, $C_1$–$C_6$ alkylsulphonyl groups, $C_1$–$C_6$ alkylsulphonyl groups, $C_2$–$C_6$ alkylsulphonyl groups, $C_2$–$C_6$ alkylsulphonyl groups, cyclopropylsulphonyl, cyclobutylsulphonyl, cycclopentylsulphonyl, cyclohexylsulphonyl, cyclopropylmethylsulphonyl, cyclobutylmethylsulphonyl, cyclopentylmethylsulphonyl, cyclohexylmethylsulphonyl, 2-cyclopentylethylsulphonyl, 2-cyclohexylethylsulphoyl, 3-cyclopentylpropylsulphonyl, 2-cyclopentylpropylsulphonyl, phenylsulphonyl, 1-naphthylsulphonyl, 2-naphthylsulphonyl, benzylsulphonyl, phenethylsulphonyl, 3-phenylpropylsulphonyl, 2-phenylpropylsulphonyl, 2-thienylsulphonyl, 4-thiazolylsulphonyl, 2-pyridylsulphonyl, 4-pyridylsulphonyl, 2-thienylmethylsulphonyl, 3-(2-thienyl)propylsulphonyl, 4-thiazolylmethylsulphonyl, 2-pyridylmethylsulphonyl, 4-pyridylmethylsulphonyl group, groups of the formula

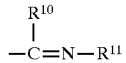

wherein $R^{10}$ represents a hydrogen atom or a $C_1$–$C_4$ alkyl group and $R^{11}$ represents a hydrogen atom, allyloxycarbonyl, 2-methylallyloxycarbonyl, 2-chloroallyloxycarbonyl, 2,2,2-trichloroethoxycarbonyl, 2,2,2-tribromoethoxycarbonyl, p-nitrobenzyloxycarbonyl or o-nitrobenzyloxycarbonyl, groups of the formula

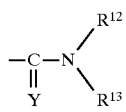

wherein $R^{12}$ and $R^{13}$ are the same or different and each represents a hydrogen atom or a $C_1$–$C_4$ alkyl group and Y represents an oxygen atom, a sulphur atom or an imino group which may be optionally substituted with a $C_1$–$C_4$ alkyl group, $C_2$–$C_7$ alkoxycarbonyl groups, benzyloxycarbonyl, phenethyloxycarbonyl, p-nitrobenzyloxycarbonyl and o nitrobenzyloxy carbonyl group; and the substituents attached to the nitrogen atoms of the non-aromatic heterocyclic groups may be substituted with one or more groups selected from the group consisting of $C_1$–$C_4$ alkyl groups, $C_1$–$C_4$ alkoxy groups, hydroxy, amino, halogen, $C_1$–$C_5$ aliphatic acyloxy groups, $C_1$–$C_5$ aliphatic acylamino groups, cyano, azido, carboxy, $C_2$–$C_5$ alkoxycarbonyl groups, the carbamoyl group, $C_1$–$C_4$ alkylthio group, $C_1$–$C_4$ alkylsulphonyl groups, $C_1$–$C_4$ alkylsulphonyl groups, nitro group, and groups of formula

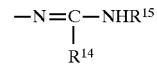

wherein $R^{14}$ and $R^{15}$ the same or different and each represents a hydrogen atom or a $C_1$–$C_4$ alkyl group;

a substituted alkyl group, said substituted alkyl groups being selected from the group consisting of a hydroxyalkyl group, a protected hydroxy alkyl group, an aminoalkyl group, and a protected aminoalkyl group;

a group represented by the formula

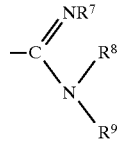

wherein $R^7$, $R^8$, and $R^9$ are the same or different and each represents hydrogen, methyl, ethyl, an amino-protecting group, or $R^7$ and $R^8$ or $R^8$ and $R^9$, together with the atom or atoms to which they are attached, form a ring and when $R^8$ and $R^9$ form a ring, they together represent ethylene, trimethylene, tetramethylene, pentamethylene or hexamethylene, and when $R^7$ and $R^8$ form a ring, $R^7$ and $R^8$ together represent ethylene or trimethylene;

an aryl-substituted alkyl group, selected from the group consisting of benzyl, p-methoxybenzyl, m-nitrobenzyl, o-methylbenzyl, p-bromobenzyl and p-aminobenzyl; furfuryl;

an alkyl group having a non-aromatic heterocyclic substituent the alkyl group of which is a $C_1$–$C_4$ alkyl, and the non-aromatic heterocyclic substituent is selected from the substituted or unsubstituted non aromatic heterocyclic groups within the definition hereinbefore of $R^4$;

an alkenyl group or a substituted alkenyl group, selected from the group consisting of vinyl, allyl, 1-propenyl and 2-butenyl;

an alkynyl group or a substituted alkynyl group selected from the group consisting of ethynyl, 2-propynyl and 1-propynyl;

and when $R^4$ represents a substituted alkenyl or alkynyl group as defined above, the substituents are selected from the group consisting of the formula —$NR^{16}R^{17}$ wherein $R^{16}$ and $R^{17}$ are the same or different and each represents hydrogen, methyl, ethyl, propyl, isopropyl group, formyl, acetyl, propionyl, isobutyryl, chloroacetyl, trifluoroacetyl, benzoyl group or an amino-protecting group; groups of the formula —$CONHR^{18}$, wherein $R^{18}$ represents a hydrogen, methyl, ethyl, propyl, or an amino-protecting group; groups of the formula —$NHCONHR^{18}$; groups of the formula —$COOR^{19}$ wherein $R^{19}$ represents hydrogen, methyl, ethyl, propyl or a carboxy-protecting group; groups of the formula —$SR^{20}$, wherein $R^{20}$ represents hydrogen, methyl, ethyl, propyl, allyl, vinyl, 1-methylnonyl, 1-propenyl, ethynyl, 2-propynyl, 1-propynyl, cyclopropyl, cyclopentyl, cyclohexyl, cyclopropylmethyl, cyclopentylmethyl, 2-cyclohexylethyl, 2-cyclopentylethyl, benzyl, phenylethyl, p-methoxybenzyl, p-bromobenzyl, phenyl, p-tolyl, p-methoxyphenyl, thienyl, furyl, imidazolyl, pyridyl, thienylmethyl, 2-thienylmethyl, pyridylmethyl, imidazolylmethyl and thiazolylmethyl; groups of the formula —S(:O)R$^{20}$; groups of the formula —SO$_2$R$^{21}$ wherein R$^{21}$ represents any of the groups defined for R$^{20}$ or methoxy, ethoxy or propoxy; groups of formula —OSO$_2$R$^{20}$; cyano; nitro; and azido groups;

R$^5$ represents hydrogen, or a carboxy-protecting group;

R$^6$ represents an alkoxy group having from 1 to 6 carbon atoms, or a phenoxy group selected from the group consisting of phenoxy, p-methylphenoxy, p-methoxyphenoxy groups, and a dialkylamino group wherein each alkyl group has from 1 to 6 carbon atoms, or two R$^6$ groups together represent an o-phenylenedioxy group, and the other R$^6$ represents any other R$^6$ group, or the three R$^6$ groups together represent a group of the formula CH$_3$—(CH$_2$—O—)$_3$.

2. A process for preparing a compound of the formula (IV):

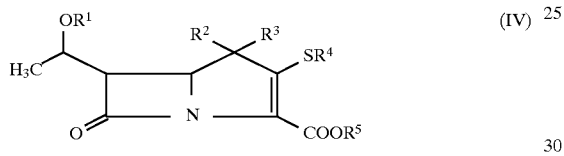

which comprises reacting a compound of the formula (II):

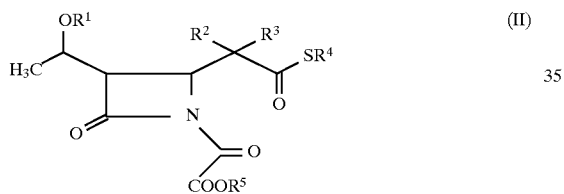

with a compound of the formula (III):

and cyclising the product of this reaction to prepare said compound of the formula (IV);
wherein:

R$^1$ represents hydrogen or a hydroxy-protecting group;

R$^2$ and R$^3$ may be the same or different and each represents hydrogen, a C$_1$–C$_6$ alkyl group or a phenyl group;

R$^4$ represents a C$_1$–C$_6$ alkyl group;

a non-aromatic heterocyclic group having from 4 to 8 ring carbon atoms and having one or two ring nitrogen atoms and optionally containing an oxygen atom, a sulphur atom, a sulphinyl group, a sulphonyl group or a carbonyl group, and optionally having one or more substituents attached to the carbon atoms or to any nitrogen atom, selected from the group consisting of (1) substituents for attachment to the ring carbon atoms selected from the group consisting of C$_1$–C$_6$ alkyl groups, cyclopropyl, cyclobutyl, cyclopentyl, cyclohexyl groups, C$_2$–C$_8$ alkoxyalkyl groups, methoxycarbonylmethyl, ethoxycarbonylmethyl, t-butoxycarbonylmethyl, benzyloxycarbonylethyl, methoxycarbonylpropyl groups, C$_2$–C$_7$ cyanoalkyl groups, C$_1$–C$_6$ haloalkyl groups, C$_1$–C$_6$ alkoxy groups, halogen atoms, C$_1$–C$_6$ aliphatic acyloxy groups, C$_1$–C$_6$ aliphatic acylamino groups, cyano group, azido group, carboxy group, C$_2$–C$_7$ alkoxycarbonyl groups, carbamoyl group, C$_1$–C$_6$ alkylthio groups, C$_1$–C$_6$ alkylsulphonyl groups, C$_1$–C$_6$ alkylsulphonyl groups, nitro group; and (2) substituents for attachment to said ring nitrogen atom(s) selected from the group consisting of C$_1$–C$_6$ alkyl groups, C$_1$–C$_6$ alkenyl groups, C$_2$–C$_6$ alkynyl groups, C$_3$–C$_8$ cycloalkyl groups, cyclopropylmethyl, cyclobutylmethyl, cyclopentylmethyl, cyclohexylmethyl, cycloheptylmethyl, 2-cyclopentylethyl, 2-cyclohexylethyl, 3-cyclopentylpropyl, 2-cyclopentylpropyl, 3-cyclohexylpropyl, 2-cyclohexylpropyl, 4-cyclopentylbutyl, 3-cyclohexylbutyl, phenyl, naphthyl groups, benzyl, phenylethyl, 3-phenylpropyl, C$_1$–C$_6$ aliphatic acyl groups, cycloponanecarbonyl, cyclobutanecarbonyl, cyclopentanecarbonyl, cyclohexanecarbonyl, cyclopropylacetyl, cyclobutylacetyl, cyclopentylacetyl, cyclohexylacetyl, 3-cyclopentylpropionyl, 3-cyclohexylpropionyl, 4-cyclopentylbutyryl, 4-cyclohexylbutyryl, benzoyl, 1-naphthoyl, 2-naphthoyl groups, phenylacetyl, 1-naphthylacetyl, 3-phenylpropionyl, hydratropoyl, cinnamoyl, phenylpropioloyl, furoyl, thenoyl, nicotinoyl, isonicotinoyl, 4-thiazolecarbonyl, 5-pyrimidinecarbonyl, 2-pyrazinecarbonyl, 2-thienylacetyl, 3-(2-thienyl)propionyl, 4-thiazolylacetyl, 2-pyridylacetyl, 4-pyridylacetyl, 5-pyrimidinylacetyl, 1-aziridinylacetyl, 1-azetidinylacetyl, 3-azetidinylacetyl, 1-pyrrolidinylacetyl, 2-pyrrolidinylacetyl, 3-pyrrolidinylacetyl, 3-(2-pyrrolidinyl)propionyl, piperidinoacetyl, 2-piperidinylacetyl, 4-piperidinylacetyl, morpholinoacetyl, 1-aziridinecarbonyl, 1-azetidinecarbonyl, 3-azetidinecarbonyl, 1-pyrrolidinecarbonyl, 2-pyrrolidinecarbonyl, 3-pyrrolidinecarbonyl, 1-piperidinecarbonyl, 2-piperidinecarbonyl, 4-piperidinecarbonyl, 4-morpholinecarbonyl, phenacyl group, sulpho group, C$_1$–C$_6$ alkylsulphonyl groups, C$_1$–C$_6$ alkylsulphonyl groups, C$_2$–C$_6$ alkylsulphonyl groups, C$_2$–C$_6$ alkylsulphonyl groups, cyclopropylsulphonyl, cyclobutylsulphonyl, cyclopentylsulphonyl, cyclohexylsulphonyl, cyclopropylmethylsulphonyl, cyclobutylmethylsulphonyl, cyclopentylmethylsulphonyl, cyclohexylmethylsulphonyl, 2-cyclopentylethylsulphonyl, 2-cyclohexylethylsulphonyl, 3-cyclopentylpropylsulphonyl, 2-cyclopentylpropylsulphonyl, phenylsulphonyl, 1-naphthylsulphonyl, 2-naphthylsulphonyl, benzylsulphonyl, phenethylsulphonyl, 3-phenylpropylsulphonyl, 2-phenylpropylsulphonyl, 2-thienylsulphonyl, 4-thiazolylsulphonyl, 2-pyridylsulphonyl, 4-pyridylsulphonyl, 2-thienylmethylsulphonyl, 3-(2-thienyl)propylsulphonyl, 4-thiazolylmethylsulphonyl, 2-pyridylmethylsulphonyl, 4-pyridylmethylsulphonyl group, groups of the formula

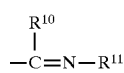

wherein R$^{10}$ represents a hydrogen atom or a C$_1$–C$_4$ alkyl group and R$^{11}$ represents a hydrogen atom, allyloxycarbonyl, 2-methylallyloxycarbonyl, 2-chloroallyloxycarbonyl, 2,2,2-trichloroethoxycarbonyl, 2,2,2-tribromoethoxycarbonyl, p-nitrobenzyloxycarbonyl or o-nitrobenzyloxycarbonyl,
groups of the formula

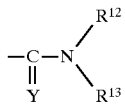

wherein $R^{12}$ and $R^{13}$ are the same or different and each represents a hydrogen atom or a $C_1$–$C_4$ alkyl group and Y represents an oxygen atom, a sulphur atom or an imino group which may be optionally substituted with a $C_1$–$C_4$ alkyl group,
$C_2$–$C_7$ alkoxycarbonyl groups, benzyloxycarbonyl, phenethyloxycarbonyl, p-nitrobenzyloxycarbonyl and o nitrobenzyloxy carbonyl group; and
the substituents attached to the nitrogen atoms of the non-aromatic heterocyclic groups may be substituted with one or more groups selected from the group consisting of $C_1$–$C_4$ alkyl groups, $C_1$–$C_4$ alkoxy groups, hydroxy, amino, halogen, $C_1$–$C_5$ aliphatic acyloxy groups, $C_1$–$C_5$ aliphatic acylamino groups, cyano, azido, carboxy, $C_2$–$C_5$ alkoxycarbonyl groups, the carbamoyl group, $C_1$–$C_4$ alkylthio group, $C_1$–$C_4$ alkylsulphonyl groups, $C_1$–$C_4$ alkylsulphonyl groups, nitro group, and groups of formula

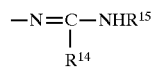

wherein $R^{14}$ and $R^{15}$ are the same or different and each represents a hydrogen atom or a $C_1$–$C_4$ alkyl group;
a substituted alkyl group, said substituted alkyl groups being selected from the group consisting of a hydroxyalkyl group,
a protected hydroxy alkyl group, an aminoalkyl group, and a protected aminoalkyl group;
a group represented by the formula

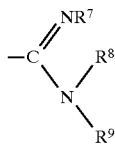

wherein $R^7$, $R^8$, and $R^9$ are the same or different and each represents hydrogen, methyl, ethyl, an aminoprotecting group, or $R^7$ and $R^8$ or $R^8$ and $R^9$, together with the atom or atoms to which they are attached, form a ring and when $R^8$ and $R^9$ form a ring, they together represent ethylene, trimethylene, tetramethylene, pentamethylene or hexamethylene, and when $R^7$ and $R^8$ form a ring, $R^7$ and $R^8$ together represent ethylene or trimethylene;
an aryl-substituted alkyl group, selected from the group consisting of benzyl, p-methoxybenzyl, m-nitrobenzyl, o-methylbenzyl, p-bromobenzyl and p-aminobenzyl; furfuryl;
an alkyl group having a non-aromatic heterocyclic substituent, the alkyl group of which is a $C_1$–$C_4$ alkyl, and the non-aromatic heterocyclic substituent is selected from the substituted or unsubstituted non-aromatic heterocyclic groups within the definition hereinbefore of $R^4$;
an alkenyl group or a substituted alkenyl group, selected from the group consisting of vinyl, allyl, 1-propenyl and 2-butenyl;
an alkynyl group or a substituted alkynyl group selected from the group consisting of ethynyl, 2-propynyl and 1-propynyl;
and when $R^4$ represents a substituted alkenyl or alkynyl group as defined above, the substituents are selected from the group consisting of the formula —$NR^{16}R^{17}$ wherein $R^{16}$ and $R^{17}$ are the same or different and each represents hydrogen, methyl, ethyl, propyl, isopropyl group, formyl, acetyl, propionyl, isobutyryl, chloroacetyl, trifluoroacetyl, benzoyl group or an amino-protecting group; groups of the formula —$CONHR^{18}$, wherein $R^{18}$ represents a hydrogen, methyl, ethyl, propyl, or an amino-protecting group; groups of the formula —$NHCONHR^{18}$; groups of the formula —$COOR^{19}$ wherein $R^{19}$ represents hydrogen, methyl, ethyl, propyl or a carboxy-protecting group; groups of the formula —$SR^{20}$, wherein $R^{20}$ represents hydrogen, methyl, ethyl, propyl, allyl, vinyl, 1-methylvinyl, 1-propenyl, ethynyl, 2-propynyl, 1-propynyl, cyclopropyl, cyclopentyl, cyclohexyl, cyclopropylmethyl, cyclopentylmethyl, 2-cyclohexylethyl, 2-cyclopentylethyl, benzyl, phenylethyl, p-methoxybenzyl, p-bromobenzyl, phenyl, p-tolyl, p-methoxyphenyl, thienyl, furyl, imidazolyl, pyridyl, thienylmethyl, 2-thienylmethyl, pyridylmethyl, imidazolylmethyl and thiazolylmethyl; groups of the formula —$S(:O)R^{20}$; groups of the formula —$SO_2R^{21}$ wherein $R^{21}$ represents any of the groups defined for $R^{20}$ or methoxy, ethoxy or propoxy; groups of formula —$OSO_2R^{20}$; cyano; nitro; and azido groups;

$R^5$ represents hydrogen, or a carboxy-protecting group;

$R^6$ represents an alkoxy group having from 1 to 6 carbon atoms, or a phenoxy group selected from the group consisting of phenoxy, p-methylphenoxy, p-methoxyphenoxy groups, and a dialkylamino group wherein each alkyl group has from 1 to 6 carbon atoms, or two $R^6$ groups together represent an o-phenylenedioxy group, and the other $R^6$ represents any other $R^6$ group, or the three $R^6$ groups together represent a group of the formula $CH_3$—($CH_2$—O—)$_3$.

3. The process of claim 1 wherein $R^4$ represents said $C_1$–$C_6$ alkyl group.

4. The process of claim 1 wherein $R^4$ is said non-aromatic heterocyclic group and said non-aromatic heterocyclic group contains one ring nitrogen atom.

5. The process of claim 1 wherein $R^4$ is said non-aromatic heterocyclic group and said non-aromatic heterocyclic group contains two ring nitrogen atoms.

6. The process of claim 2 wherein $R^4$ represents said $C_1$–$C_6$ alkyl group.

7. The process of claim 2 wherein $R^4$ is said non-aromatic heterocyclic group and said non-aromatic heterocyclic group contains one ring nitrogen atom.

8. The process of claim 2 wherein $R^4$ is said non-aromatic heterocyclic group and said non-aromatic heterocyclic group contains two ring nitrogen atoms.

9. The process of claim 1 wherein said non-aromatic heterocyclic group of $R^4$ contains one or two ring nitrogen atoms.

10. The process of claim 2 wherein said non-aromatic heterocyclic group of $R^4$ contains one or two ring nitrogen atoms.

11. A process as claimed in claim 1, wherein said non-aromatic heterocyclic group is an azetidinyl, pyrrolidinyl, piperidinyl, morpholinyl, tetrahydropyrimidinyl, thiazolidinyl, oxazolidinyl, hexahydropyrimidinyl, imidazolidinyl or octahydroazocinyl group.

12. A process as claimed in claim 1, wherein:

$R^1$ represents a trimethylsilyl, t-butyldimethylsilyl, p-nitrobenzyl, o- or p-nitrobenzyloxycarbonyl, allyloxycarbonyl, 2-chloroallyloxycarbonyl, 2,2,2-tribromoethoxycarbonyl, 1-ethoxyethyl or chloroacetyl group or hydrogen;

$R^2$ and $R^3$ both represent hydrogen atoms or one represents a $C_1$–$C_4$ hydrogen and one represents alkyl;

$R_4$ represent: a $C_1$–$C_4$ alkyl, t-butyldimethylsilyloxyethyl, p-nitrobenzyloxycarbonylaminoalkyl, (2,2,2-tribromoethoxycarbonylamino)alkyl, (p-nitrobenzyloxycarbonylaminoethoxy)alkyl, $N^1,N^1,N^2$-trimethylamidinomethyl, 1-(p-nitrobenzyloxycarbonyl)pyrrolidin-3-yl, 1-acetylpyrrolidin-3-yl, 1-[N-(p-nitrobenzyloxycarbonyl)acetimidoyl]pyrrolidin-3-yl, 1-acetimidoylpyrrolidin-3-yl, 1-(N-methylacetimidoyl)pyrrolidin-3-yl, 1-[N-(p-nitrobenzyloxycarbonyl)formimidoyl]pyrrolidin-3-yl, 1-(N-methylformimidoyl)pyrrolidine-3-yl, 1-p-nitrobenzyloxycarbonylpiperidin-3-yl, 2-oxohexahydropyrimidin-5-yl, 3,4,5,6-tetrahydro-2-methylpyrimidin-5-yl, 1,4,5,6-tetrahydro-2-methoxymethyl-1-(p-nitrobenzyloxycarbonyl)pyrimidin-5-yl, 1-[1-(p-nitrobenzyloxycarbonyl)pyrrolidine-3-yl]ethyl, 1-(4-[N-(p-nitrobenzyloxycarbonyl)acetimidoyl]morpholin-2-yl)ethyl, 1-[4-(p-nitrobenzyloxycarbonyl)morpholin-2-yl]ethyl, 2-[(N-p-nitrobenzyloxycarbonylformimidoyl)amino]-ethyl or 2-acetamidovinyl group;

$R^5$ represents a hydrogen atom or a methyl, t-butyl, benzyl, diphenylmethyl, p-nitrobenzyl, o-nitrobenzyl, allyl, methylallyl, 2-chloroallyl, 2,2,2-trichloroethyl, 2,2,2-tribromoethyl or 2-trimethylsilylethyl group; and $R^6$ represent: a methoxy, ethoxy, propoxy, isopropoxy, butoxy, sec-butoxy, phenoxy, p-tolyloxy, p-methoxyphenoxy, dimethylamino, diethylamino, dipropylamine, diisopropylamino, dibutylamino, di-sec-butylamino or di-t-butylamino group.

13. A process as claimed in claim 12, wherein said non aromatic heterocyclic group is an azetidinyl, pyrrolidinyl, piperidinyl, morpholinyl, tetrahydropyrimidinyl, thiazolidino, oxazolidine, hexahydropyrimidinyl, imidazolidinyl or octahydroazocinyl group.

14. A process as claimed in claim 2, wherein:

$R^1$ represents a trimethylsilyl, t-butyldimethylsilyl, p-nitrobenzyl, o- or p-nitrobenzyloxycarbonyl, allyloxycarbonyl, 2-chloroallyloxycarbonyl, 2,2,2-tribromoethoxycarbonyl, 1-ethoxyethyl or chloroacetyl group or hydrogen;

$R^2$ and $R^3$ both represent hydrogen atoms or one represents hydrogen and one represents alkyl a $C_1$–$C_4$;

$R^4$ represents: a $C_1$–$C_4$ alkyl, t-butyldimethylsilyloxyethyl, p-nitrobenzyloxycarbonylaminoalkyl, (2,2,2-tribromoethoxycarbonylamino)alkyl, (p-nitrobenzyloxycarbonylaminoethoxy)alkyl, $N^1,N^1,N^2$-trimethylamidinomethyl, 1-(p-nitrobenzyloxycarbonyl)pyrrolidin-3-yl, 1-acetylpyrrolidin-3-yl, 1-[N-(p-nitrobenzyloxycarbonyl)acetimidoyl]pyrrolidin-3-yl, 1-acetimidoylpyrrolidin-3-yl, 1-(N-methylacetimidoyl)pyrrolidine-3-yl, 1-[(N-(p-nitrobenzyloxycarbonyl)formimidoyl]pyrrolidin-3-yl, 1-(N-methyl- formimidoyl)pyrrolidin-3-yl, 1-p-nitrobenzyloxycarbonylamino-3-yl, 2-oxohexahydropyrimidin-5-yl, 3,4,5,6-tetrahydro-2-methylpyrimidin-5-yl, 1,4,5,6-tetrahydro-2-methoxymethyl-1-(p-nitrobenzyloxycarbonyl)pyrimidin-5-yl, 1-[1-(p-nitrobenzyloxycarbonyl)pyrrolidin-3-yl]ethyl, 1-(4-[N-(p-nitrobenzyloxycarbonyl)acetimidoyl]morpholin-2-yl)ethyl, 1-[4-(p-nitrobenzyloxycarbonyl)morpholin-2-yl]ethyl, 2-[(N-p-nitrobenzyloxycarbonylformimidoyl)amino]ethyl 3-pyridyl, 4-pyridyl, 1,3,5-triazine-2-yl or 2-acetamidovinyl group;

$R^5$ represents a hydrogen atom or a methyl, t-butyl, benzyl, diphenylmethyl, p-nitrobenzyl, o-nitrobenzyl, allyl, methylallyl, 2-chloroallyl, 2,2,2-trichloroethyl, 2,2,2-tribromoethyl or 2-trimethylsilylethyl group; and $R^6$ represents: a methoxy, ethoxy, propoxy, isopropoxy, butoxy, sec-butoxy, phenoxy, p-tolyloxy, p-methoxyphenoxy, dimethylamino, dipropylamino, diisopropylamino, dibutylamino, di-sec-butylamino or di-t-butylamino group.

15. A process as claimed in claim 2, wherein:

$R^1$ represents a trimethylsilyl, t-butyldimethylsilyl, p-nitrobenzyl, p-nitrobenzyloxycarbonyl, allyloxycarbonyl, 2,2,2-tribromoethoxycarbonyl, 1-ethoxyethyl or chloroacetyl group;

$R^2$ and $R^3$ both represent hydrogen atoms;

$R^4$ represents a $C_1$–$C_4$ alkyl group; a protected hydroxyalkyl group; a protected aminoalkyl group; an $N^1$, $N^1$, $N^2$-trimethylamidinomethyl group; a benzyl group; a phenyl or 2-naphthyl group; a 1-(p-nitrobenzyloxycarbonyl)pyrrolidin-3-yl, 1-acetylpyrrolidin-3-yl, 1-[N-(p-nitrobenzyloxycarbonyl)acetimidoyl]pyrrolidin-3-yl, 1-(N-methylacetimidoyl)pyrrolidin-3-yl, 1-[N-(p-nitrobenzyloxycarbonyl)formimidoyl]pyrrolidin-3-yl, 1-(N-methylformimidoyl)pyrrolidin-3-yl, 2-oxohexahydropyrimidin-5-yl, 3,4,5,6-tetrahydro-2-methylpyrimidin-5-yl or 3,4,5,6-tetrahydro-2-methyl-3-(p-nitrobenzyloxycarbonyl)pyrimidin-5-yl group; 1-[1-(p-nitrobenzyloxycarbonyl)pyrrolidin-3-yl]ethyl, 1-(1-acetylpyrrolidin-3-yl)ethyl, 1-(1-[N-(p-nitrobenzyloxycarbonyl)-formimidoyl]pyrrolidin-3-yl)ethyl, 1-(1-[N-(p-nitrobenzyloxycarbonyl)acetimidoyl]pyrrolidine-3-yl)ethyl, 1-(4-[N-(p-nitrobenzyloxycarbonyl)formimidoyl]morpholin-2-yl)-ethyl, 1-(4-[N-(p-nitrobenzyloxycarbonyl)acetimidoyl]-morpholin-2-yl)ethyl, 1-[4-(p-nitrobenzyloxycarbonyl)morpholin-2-yl]ethyl, 1-(4-acetylmorpholin-2-yl)ethyl or 2-[(N-p-nitrobenzyloxycarbonylformimidoyl)amino]ethyl groups; or a 2-pyridyl, 3-pyridyl, 4-pyridyl, 2-furyl, 3-furyl, 1,2,4-triazol-3-yl or 2-thiazolyl groups;

$R^5$ represents a hydrogen atom or a methyl, t-butyl, benzyl, diphenylmethyl, p-nitrobenzyl, o-nitrobenzyl, allyl, 2-chloroallyl, 2,2,2-trichloroethyl, 2,2,2-tribromoethyl or 2-trimethylsilylethyl groups; and $R^6$ represents: a methoxy, ethoxy, propoxy, isopropoxy, butoxy, sec-butoxy, phenoxy, p-tolyloxy, p-methoxyphenoxy, dimethylamino, diethylamino, dipropylamino, diisopropylamino, dibutylamino, di-sec-butylamino or di-t-butylamino groups.

16. A process as claimed in claim 2, wherein said compound of formula (III) is triethyl phosphite, tripropyl phosphite or triisopropyl phosphite.

17. A process as claimed in claim 2, wherein the cyclization is effected without intermediate isolation of the product of the reaction between said compounds of formulae (II) and (III).

* * * * *